(12) United States Patent
Stojevic et al.

(10) Patent No.: US 11,995,557 B2
(45) Date of Patent: May 28, 2024

(54) TENSOR NETWORK MACHINE LEARNING SYSTEM

(71) Applicant: Kuano Ltd., London (GB)

(72) Inventors: Vid Stojevic, London (GB); Noor Shaker, London (GB); Matthias Bal, London (GB)

(73) Assignee: KUANO LTD., London (GB)

( * ) Notice: Subject to any disclaimer, the term of this patent is extended or adjusted under 35 U.S.C. 154(b) by 1012 days.

(21) Appl. No.: 16/618,782

(22) PCT Filed: May 30, 2018

(86) PCT No.: PCT/GB2018/051471
§ 371 (c)(1),
(2) Date: Dec. 2, 2019

(87) PCT Pub. No.: WO2018/220368
PCT Pub. Date: Dec. 6, 2018

(65) Prior Publication Data
US 2021/0081804 A1    Mar. 18, 2021

(30) Foreign Application Priority Data

May 30, 2017 (GB) ..................... 1708609
Sep. 15, 2017 (GB) ..................... 1714861

(51) Int. Cl.
*G06N 3/08* (2023.01)
*G06N 3/045* (2023.01)
(Continued)

(52) U.S. Cl.
CPC ............. *G06N 3/088* (2013.01); *G06N 3/045* (2023.01); *G06N 10/00* (2019.01); *G16B 5/20* (2019.02); *G16B 15/30* (2019.02); *G16B 40/30* (2019.02)

(58) Field of Classification Search
CPC ...... G06N 3/088; G06N 10/00; G06N 3/0454; G16B 40/30; G16B 5/20; G16B 15/30
See application file for complete search history.

(56) References Cited

U.S. PATENT DOCUMENTS 6,587,845 B1 * 7/2003 Braunheim ............ G16C 20/70
706/20
6,937,940 B2 * 8/2005 Hirono .................. G16B 15/30
702/30

(Continued)

FOREIGN PATENT DOCUMENTS

WO   WO-2007004479 A1 *  1/2007 ............. G06F 19/18
WO   WO-2009055509 A2 *  4/2009 ........... C07K 14/705

(Continued)

OTHER PUBLICATIONS

Montavon et al., "Machine Learning of Molecular Electronic Properties in Chemical Compound Space", 2013, New Journal of Physics, pp. 1-16 (Year: 2013).*

(Continued)

*Primary Examiner* — Paulinho E Smith
(74) *Attorney, Agent, or Firm* — Saul Ewing LLP

(57) ABSTRACT

The invention is machine learning based method of, or system configured for, identifying candidate, small, drug-like molecules, in which a tensor network representation of molecular quantum states of a dataset of small, drug-like molecules is provided as an input to a machine learning system, such as a neural network system. The machine learning method or system may is itself configured as a tensor network. A training dataset may be used to train the machine learning system, and the training dataset is a tensor network representation of the molecular quantum states of small drug-like molecules.

11 Claims, 31 Drawing Sheets

(51) Int. Cl.
*G06N 3/088* (2023.01)
*G06N 10/00* (2022.01)
*G16B 5/20* (2019.01)
*G16B 15/30* (2019.01)
*G16B 40/30* (2019.01)

(56) References Cited

U.S. PATENT DOCUMENTS

| | | | | |
|---|---|---|---|---|
| 8,188,033 | B2* | 5/2012 | Hicks | C07K 14/46 530/326 |
| 10,556,934 | B2* | 2/2020 | Yonath | C07D 211/54 |
| 10,650,913 | B2* | 5/2020 | Sato | G16C 10/00 |
| 2003/0149533 | A1* | 8/2003 | Hirono | G16C 20/60 702/22 |
| 2004/0083060 | A1* | 4/2004 | Church | G16C 20/40 702/19 |
| 2011/0130543 | A1* | 6/2011 | Stevens | G16C 20/64 703/12 |
| 2012/0197004 | A1* | 8/2012 | Hicks | G16B 15/30 530/300 |
| 2018/0009853 | A1* | 1/2018 | Yonath | C07H 17/08 |
| 2021/0081804 | A1* | 3/2021 | Stojevic | G16B 5/20 |
| 2021/0398621 | A1* | 12/2021 | Stojevic | G16C 20/30 |
| 2022/0188652 | A1* | 6/2022 | Pabrinkis | G06N 3/047 |
| 2022/0383992 | A1* | 12/2022 | Triendl | G06N 3/045 |

FOREIGN PATENT DOCUMENTS

| | | | | |
|---|---|---|---|---|
| WO | WO-2016120868 A1 * | 8/2016 | | C07D 211/54 |
| WO | WO-2018220368 A1 * | 12/2018 | | G06N 10/00 |
| WO | WO-2019053052 A1 * | 3/2019 | | G06N 3/0454 |
| WO | WO-2020016579 A2 * | 1/2020 | | G06N 10/20 |
| WO | WO-2022043690 A1 * | 3/2022 | | |

OTHER PUBLICATIONS

Sun, Hong Yang, "Learning over Molecules: Representations and Kernels", 2014, Harvard Library, pp. 1-16 (Year: 2014).*

Gorodetsky et al., "Efficient High-Dimensional Stochastic Optimal Motion Control Using Tensor-Train Decomposition", 2015, pp. 1-9 (Year: 2015).*

Stoudenmire et al., "Supervised Learning with Tensor Networks", 2016, 30th Conference on Neural Information Processing Systems (NIPS 2016), pp. 1-9 (Year: 2016).*

Stoudenmire et al., "Supervised Learning with Quantum-Inspired Tensor Networks," arxiv.org, Cornell University Library, pp. 1-8 (May 19, 2016) XP080702081.

International Search Report, dated Sep. 28, 2018, issued in International Application No. PCT/GB2018/051471.

* cited by examiner

| Dataset | Dataset size | Task type (#of tasks) | Model | Accuracy |
|---|---|---|---|---|
| ESOL | 1128 | Regression (1) | Weave | 87,731 |
| | | | GTN | 89,211 |
| QM7 | 7165 | Regression (1) | Weave | 65,19 |
| | | | GTN | 67,15 |
| QM8 | 10000 | Regression (16) | Graph Conv. | 58,979 |
| | | | GTN | 61,193 |
| MUV | 93127 | Classification (17) | Graph Conv. | 76,585 |
| | | | GTN | 80,06 |

FIGURE 3

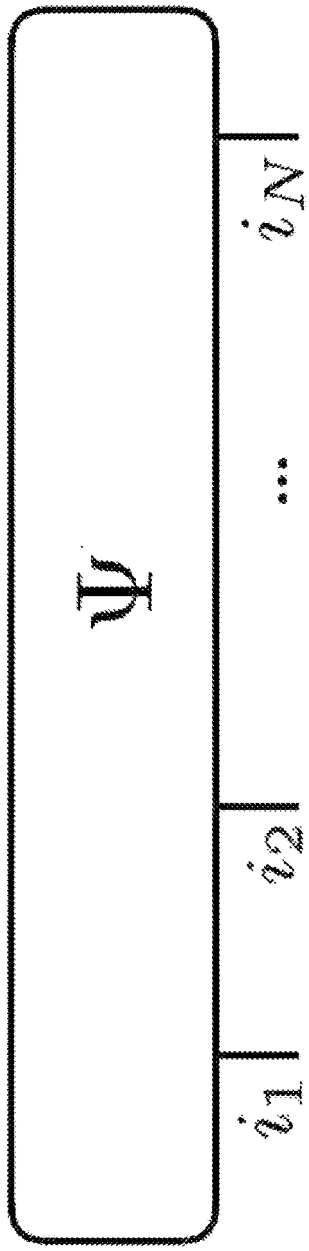
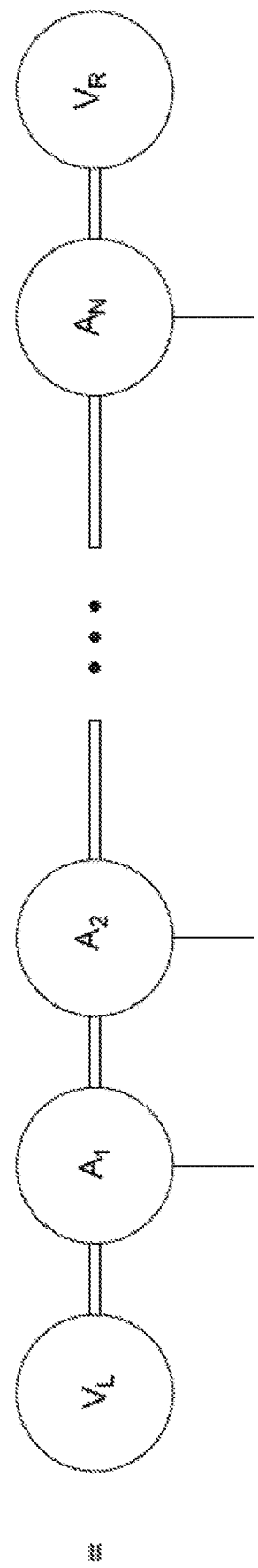
FIGURE 8

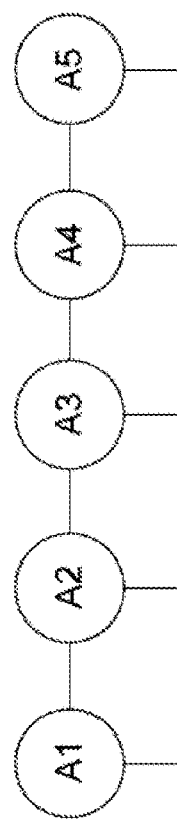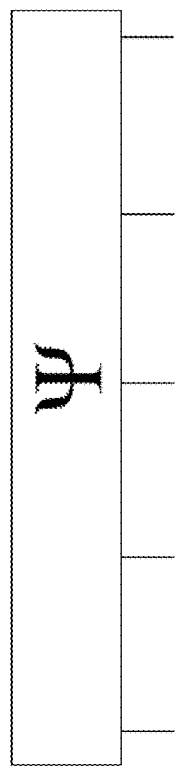
FIGURE 9

$$W^{i_1,i_2,\ldots,i_n}_{j_1,j_2,\ldots,j_n} = \sum_{\alpha_1,\alpha_2,\ldots,\alpha_{n-1}} A^{i_1}_{j_1,\alpha_1} A^{\alpha_1,i_1}_{j_1,\alpha_2} \cdots A^{\alpha_{n-1},i_n}_{j_n}$$

FIGURE 12

| Network | Parameters (FC Layer) | Parameters (Total) | Compression (FC layer) | Compression (Total) | Accuracy | Standard Deviation |
|---|---|---|---|---|---|---|
| FC-1 | 17,040,000 | 17,336,640 | 1 | 1 | 88.9 | 0.2 |
| FC-2 | 21,440 | 318,080 | 795 | 54.5 | 86.5 | 0.8 |
| MERA | 1192 | 297,832 | 14,295 | 58.21 | 88.5 | 0.1 |
| TT | 1312 | 297,952 | 12,987 | 58.19 | 87.9 | 0.2 |

FIGURE 14

| Network | Parameters (FC Layer) | Parameters (Total) | Compression (FC Layer) | Compression (Total) | Accuracy | Standard Deviation |
|---|---|---|---|---|---|---|
| FC-1 | 17,045,760 | 17,342,400 | 1 | 1 | 61.8 | 0.7 |
| FC-2 | 48,000 | 344,640 | 355 | 50.3 | 53.4 | 0.6 |
| MERA | 6952 | 303,592 | 2451 | 57.12 | 58.4 | 0.6 |
| TT | 7072 | 303,712 | 2410 | 57.10 | 57.9 | 0.6 |

FIGURE 15

Appendix 2 equations and schematics $$H(\mathbf{R},\mathbf{r})\Psi(\mathbf{R},\mathbf{r}) = E(\mathbf{R})\Psi(\mathbf{R},\mathbf{r}), \quad (1)$$

$$H(\mathbf{R},\mathbf{r}) = -\frac{1}{2}\sum_{i=1}^{N}\nabla_i^2 - \frac{1}{2}\sum_{A=1}^{M}\frac{1}{M_A}\nabla_A^2 - \sum_{i=1}^{N}\sum_{A=1}^{M}\frac{Z_A}{r_{iA}} + \sum_{i=1}^{N}\sum_{j>i}^{N}\frac{1}{r_{ij}} + \sum_{A=1}^{M}\sum_{B>A}^{M}\frac{Z_A Z_B}{R_{AB}}, \quad (2)$$

$$H_{elec}(\mathbf{R},\mathbf{r})\chi(\mathbf{R},\mathbf{r}) = E_{elec}(\mathbf{R})\chi(\mathbf{R},\mathbf{r}) \quad (3)$$

$$H_{elec}(\mathbf{R},\mathbf{r}) = -\frac{1}{2}\sum_{i=1}^{N}\nabla_i^2 - \sum_{i=1}^{N}\sum_{A=1}^{M}\frac{Z_A}{r_{iA}} + \sum_{i=1}^{N}\sum_{j>i}^{N}\frac{1}{r_{ij}}, \quad (4)$$

FIGURE 22

$$\Psi(x_1, x_2, \ldots, x_N) = \frac{1}{\sqrt{N!}} \begin{vmatrix} \chi_1(x_1) & \chi_2(x_1) & \cdots & \chi_N(x_1) \\ \chi_1(x_2) & \chi_2(x_2) & \cdots & \chi_N(x_2) \\ \vdots & \vdots & \ddots & \vdots \\ \chi_1(x_N) & \chi_2(x_N) & \cdots & \chi_N(x_N) \end{vmatrix} \quad (5)$$

$$\equiv |\chi_1, \chi_2, \ldots, \chi_N\rangle. \quad (6)$$

where the $$\chi_i(x), \forall i \in \{1, 2, \ldots, N\}$$

are a set of one-electron spin-orbital wave functions.

FIGURE 23

$$|\psi_{HF}\rangle = |\uparrow\downarrow\,\uparrow\downarrow\,\uparrow\downarrow\,|\,|\,|\,|\rangle \quad (7)$$

FIGURE 24

$$|\psi_{CI}\rangle = c_0 |\uparrow\downarrow\,\uparrow\downarrow\,\uparrow\downarrow\,|\,|\,|\,|\rangle + \sum_{ia} c_i^a |\uparrow\downarrow\,\uparrow\downarrow\,\uparrow\,|\,\downarrow^a\,|\,|\rangle + \sum_{ijab} c_{ij}^{ab} |\uparrow\downarrow\,\uparrow\downarrow\,\,|\,\downarrow^a\,\downarrow^b\,|\rangle + \ldots \quad (8)$$

$$|\psi_{CI}\rangle = (1 + T_1 + T_2 + \ldots)|\psi_{HF}\rangle. \quad (9)$$

FIGURE 25

$$\rho = |\Psi(x_1, x_2, \ldots, x_N)\rangle \langle \Psi(x_1, x_2, \ldots, x_N)|, \quad (10)$$

$$\rho^{(1)}(x_1, x_1') = N \int \Psi^*(x_1', x_2, \ldots, x_N) \Psi(x_1, x_2, \ldots, x_N) \, dx_2 \ldots dx_N, \quad (11)$$

$$\rho^{(1)}(x_1) = N \int \Psi^*(x_1, x_2, \ldots, x_N) \Psi(x_1, x_2, \ldots, x_N) \, dx_2 \ldots dx_N. \quad (12)$$

$$P^{(1)}(r_1) = \int \rho^{(1)}(r_1; s_1) \, ds_1. \quad (13)$$

$$\rho^{(2)}(x_1, x_2; x_1', x_2') = N(N-1) \int \Psi^*(x_1', x_2', \ldots, x_N) \Psi(x_1, x_2, \ldots, x_N) \, dx_3 \ldots dx_N, \quad (14)$$

$$\rho^{(2)}(x_1, x_2) = N(N-1) \int \Psi^*(x_1, x_2, \ldots, x_N) \Psi(x_1, x_2, \ldots, x_N) \, dx_3 \ldots dx_N. \quad (15)$$

FIGURE 27

$$\rho^{(1)}(x_1, x_1') = \sum_{i,j} \rho^{(1)}_{ij} \phi_i(x_1) \phi_j^*(x_1'). \quad (16)$$

$$\rho^{(1)}(x_1, x_1') = \sum_i n_i \phi_i^{NSO}(x_1) \phi_j^{*NSO}(x_1'). \quad (17)$$

$$P^{(1)}(r_1, r_1') = \sum_i n_i \phi_i^{NO}(r_1) \phi_j^{*NO}(r_1'). \quad (18)$$

Atomic orbital → NHO → NBO → NLMO → Molecular orbital, (19)

FIGURE 28

$$|\Psi_{CAS-CI}\rangle = \sum_{n_1,\ldots,n_L} C_{n_1,\ldots,n_L} |n_1 n_2 \ldots n_L\rangle, \quad (20)$$

$$\epsilon = |||\Psi\rangle - |\tilde{\Psi}\rangle||^2 = 1 - \sum_{\alpha=1}^{D} w_\alpha, \quad (21)$$

$$S_i = -\sum_{\alpha=1}^{4} w_{\alpha,i} \ln w_{\alpha,i}, \quad (22)$$

$$S_{ij} = -\sum_{\alpha=1}^{16} w_{\alpha,ij} \ln w_{\alpha,ij}, \quad (23)$$

$$I_{ij} = \frac{1}{2}(S_i + S_j - S_{ij})(1 - \delta_{ij}) \quad (24)$$

FIGURE 32

TENSOR NETWORK MACHINE LEARNING SYSTEM

CROSS REFERENCE TO RELATED APPLICATIONS

This application claims the priority of PCT/GB2018/051471, filed on May 30, 2018, which claims priority to GB Application No. GB1708609.1, filed May 30, 2017, and GB Application No. GB1714861.0, filed on Sep. 15, 2017, the entire contents of each of which being fully incorporated herein by reference.

BACKGROUND OF THE INVENTION

1. Field of the Invention

The field of the invention relates to a tensor network based machine learning system. The system may be used, for example, for small molecule drug design. The invention links the quantum physics derived concepts of tensor networks and tensor decomposition to machine learning and presents the architecture for a practical working system.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Background of the Invention

In small molecule drug design, after a disease mechanism has been identified, a new journey through chemical space is initiated. The challenge is to identify a candidate molecule that binds to a specified target protein in order to cure, prevent entirely, or mitigate the symptoms of the disease—all the while having minimal negative side effects for the patient. The process starts by filtering millions of molecules, in order to identify a hundred or so promising leads with high potential to become medicines. Around 99% of selected leads fail later in the process, both due to the inability of current technologies to accurately predict their impact on the body, and the limited pool from which they were sampled. Currently the process takes approximately 15 years and costs $2.6bn.

The very low accuracy achieved is due in part to the problem of representation of the molecules. Molecules are often represented in a simplified model using strings or graphs where the wave function and quantum properties should be taken into account. However, the description of molecular quantum states involves vector spaces whose dimension is exponentially large in the number of constituent atoms.

Another key challenge lies in the astronomical size of the search space: there are an estimated $10^{60}$ possible small drug-like molecules.

The pharma industry has largely not been able to address these challenges with truly novel methods, and as legacy approaches to discovering new drugs are drying-up, so-called "Eroom's Law" is observed: a staggering drop in R&D drug development efficiencies by a factor of one half every nine years.

The present invention addresses the above vulnerabilities and also other problems not described above.

SUMMARY OF THE INVENTION

The invention is machine learning based method of, or system configured for, identifying candidate, small, drug-like molecules, in which a tensor network representation of molecular quantum states of a dataset of small, drug-like molecules is provided as an input to a machine learning system, such as a neural network system.

The machine learning method or system may is itself configured as a tensor network. A training dataset may be used to train the machine learning system, and the training dataset is a tensor network representation of the molecular quantum states of small drug-like molecules.

The machine learning method or system may provide, as its output, tensor network representations of the molecular quantum states of small drug-like molecules to a predictive model.

The machine learning method or system may efficiently search through, sample or otherwise analyze the tensor network representations to identify candidate small drug-like molecules with required properties, such as the binding affinity with respect to a target protein.

The machine learning system method or system may:
(i) generate tensor networks for a dataset of small drug like molecules, or other chemical compounds;
(ii) correlate the tensor network description of chemical compounds, with machine learning models, where the machine learning models may themselves contain tensor network components, or be tensor networks in their entirety;
(iii) in the context of generative models, correlate the inputs and models with a latent space of a variational autoencoder model, or use it in the context of other generative models (the latent space is usually a small vector space, but may have a more general tensor network structure);
(iv) output a further dataset of candidate small drug like molecules, or other chemical compounds, via generative models.
(v) use a combination of tensorial predictive and generative molecules to guide the search through the space of small chemical compounds.

Further details are in the appended claims.

Definitions

The term 'tensor' preferably connotes a multidimensional or multi-rank array (a matrix and vector being examples of rank-2 or rank-1 tensors), where the components of the array are preferably functions of the coordinates of a space.

The term 'tensorial space' is equivalent to a tensor network.

The term 'tensor network' is defined as follows. A tensor network can be thought of as a way of representing a high rank tensor in terms of a 'bag' of small rank tensors, together with a recipe (i.e. a set of contractions along some of the dimensions of the smaller tensors) which is capable of reproducing the original high-rank tensor. In the context of quantum mechanics, given a matrix/tensor description of an observable, a tensor contraction recipe can reproduce the expectation value of that observable with respect to the wave function described by the high rank tensor (depending on the tensor network, an efficient method may or may not be available). See arxiv.org/abs/1306.2164 [A Practical Introduction to Tensor Networks: Matrix Product States and Projected Entangled Pair States Annals of Physics 349

(2014) 117-158] for details. A wave function or a quantum state of a system can be approximated or represented using a tensor network.

The term 'tensor network' is also used broadly and expansively in this specification. Specifically, the definition of a 'tensor network' in terms of a general bag-of-tensors, as given above, is very general. Commonly the term 'tensor network' used in a more restricted sense, for specific tensor networks ansätze used to describe quantum systems at low energies, and where the tensors from which the large-rank tensor is reconstructed are all small rank. Let us call these 'area-law tensor networks' (as they by construction obey the area law, up to perhaps topological corrections, see e.g. Entanglement rates and area laws; Phys. Rev. Lett. 111, 170501 (2013) arxiv.org/abs/1304.5931 and references therein). For example, even though they fit our bag-of-tensors definition above, many physicists would not consider correlator product states as tensor networks, the reason being that these in general contain high rank tensors. Now, these high rank tensors are very special for correlator product states, and in general highly sparse—and this often enables efficient evaluations of observables of interest (either via a direct contraction or using Monte Carlo methods—see e.g. Time Evolution and Deterministic Optimisation of Correlator Product States Phys. Rev. B 94, 165135 (2016) arxiv.org/abs/1604.07210 and references therein). So the ansatz is not exponentially expensive, which is the reason why it is commonly used to describe systems with non-local correlations. Nevertheless it's not generally considered a tensor network, as it is not an 'area-law tensor network'. In the context of the present patent, we will use the term tensor network in its fully general definition—not restricted to those networks that are efficiently contractible, and also allowing for tensors defined as superpositions of distinct tensor networks (e.g. a superpositions of different tensors from the same class, e.g. two matrix product states, or a superposition of a rank-n tensor decomposed as and MPS, and as a MERA). In addition, our definition allows for tensor networks describing states with volume law entanglement, which can, for example, provide descriptions of highly excited states present in transition states of small molecules in a reaction or a binding process. We will also allow for tensor networks describing density matrices—both those that obey the area law, and those that do not.

The term 'wave function space' preferably connotes a description of the quantum state of a system and optionally also connotes density matrices, for example those used to describe quantum systems in mixed or thermal states.

The term 'dimensionality' preferably connotes the number of dimensions and/or variables associated with a particular situation.

The term 'novel dataset of (candidate) chemical compounds' preferably connotes a dataset comprising at least one (candidate) chemical compound that is not in an original dataset of chemical compounds.

The term 'mode' or 'rank' preferably connotes the number of constituents of the system. The dimensionality of a tensor is, in particular, exponentially large in the number of modes The terms 'chemical compound' and 'molecule' are used interchangeably.

The term 'candidate chemical compounds' or 'candidate molecules' preferably connotes chemical compounds and/or molecules being candidates for a further process, in particular chemical compounds having a particular desired set of properties.

The term 'generative model' preferably connotes a model for generating observable data values, given some hidden parameters. Generative models include the following: generative auto encoder, RNN, GAN, Monte-Carlo tree search model, an Ising model or a restricted Boltzmann machine trained in an unsupervised manner etc. (see Exploring deep recurrent models with reinforcement learning for molecule design Workshop Track—ICLR2018 openreview.net/pdf?id=Bk0xiI1Dz, and A Generative Restricted Boltzmann Machine Based Method for High-Dimensional Motion Data Modeling; Computer Vision and Image Understanding 136 (2015): 14-22 arxiv.org/abs/1710.07831, and references therein).

The term 'cost function' preferably connotes a mathematical function representing a measure of performance of an artificial neural network, or a tensor network, in relation to a desired output. The weights in the network are optimised to minimise some desired cost function.

The term 'autoencoder' preferably connotes an artificial neural network having an output in the same form as the input, trained to encode the input to a small dimensional vector in the latent space, and to decode this vector to reproduce the input as accurately as possible.

The term 'tensorial generative autoencoder' preferably connotes an autoencoder used as part of a generative model which includes tensors, tensor networks, or tensorial decompositions, both for input data, the model itself, or for the latent layers.

It should also be appreciated that particular combinations of the various features described and defined in any aspects of the invention can be implemented and/or supplied and/or used independently.

BRIEF DESCRIPTION OF THE FIGURES

Aspects of the invention will now be described, by way of example(s), with reference to the following Figures, which each show features of the GTN system:

FIG. 3 shows a table of results.

FIG. 8 shows is a diagram showing an example of a decomposition of a tensor into a matrix product state.

FIG. 9 shows a schematic decomposition of a mode-5 tensor as a matrix product state.

FIG. 12 shows equation (1).

FIG. 14 shows a table of results.

FIG. 15 shows a table of results.

FIG. 22 shows equations (1) to (4) from Appendix 2.

FIG. 23 shows equations (5) to (6) from Appendix 2.

FIG. 24 schematically represents paired electrons as optimizing occupied orbital spaces, referenced as (7) in the Appendix 2.

FIG. 25 schematically represents configuration interaction, referenced as (8) and (9) in Appendix 2.

FIG. 27 shows equations (10) to (15) from Appendix 2.

FIG. 28 shows equations (16) to (19) from Appendix 2.

FIG. 32 shows equations (12) to (14) from Appendix 2.

DETAILED DESCRIPTION

Figure 1:
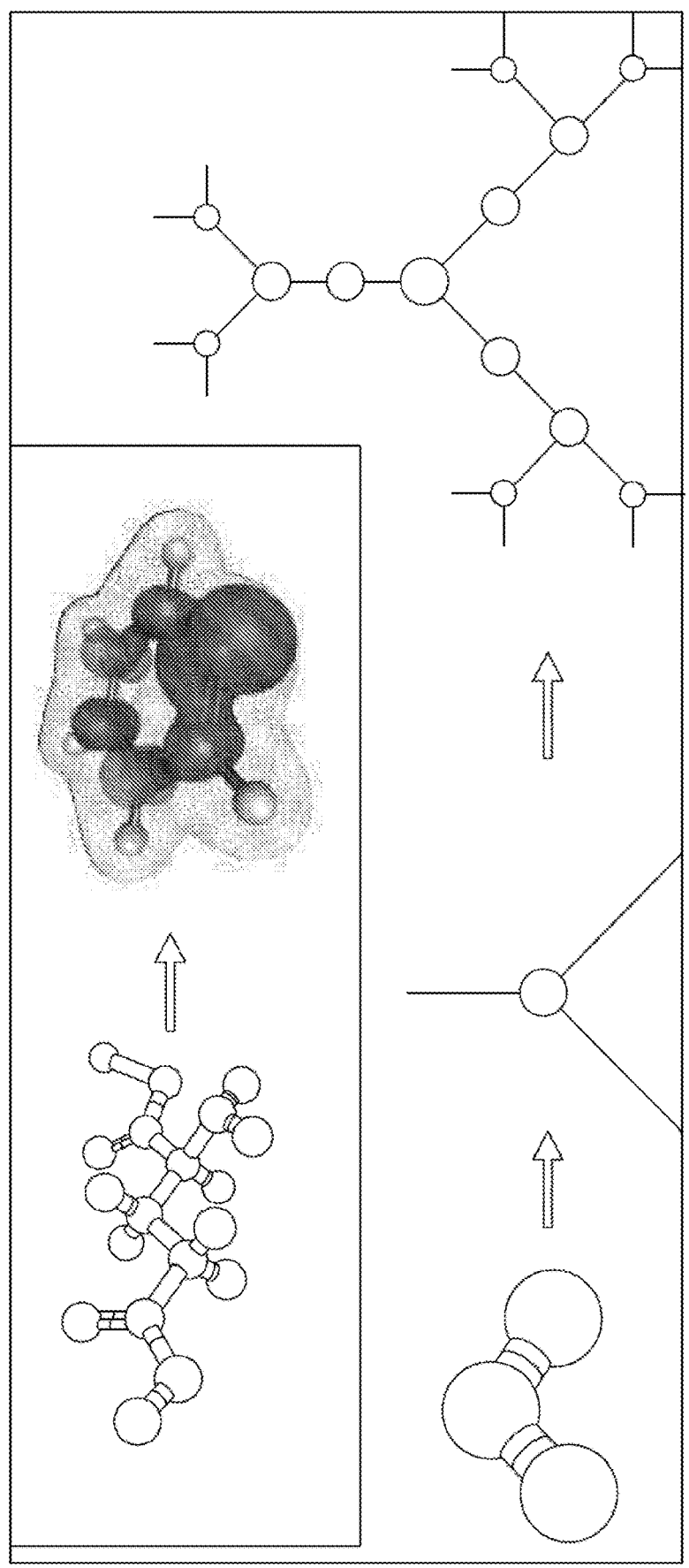
FIG. 1 shows a schematic diagram of a quantum state of a complex molecule and a tree-tensor network representation of the quantum state of $H_2O$.

We organize this Detailed Description as follows.

Section 1 is an overview of the technical problems addressed by the GTN system, and a high-level summary of how the GTN system works.

Section 2 is a more detailed discussion of how the GTN system works.

Appendix 1 is a more formal re-statement of the high-level concepts implemented in the GTN system.

Appendix 2: includes technical background, ideas, details, and preliminary results on how the GTN system adds physically-inspired entanglement features to machine learning graph models, using quantum chemistry methods and tensor network algorithms.

Appendix 3 is a paper (A. Hallam, E. Grant, V. Stojevic, S. Severini, and A. G. Green, ArXiv e-prints (2017), arXiv:1711.03357.) that demonstrates the potential of tensorial approaches, as used in the GTN system, to affect major, non-incremental, improvements to machine learning.

Section 1. Overview

This Section 1 is a high level description of the GTN system. The GTN system implements various aspects and features of the invention. GTN is an acronym for 'generative tensorial networks'.

1.1 Solving the Representation Problem

The representation problem in quantum mechanics was one of the main motivations that led the famous physicist Richard Feynman to propose quantum computers. Exploring the role of entanglement in quantum chemistry has constituted a major line of research in the field ever since, and is thriving today. Entanglement is a purely quantum mechanical feature of many particle systems, causing them to behave in an astonishingly complex, interdependent (i.e. entangled) manner. The potential of efficient quantum mechanical methods to revolutionise drug discovery has been appreciated for a long time (A. Cavalli, P. Carloni, and M. Recanatini, Chemical Reviews 106, 3497 (2006), pMID: 16967914), with chemistry applications amongst the first to be explored on novel quantum chipsets by Google, D-Wave, and IBM, which are designed specifically to address the most intractable aspects of quantum entanglement. Inaccurate quantum mechanical description of chemical reactions and binding processes is indispensable, both to achieving accurate predictions of molecular characteristics, and for an efficient search through the space of druglike molecules. The main bottleneck to modelling these processes accurately is the exponential cost of modeling quantum entanglement.

This is best encapsulated using a tensorial description of quantum states, whereby a tensor we mean a multi-dimensional array common in most programming languages.

The quantum state of n electrons is described precisely by such rank-n tensors (in general also as a function of all the electron coordinates). The computational memory cost of working with such tensors is exponential in the number of electrons and makes simulations of large quantum systems in their full generality practically impossible on classical computers, but polynomially efficient on universal quantum computers.

A fully general n-electron state of this kind is highly entangled. Thus, it does not admit an efficient description in terms of quantum states of individual electrons, but only a "collective" description via exponentially costly tensors. However, while states relevant for real world applications are entangled, it turns out that they are usually not maximally entangled—and are thus not maximally complex to represent. Optimal representations are achieved by tensor networks, a technology developed over the past 25 years mainly in the physics community. A tensor network provides a way of decomposing a general full rank tensor description of a quantum state into smaller 'building block' tensors.

The potential of efficient quantum mechanical methods to revolutionise chemistry has been appreciated for a long time that can be handled efficiently, together with a method for reconstructing the full rank tensor and calculating values of physically relevant observables.

With reference to FIG. 1, a schematic depiction of a quantum state of a complex molecule (inset), and an example of increasingly complex tree-tensor network representations of the quantum state of $H_2O$ are shown.

In the past 2-3 years a surge of interdisciplinary research on the boundary between machine learning and tensor networks has been taking place. It has been realised that tensor networks can be used for standard machine learning problems (E. Miles Stoudenmire and D. J. Schwab, Supervised Learning with Quantum-Inspired Tensor Networks; Advances in Neural Information Processing Systems 29, 4799 (2016) ArXiv e-prints (2016), arXiv:1605.05775), and that deep neural networks can be used to model quantum systems (G. Carleo and M. Troyer, Solving the Quantum Many-Body Problem with Artificial Neural Networks; Science 355, 602 (2017)ArXiv e-prints (2016), arXiv:1606.02318).

The GTN system is predicated on the realisation that the optimal way to apply machine learning to molecular problems is precisely via the technology of tensor networks.

1.2 Solving the Search Problem

Addressing the search problem requires combining advanced tensor network representations of molecules with deep generative models. The aim is to search the exponentially large search space made up of a set of possible small drug-like molecules (or the space of small molecules considered for other applications) in a meaningful way.

A generative method provides a way of capturing the essence of a certain data set, in order to then generate completely novel, hitherto unseen, data samples. The idea has been around for a long time, and is independent of deep learning (C. M. Bishop, Pattern Recognition and Machine Learning (Information Science and Statistics) (Springer-Verlag New York, Inc., Secaucus, NJ, USA, 2006, N. Shaker, J. Togelius, and M. J. Nelson, Procedural Content Generation in Games, Computational Synthesis and Creative Systems (Springer, 2016)). However, the advance of Generative Adversarial Networks has brought generative methods squarely into the era of deep learning, opening the way to significantly more ambitious applications. Over the past two years this has been impressively demonstrated, enabling the generation of novel images, pieces of music and art, as well as molecular data (R. Gómez-Bombarelli, D. Duvenaud, J. M. Hernandez-Lobato, J. Aguilera-Iparraguirre, T. D. Hirzel, R. P. Adams, and A. Aspuru-Guzik, ArXiv e-prints (2016), Automatic chemical design using a data-driven continuous representation of molecules, arXiv: 1610.02415). Generative methods are only as good as the quality of the data upon which they are trained. Thus, to generate truly novel molecules, maximally accurate and efficient representations of molecular quantum states need to be employed.

A sophisticated generative method should thus have the capacity to handle advanced tensor network descriptions of molecules as inputs, and to thereby efficiently capture complex properties involving highly entangled quantum mechanical states crucial to drug discovery. GTN is developing the GTN system specifically to address these issues. GTN's models are inspired by standard deep generative models, such as GANs and variational autoencoders, but require custom architectures and tensorial layers to permit compatibility with tensorial inputs. With this, the GTN system is capable of sampling novel high quality molecules from the $10^{80}$ drug-like space, eclipsing the capabilities of current generative approaches.

1.3 The GTN System Technology Pipeline

Figure 2A:
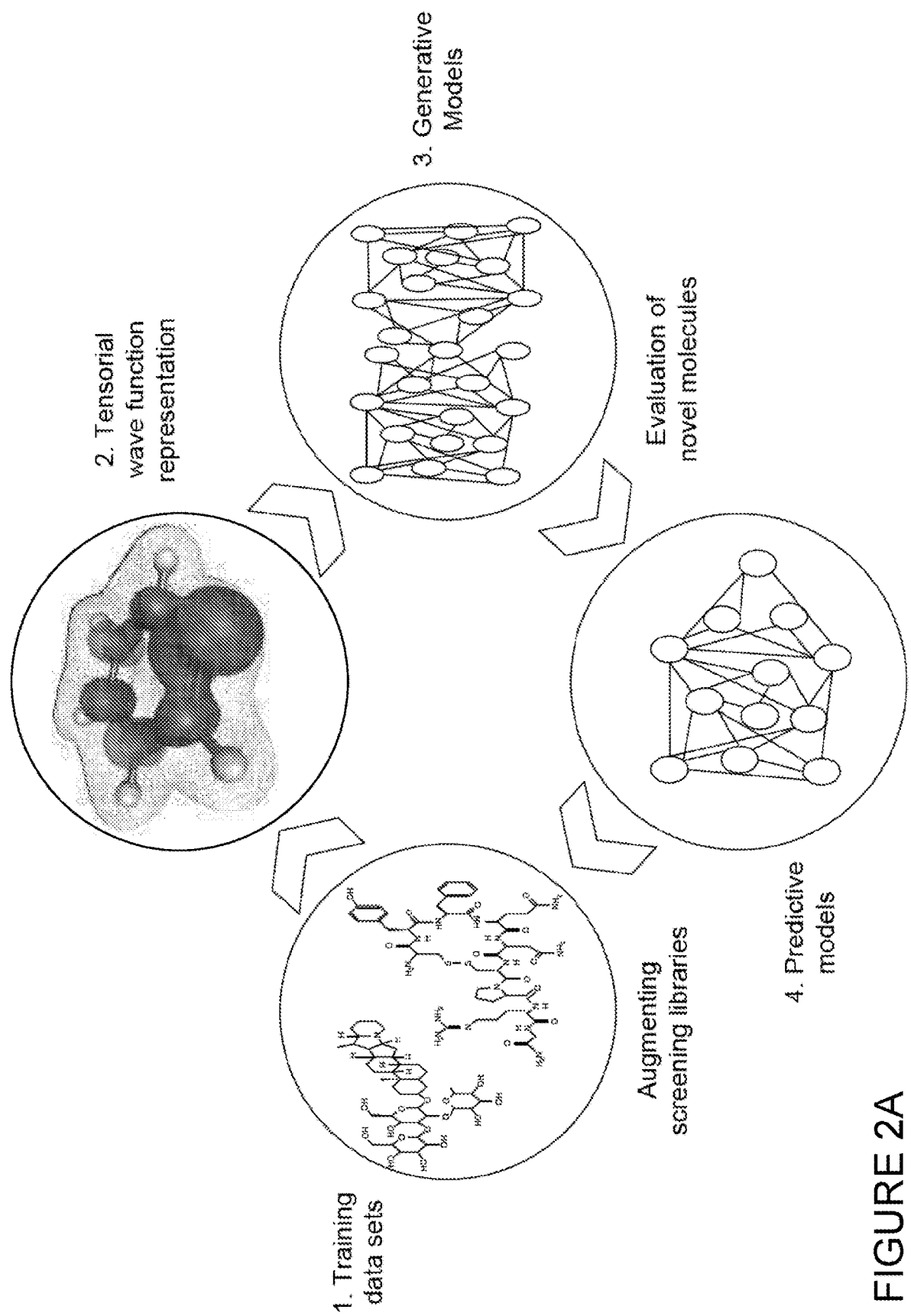
FIG. 2A schematically illustrate the GTN technology pipeline.

With reference to FIG. 2A, the technology pipeline is presented. It starts with a molecular library appropriate for the disease mechanism being addressed (1). Tensorial representations are used to model the molecules in order to capture quantum entanglement, and other quantum and non-quantum correlations (2), and these tensor networks are used as inputs on which the generative network is trained (3). The process is guided by the capacity of the proposed molecules to bind to a target protein, as well as any number of relevant optimisation constraints, including absorption, distribution, metabolism and toxicity measures. Predictive models, again utilising tensorial inputs and tensor networks in their construction, are used in order to both screen the generative outputs and add high quality molecules to the original library (4). The iterative cycle is repeated to maximise the quality of proposed molecules.

Figure 2B:
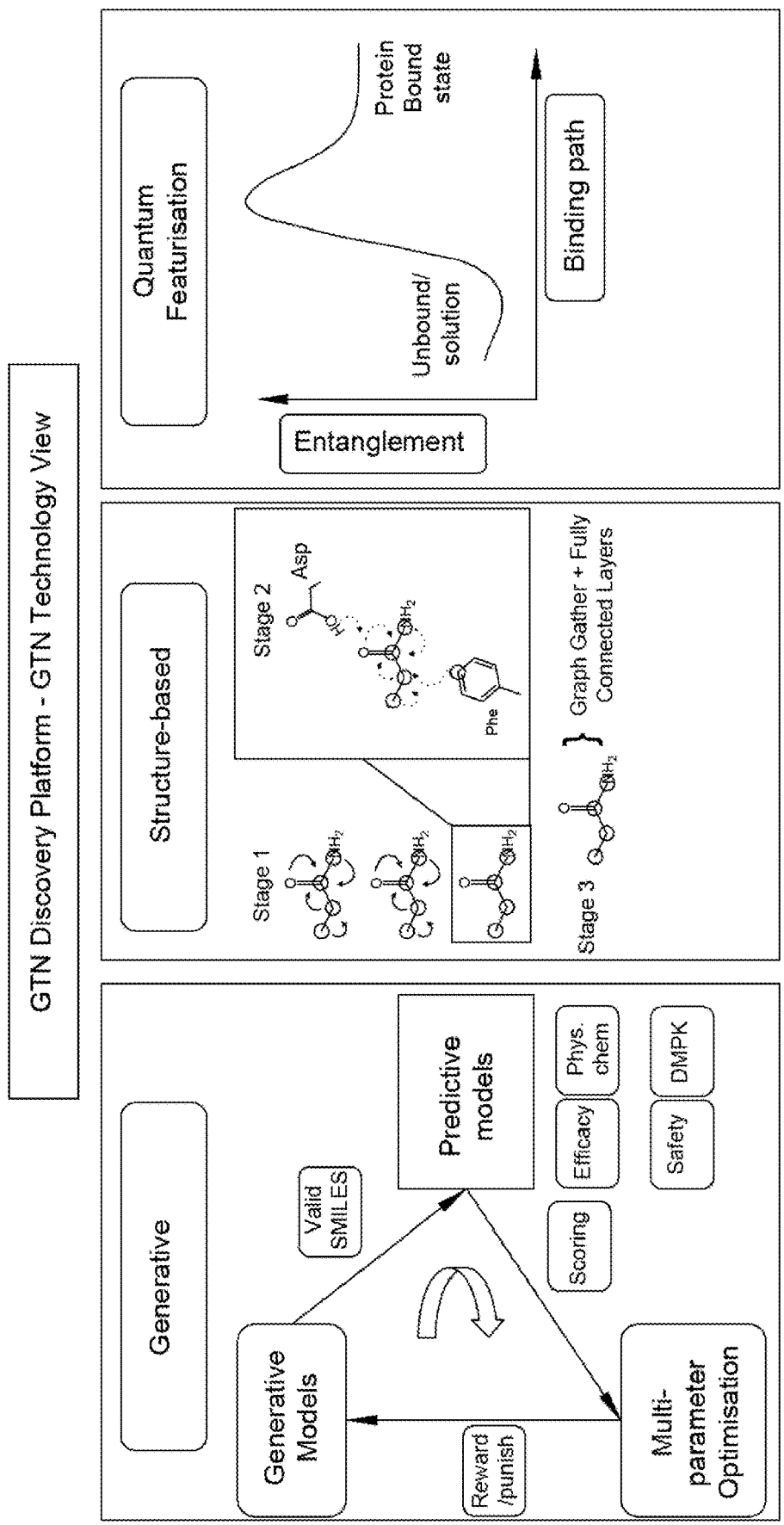
FIG. 2B schematically illustrate the GTN technology platform.

FIG. 2B shows the GTN Discovery platform, using a generative model suite. The generative model and predictive models utilise any combination of tensorial methods, both as part of the models and to describe the input data, described in the patent. The output of the generative models is ranked, or the model itself modified to focus on a particular subset of chemical space that satisfies a number of properties. These properties are determined, and the search and/or output of the generative model is guided by the outputs of ligand based predictive models (i.e. those models that do not utilise target protein information—these can predict e.g. efficacy, physchem properties, binding affinities with respect to some set of proteins), or by similarity with respect to a set of molecules one wants to find close analogues of. Multi-parameter optimisation can be performed using any number of standard methods, such as Hillclimb MLE or any number of reinforcement learning variants (see Exploring deep recurrent models with rein-forcement learning for molecule design; Workshop Track—ICLR2018; openreview.net/pdf?id=Bk0xiI1Dz).

Structure based machine learning models are sophisticated predictive models that utilise both information about target proteins and small molecules in order to predict binding affinities. Quantum featurisation of input molecules can be used both for ligand based and for structure based models, in the latter case one needs to take into account the quantum mechanical properties both of the binding pocket on the protein and of the ligand. Molecular dynamics methods can be used to improve the results, and also to enlarge the set of data points machine learning models are trained on.

Figure 2C:
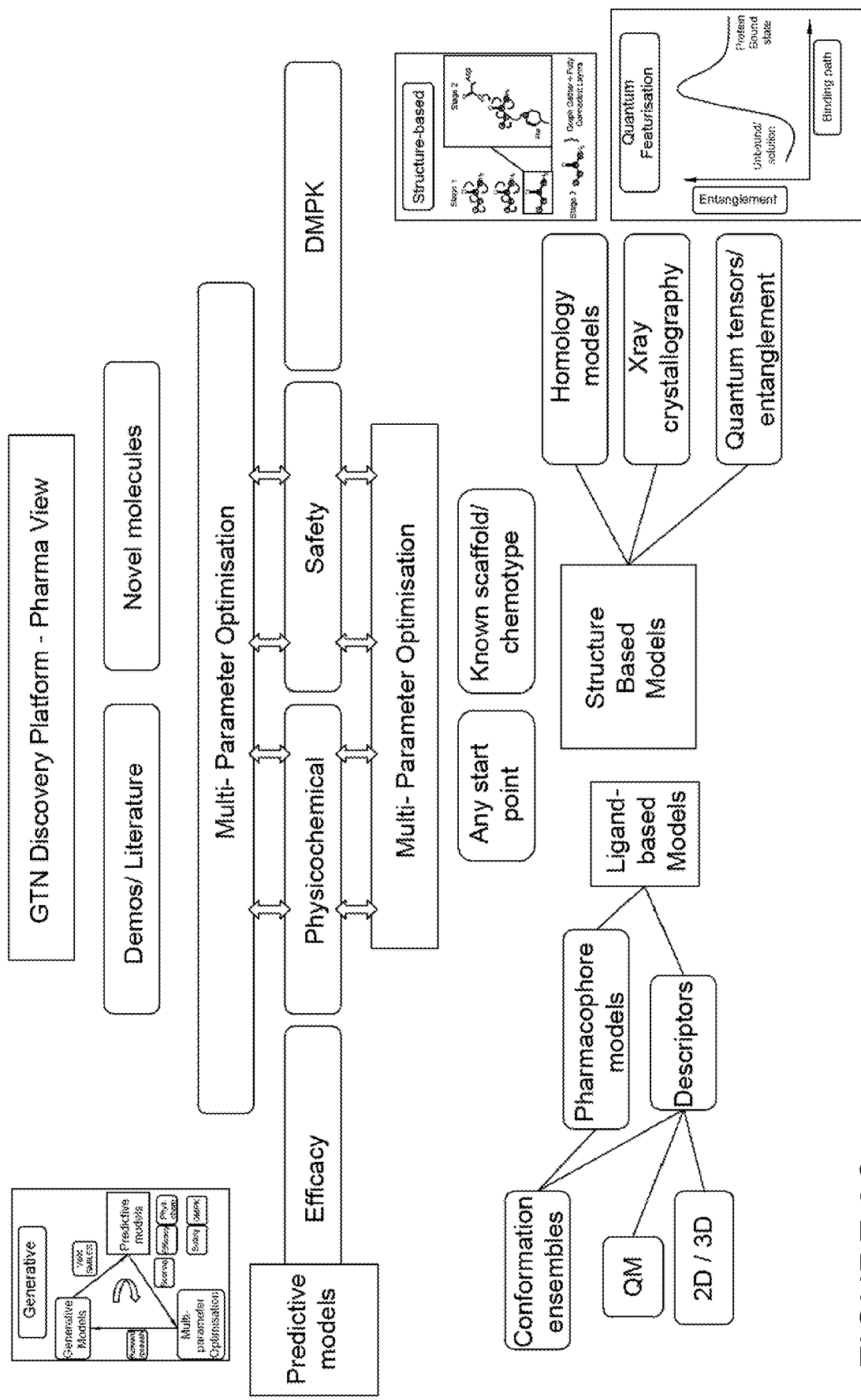
FIG. 2C schematically illustrate the GTN technology platform in the context of the pharma ecosystem.

FIG. 2C is a schematic view of where the technology components described in FIG. 2B fit in to the pharmaceutical industry eco-system.

1.4 GTN Vs. Current Approaches

The most sophisticated deep learning approaches for molecular prediction currently utilise graph convolutional networks (D. Duvenaud, D. Maclaurin, J. Aguilera-Iparraguirre, R. Gómez-Bombarelli, T. Hirzel, A. Aspuru-Guzik, and R. P. Adams, Convolutional Networks on Graphs for Learning Molecular Fingerprints ArXiv e-prints (2015), arXiv: 1509.09292; S. Kearnes, K. McCloskey, M. Berndl, V. Pande, and P. Riley, Journal of Computer-Aided Molecular Design 30, 595 (2016), Molecular GraphConvolutions: Moving Beyond Fingerprints J Comput Aided Mol Des (2016), arXiv:1603.00856; T. N. Kipf and M. Welling, Semi-Supervised Classification with Graph Convolutional Networks, ArXiv e-prints (2016), arXiv:1609.02907). At the inputs, molecules are represented in terms of graphs, i.e. two-dimensional ball-and-stick models, together with standard per-atom chemical descriptors. Such inputs already require a significant overhaul of standard neural network techniques, since convolutional or RNN layers designed for image or text data do not respect graph structures. Current generative models for chemistry utilize text input data, in the form of the SMILES representation of molecules (R. Gómez-Bombarelli, D. Duvenaud, J. M. Hernandez-Lobato, J. Aguilera-Iparraguirre, T. D. Hirzel, R. P. Adams, and A. Aspuru-Guzik, ArXiv e-prints (2016), arXiv:1610.02415) as this enables many established generative natural language approaches to be used out of the box. However, such approaches are too simplistic to generate truly interesting novel molecules. Some more recent models have attempted graph-to-graph trained generative models (openreview.net/forum?id=SJlhPMWAW), but unresolved issues related to the permutation group gauge symmetry of graph inputs mean that these approaches remain sub-optimal at present. DeepChem, a popular deep learning library for chemistry provides access to many machine learning methods and datasets, including graph convolutional networks, under a unified scalable framework. GTN is interfacing with DeepChem and Tensorflow in order to ensure scalability.

We note also, that graph models can be used in the structure based context, by including both the ligand and the protein binding pocket in a large graph.

Tensorial networks can naturally be used to decompose high rank structures appearing in certain graph models, and this provides a potentially easy way to introduce quantum featurisation and modelling in the context of graph models (see arxiv.org/pdf/1802.08219.pdf) (see Appendix 2).

By implementing tensorial ideas in predictive models, GTN has demonstrated its capacity to consistently beat state-of-the-art predictive models on a number of tasks. A recently publication (A. Hallam, E. Grant, V. Stojevic, S. Severini, and A. G. Green, ArXiv e-prints (2017), arXiv: 1711.03357) provides a proof-of concept demonstration of the disruptive potential of tensor networks, by achieving a compression of deep learning models for image classification by a factor of 160, at less than 1% drop in accuracy.

1.5 GTN System Results

Results are now described where tensorial technology is incorporated in conjunction with two types of graph convolutional networks, the so-called "Weave" and "GraphConv" and "MPNN" networks, and various variants thereof—the current state-of-the-art in predictive models for chemicals ([33] D. Duvenaud, D. Maclaurin, J. Aguilera-Iparraguirre, R. Gómez-Bombarelli, T. Hirzel, A. Aspuru-Guzik, and R. P. Adams, ArXiv e-prints (2015), arXiv: 1509.09292; S. Kearnes, K. McCloskey, M. Berndl, V. Pande, and P. Riley, Journal of Computer-Aided Molecular Design 30, 595 (2016), arXiv:1603.00856). Our current demonstration of the tensorial technology operates at the level of the network, leaving the input data unchanged, and also implements a quantum mechanics inspired machine learning step. The results, displayed in FIG. 3, consistently show incremental improvements of between 1-5% over state-of-the-art approaches.

The implementation of full tensorial molecular inputs may achieve increasingly higher accuracies and begin generating novel molecules for screening. The datasets referenced in FIG. 3, are the following:

ESOL: solubility data for 1,128 compounds.

QM7: 7,165 molecules from the GDB-13 database. Atomization energy for each molecule is determined using ab initio density functional theory.

QM8: 10,000 molecules from the GDB-13 database. 16 electronic properties (atomization energy, HOMO/LUMO eigenvalues, etc.) for each molecule are determined using ab-initio density functional theory.

MUV (Maximum Unbiased Validation): benchmark dataset selected from PubChem BioAssay by applying a refined nearest neighbour analysis. It contains 17 especially challenging tasks for 93,127 compounds and is specifically designed for validation of virtual screening techniques.

Tox21 ("Toxicology in the 21st Century"): contains qualitative toxicity measurements for 8014 compounds on 12 different targets, including nuclear receptors and stress response pathways.

β-Secretase 1 (BACE-1) Inhibitors: Consists of a set of around 1000 molecules inhibiting the BACE-1 protein. IC50 values are available for nearly all of these, and full crystallography ligand-protein structures for a subset. Molecules in the dataset originate from a large variety of sources: pharma, biotechnology and academic labs. The aim is to validate our technology on both classification and regression tasks, on a real-world problem for which the dataset size is relatively small.

PDBbind: The context is target based design. A curated subset of the PDB database, which has experimentally measured binding affinities for bio-molecular complexes, and provides 3D coordinates of both ligands and their target proteins derived from crystallography measurements. The challenge consists of incorporating both ligand and target space information into the models. The aim is to develop networks that optimally incorporate complex quantum mechanical information, which is crucial to accurately modelling the binding processes, and thereby obtain superior affinity predictions.

In order to achieve a similarly disruptive effect on models relevant to the pharmaceutical industry, the complexity of the molecular input data has to be captured, and compatible networks that effectively deal with such inputs need to be designed.

Section 2. Analysing Exponentially Large Search Spaces

In this section, we will re-frame the discussion of the GTN system in terms of analysing and searching exponentially large spaces, in particular the space of chemical compounds. As noted earlier, the GTN system analyses exponentially large search spaces using tensor networks.

Exponentially large search spaces typically suffer from the 'curse of dimensionality', in that as the number of dimensions increases, the volume of the space becomes extremely large. As such, the number of possible solutions may increase exponentially with the number of modes, making it impractical to analyse such search spaces experimentally.

Exponentially large spaces occur naturally in the context of quantum mechanics. In order to represent the physics of an n-particle system, one needs to in general work with vectors living in Hilbert spaces that are exponentially large in the number of particles. Thus, in analysing the search space of say small molecules, one is in general dealing with what could be described as "complexity within complexity": the number of possible molecules is astronomically large simply for combinatorial reasons, and in addition, the description of each of these molecules requires an analysis that uses vectors exponentially large in the number of particles.

The GTN system enables the search, sampling, statistical analysis and visualisation of large search spaces. The method utilises quantum physics inspired tensor networks (from hereon also referred to as tensorial spaces), in the context of generative machine learning models.

The manner in which tensor networks are incorporated into the GTN system can be classified as follows:

Using physics inspired tensor network decompositions within standard machine learning networks, for example to decompose RNNs (recurrent neural networks), convolutional neural networks, graph convolutional neural networks, fully connected layers neural networks, using physics decompositions such as MERA, tree tensor networks, correlated (described in arxiv.org/abs/1711.03357 and references therein). The context here is ML on classical data inputs that utilises tensor decompositions as a mathematical tool.

Using tensor networks in place of neural networks, as described here (arxiv.org/abs/1803.09780, arxiv.org/abs/1804.03680 and referees therein). The inputs here need to either be tensor networks themselves, or more generally mathematical objects living in an exponentially large Hilbert spaces. In order for such networks to be applicable to classical data, such as text or image data, it needs to be mapped into a high dimensional Hilbert space using an appropriate feature map. An advantage of this approach is that entanglement measures can be used to design the networks, given the structure of correlations in the training data—something that's virtually impossible with standard neural networks, due to explicit non-linear functions which are fundamental in their construction (sigmoid, ReLU, etc.).

Representing quantum mechanical data (molecules, crystals, or physical materials that require accurate quantum mechanical description to be accurately described more generally) using tensor network decompositions.

Using tensor networks to construct machine learning models, specifically so that they are able to optimally work on quantum mechanical input data (review: arxiv.org/abs/1306.2164).

Using tensor decompositions to represent and search through high-rank data, independently of any machine learning or deep learning model (as described here: arxiv.org/abs/1609.00893).

Running pure tensor network based machine learning models on quantum chipsets, by embedding the tensors networks into larger unitary matrices, and performing appropriate measurements (along the lines of methods described here: arxiv.org/abs/1804.03680)

We can generalise the GTN system to a system that analyses exponentially large search spaces using tensor networks.

The GTN system analyses a chemical compound dataset (where the data is either obtained from real world measurements or generated synthetically) so as to determine suitable candidate chemical compounds. The GTN system undertakes the following steps: determining a tensorial space for said chemical compound dataset; correlating the tensorial space with a latent space (and this latent space may itself be a tensor network); and outputting a further dataset, the further dataset comprising a filtered dataset and/or a set of novel chemical compounds (i.e. those not in the original dataset) of candidate chemical compounds. As described above in more detail, tensorial methods could be used here to represent a high rank classical dataset, e.g. graph objects with high rank per-atom descriptors, data living in a multi-dimensional space, or the raw wavefunctions themselves described using tensor networks, and could be used to construct the machine learning network.

Optionally, the tensorial space is a wavefunction space. The latent space may represent physically relevant wavefunctions and/or desired properties of candidate chemical compounds. The latent space may represent a relevant physical operator decomposed as a tensor network.

The further dataset of candidate chemical compounds may be a filtered dataset of candidate chemical compounds and/or a novel dataset of candidate chemical compounds.

The wavefunction space may be monitored by a tensor network, which may be one of: complete-graph tensor network state, correlator product state, projected entanglement pair states (PEPS), matrix product states (MPS)/tensor train, and matrix product operator, MERA, or any other type of tensor network or equivalent or generally similar or otherwise useful mathematical object.

The GTN system implements a method that may further comprise mapping the dataset into a higher dimensional tensor. Correlating the tensorial space with a latent space may comprise tensor decomposition or determining an optimal tensor network to describe the mapping of the input data set to a more general description (e.g. that of a molecular wavefunction), and/or maximising a cost function, said cost function representing desirable properties of said candidate chemical compounds. Predictive models are also used in the GTN system (see earlier).

Correlating the tensorial space with a latent space may comprise optimising over the latent space (with respect to outputs of predictive models, or similarity with respect to a set of target molecules—e.g. using the Tanimoto index, or other metric)—for example so that it represents desirable properties of said candidate chemical compounds. This can be done in the context of GAN or VAE generative models, with or without the aforementioned tensor network extensions).

Thus, the GTN system uses a suite of models that utilises tensorial decompositions in various forms described above.

Determining the tensorial space for the chemical compounds dataset may comprise encoding the dataset using a generative model, and outputting may comprise decoding using a generative model. The generative model may comprise an (artificial) neural network, which may be in the form of e.g. a generative auto encoder, RNN, GAN, Monte-Carlo tree search model, an Ising model or a restricted Boltzmann machine trained in an unsupervised manner etc. (see openreview.net/pdf?id=Bk0xiI1Dz, arxiv.org/abs/1710.07831, and references therein). The neural network may comprise tensorial decompositions or tensor networks (in particular, a tensor network comprising a tensorial generative autoencoder), or may be constructed as a tensor network in its entirety. The tensor network could be a quantum circuit, which could potentially be run on a quantum computer (see arxiv.org/abs/1804.03680).

The method implemented by the GTN system may further comprise outputting a visualisation of the tensorial space (using eigenvalue decompositions, non-linear projections to small and easily visualisable low dimensional manifolds described by tensor network spaces—as described here: arxiv.org/abs/1210.7710).

The candidate chemical compounds may be active elements of a pharmaceutical compound, and/or may be suitable for use in an organic light emitting diode, or any other commercially useful outcome. The chemical compound dataset may be a dataset of possible molecules containing up to a predetermined maximum number of atoms.

We can think of the GTN system as a system for analysing a chemical compound dataset so as to determine suitable candidate chemical compounds, the system comprising: means for receiving a chemical compound dataset; a processor for processing the chemical compound dataset to determine a tensorial space for said chemical compound dataset; a processor for correlating said tensorial space with a latent space; and means for outputting a further dataset of candidate chemical compounds.

We can also think of the GTN system as implementing a method of analysing a dataset so as to determine suitable candidate data points, the method comprising: determining a tensorial space for the dataset; correlating the tensorial space with a latent space; and by optimising over the latent space, outputting a further dataset, the further dataset comprising a filtered dataset and/or a set of novel data points (i.e. those not in the original dataset) of candidate data points (which may be referred to as 'candidate targets').

A generalization is to think of the GTN system as a method of filtering a molecule dataset so as to determine suitable candidate molecules, the method comprising: determining a tensorial space for the molecule dataset; correlating the tensorial space with a latent space, the latent space being used to output physically relevant wavefunctions; and outputting a filtered dataset of candidate molecules.

Another generalization includes a method of using a tensorial generative autoencoder to determine suitable candidate molecules from a dataset.

The GTN system implements a method of restricting a multi-modal search space within a molecule dataset, comprising: representing the molecule dataset in terms of a tensor network; calculating the entanglement entropy using quantum physics methods (for example, as shown in Roman Orus, *A practical introduction to tensor networks: Matrix product states and projected entangled pair states, Annals of Physics, Volume* 349, p. 117-158) indicative of the correlations in the dataset; and finding an optimal tensor network to capture the amount of entanglement entropy in the dataset (preferably, wherein the term 'optimal' means that the maximal amount of entanglement that can be captured by such a tensor network is close to the actual amount necessary to capture the correlations in the data).

We have noted above that the GTN system enables the search and optimization in large data spaces, and the generation of new hitherto unseen elements via a tensorial generative autoencoder. An example is a space of all possible molecules containing up to a certain maximum number of atoms. The GTN system is designed in particular to analyse spaces plagued by the curse of dimensionality, or equivalently where the data is naturally expressed in terms of tensors (or multi-dimensional arrays) with a large number of modes. In such problems the number of possibilities grows exponentially with the number of modes, e.g. in the present example the number of possible molecules grows exponentially with the number of constituent atoms, and the vector needed to describe the molecular wave function is in general exponentially large for each molecule. The GTN system bypasses the 'curse of dimensionality' by utilizing quantum physics inspired tensor decompositions, which may be constructed in a manner such that the number of parameters grows polynomially in the number of constituents (e.g. atoms or electrons).

In practice the number of such constituents is often of the order of a few hundreds, and by imposing symmetries even much larger systems can be described (including infinitely large systems, by imposing e.g. translation invariance, as described in "*Variational optimization algorithms for uniform matrix product states*", V. Zauner-Stauber, L. Vanderstraeten, M. T. Fishman, F. Verstraete, J. Haegeman, arXiv: 1701.07035). Tensor networks enable intelligent priors to be picked that, in turn, restrict the search to the space of physically relevant elements (e.g. electron configurations that occur in synthesizable molecules, as opposed to arbitrary wave-functions). The GTN system utilizes these decompositions both by (optionally) applying an appropriate feature map to the input data, and by applying tensor network decompositions in the latent space of the generative autoencoder.

Examples of suitable tensor networks include Complete-Graph Tensor Network States or Correlator Product States, which have been shown to provide extremely accurate description of electron wave functions in molecules, but also multi-scale entanglement renormalization ansatz (MERA), matrix product states, or tree tensor networks for molecular and other types of data. Matrix product states (DMRG), and tree tensor networks have been used widely for quantum chemistry (see e.g. arxiv.org/abs/1405.1225 and references therein).

Such priors may be picked by considering the details of the physics under study. For example, the theoretical analysis of local massive Hamiltonians has demonstrated that the entanglement entropy of grounds states of such Hamiltonians increases as the area of the boundary of the region under study. Matrix product states (MPS), or projected entanglement pair states (PEPS) in more than one spatial dimension, are designed with these entanglement properties built in, and are thus the suitable tensor networks to study such ground states. MERA tensor networks provide the optimal description for ground states in the massless limit, that is, for critical, or (equivalently) scale-invariant systems. The general structure of correlations of electrons in a molecule is captured by the aforementioned Complete-Graph Tensor network states. As a further example, tree tensor networks have been shown to capture correlations of image data well, and to be closely related to convolutional neural nets with non-overlapping filters (see Levine, Yoav; Yakira, David; Cohen, Nadav; Shashua, Amnon, *Deep Learning and Quantum Entanglement: Fundamental Connections with Implications to Network Design*, eprint arXiv:1704.01552). The present invention may make use of techniques which capture the correlations in the data as closely as possible.

In the GTN system, we see an optimization with respect to the tensorial space, which can refer to either the space resulting from the feature map of the inputs, or to the latent space (or both). Controlled optimization (a tailored search) is performed in the tensorial space with respect to complex cost functions that quantify the desirable properties, which are to be maximized (or minimized, as appropriate) over the search space. The cost function can be a complex function of the outputs of the tensorial autoencoder. For example, the output may be a tensorial description of the quantum state of the molecule, and one may optimise with respect to complex correlation functions calculated from this output tensor network (using standard physics methods, see Roman Orus, *A practical introduction to tensor networks: Matrix product states and projected entangled pair states, Annals of Physics*, Volume 349, p. 117-158))

The GTN system enables the visualization of the high dimensional space with the aim of e.g. (but not restricted to) understanding the neighbourhood of a known point in order to find optimal nearby elements, visualizing projections onto subspaces (sub-manifolds) of the tensorial space, that aids the understanding of which parts of (and directions in) the latent space are the most relevant for the optimization. Examples of visualization techniques include (but are not limited to) projections onto smaller tensorial latent spaces that are more readily visualized, understanding of entanglement entropy (described in Roman Orus, *A practical introduction to tensor networks: Matrix product states and projected entangled pair states, Annals of Physics*, Volume 349, p. 117-158) or separation rank (described in Levine, Yoav; Yakira, David; Cohen, Nadav; Shashua, Amnon, *Deep Learning and Quantum Entanglement: Fundamental Connections with Implications to Network Design*, eprint arXiv: 1704.01552) to visualize correlations and optimize the network architecture, visualization via higher order correlation functions and spectra of density matrices and correlation matrices (described in Stojevic, Vid; Haegeman, Jutho; McCulloch, I. P.; Tagliacozzo, Luca; Verstraete, Frank, *Conformal data from finite entanglement scaling, Physical Review B*, Volume 91, Issue 3, id.035120), visualisation of tangent directions to the manifold of tensor network states in order to determine for example the best directions for the optimisation of a given quantity of interest (as described in *Post-matrix product state methods: To tangent space and beyond*, Haegeman, Jutho; Osborne, Tobias J.; Verstraete, Frank, *Physical Review B*, vol. 88, Issue 7, id. 075133).

The GTN system aims to find an optimal final product that is composed of a large number of constituents (for example an alloy composed of individual constituent metals, a food supplement or a cosmetic product composed of a large number of ingredients). In such a scenario it is assumed that the number of constituents is large enough so that an exhaustive experimental search is not possible due to the 'curse of dimensionality', and the dataset of final products with experimentally measured properties of interest (which are capable of being optimised) is an exponentially small subset of all possible final products. The tensor network used to represent interesting regions of the exponentially large space needs to be determined using an intelligent prior based on available data.

Figure 4:
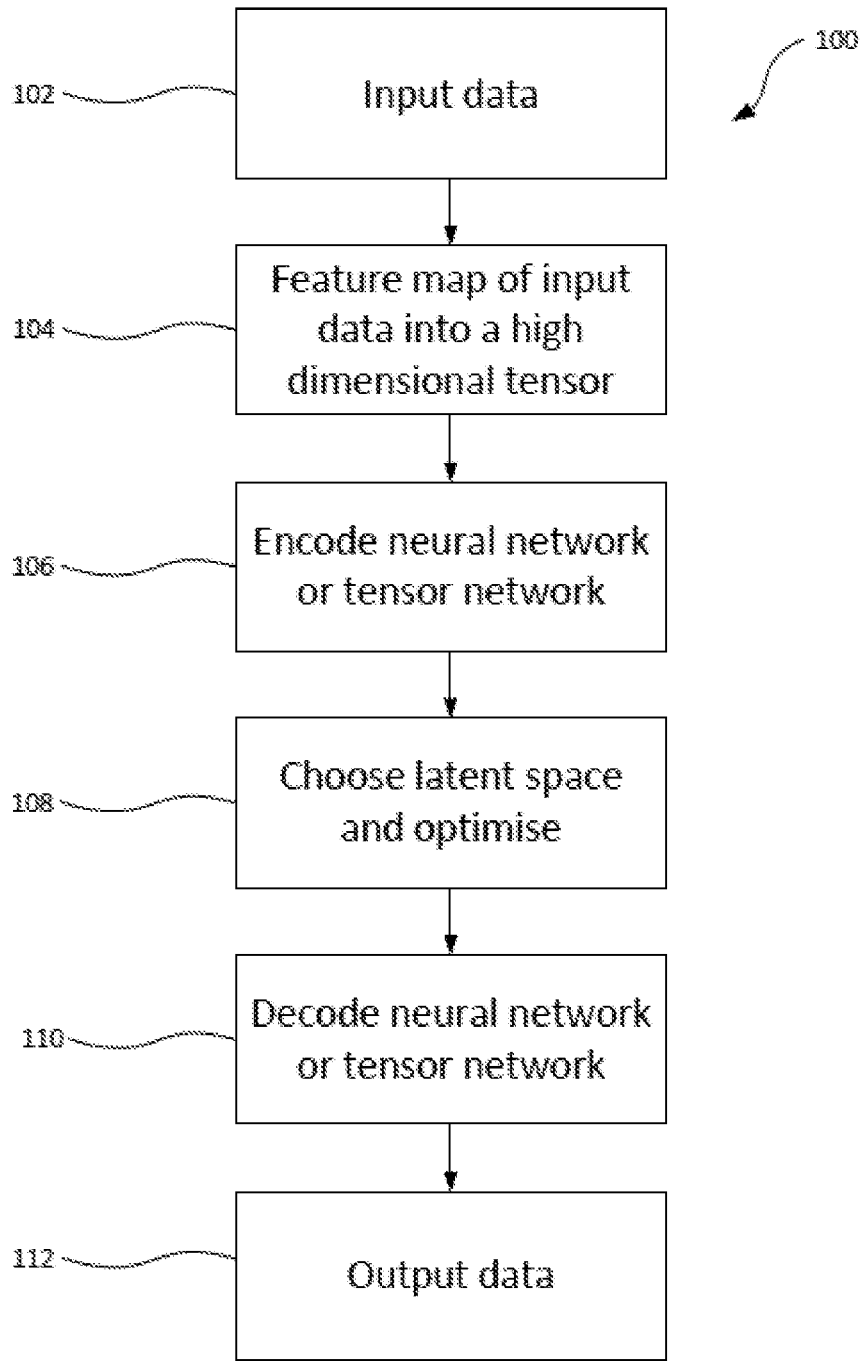
FIG. 4 shows flow diagram of a method of filtering a molecule dataset.

FIG. 4 is a flow diagram of a method 100 of applying a tensorial autoencoder to a dataset. There are two distinct optimisations: the first optimisation corresponding to training the autoencoder, where the cost function aims to, roughly speaking, minimise the difference between the outputs and in input whilst also minimising the amount of information that needs to be passed through the latent space (utilising any of the standard cost measures for this difference, see for example *Tutorial on Variational Autoencoders*, Doersch, Carl, arXiv:1606.05908). Specific steps for the autoencoder optimisation are as follows.

In an initial step 102, input is received. The input data comprises a string, vector, matrix, or higher dimensional array (i.e. a tensor).

In a second step 104, a feature map is applied to the input data to transform it into a high dimensional structure, with the number of modes equal to the number of input data points. This step is optional, and may not be performed if the input data is already a high dimensional tensor. A suitable feature map is shown in Miles Stoudenmire, E.; Schwab, David J., *Supervised Learning with Quantum-Inspired Tensor Networks, Advances in Neural Information Processing Systems* 29, 4799 (2016)

In a third step 106, the data is encoded using a neural network (or optionally a tensor network), in particular an autoencoder.

In a fourth step 108, a latent space, expressed as a tensor network, is chosen to fit the problem under investigation. In the case of a molecule dataset, complete-graph tensor network latent spaces (shown in Marti, Konrad H.; Bauer, Bela; Reiher, Markus; Troyer, Matthias; Verstraete, Frank, *Complete-graph tensor network states: a new fermionic wave function ansatz for molecules, New Journal of Physics*, Volume 12, Issue 10, article id. 103008, 16 pp. (2010)) or correlator product state latent spaces (shown in Vid Stojevic, Philip Crowley, Tanja Đurić, Callum Grey, Andrew Green, *Time evolution and deterministic optimization of correlator product states, Physical Review B*, Volume 94, Issue 16, id.165135) may be used, both of which show accurate descriptions of electron wave functions in molecules. Matrix product states, and tree tensor networks often give very accurate descriptions of molecular electron wavefunctions (see arxiv.org/abs/1801.09998 and references therein)

In a fifth step 110, the data is decoded using the neural network (or tensor data).

In a sixth step 112, output data is produced, in the form of a string, vector, matrix, tensor, or a tensor network.

Figure 5:
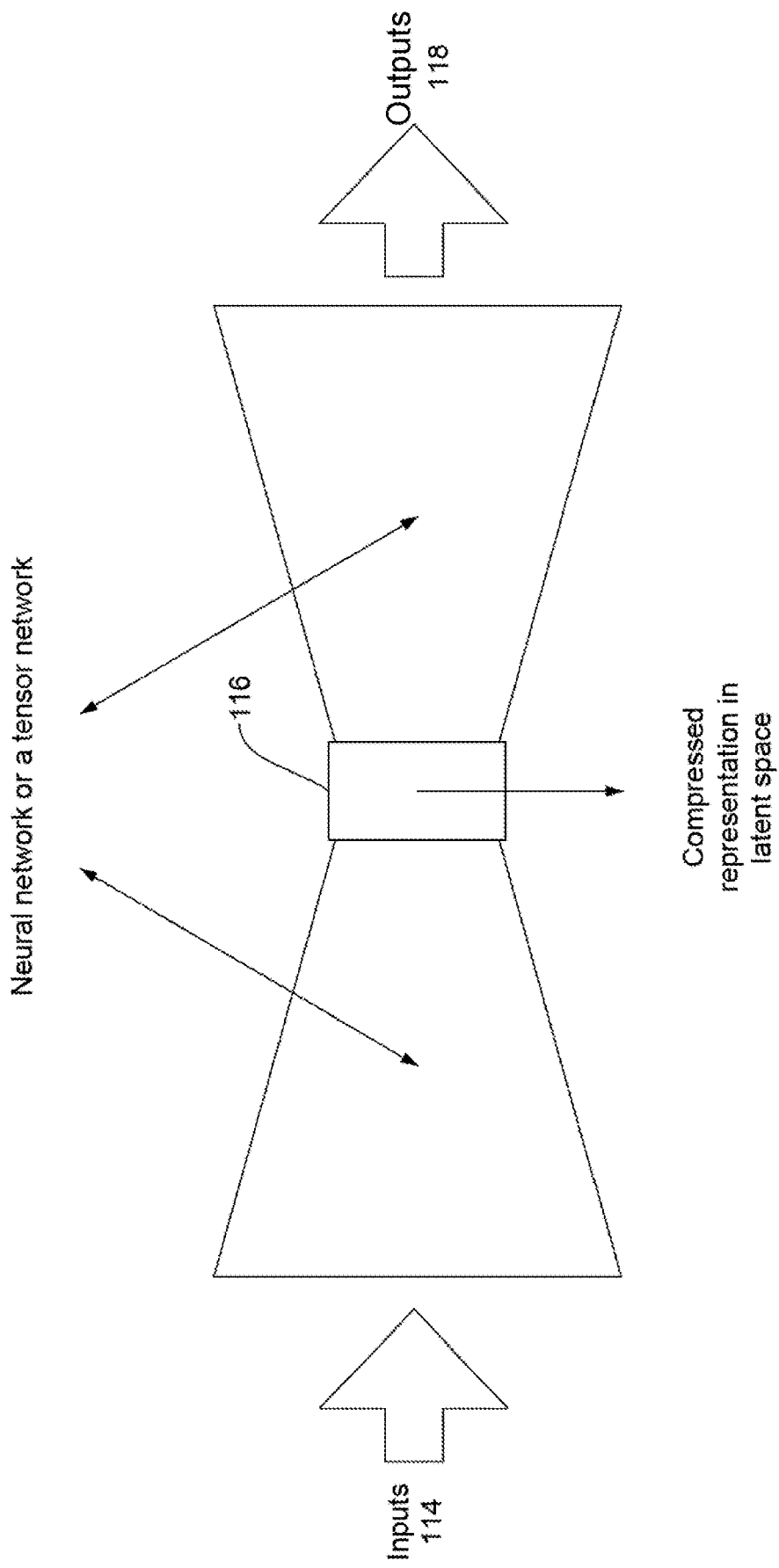
FIG. 5 shows a schematic diagram showing how data is processed to train an autoencoder.

FIG. 5 is a schematic diagram showing how data is processed in the method 100 to train the autoencoder. Input data 114 is encoded into a chosen latent space 116 using a neural network or tensor network. The compressed representation of the data in the latent space is then decoded using the neural network or tensor network, thereby producing outputs 118. The weights in the neural network, or constituent tensors in a tensor network, are optimised to minimise the difference between outputs 118 and inputs 114.

In one embodiment, input data in the form of a tensor is received. A tensor network provided as an autoencoder is used to encode the input data into a complete-graph tensor network latent space. The tensor network is then used to decode the data in the latent space, producing an output also in the form of a tensor.

A second possible optimisation aims to determine an optimum in the latent space with respect to a cost function representing some desired property. For example, the desired properties may comprise water-octanol partition coefficient in drug design (or can be any of the descriptors listed in for example *Quantitative Structure Activity Relationship (QSAR) Models of Mutagens and Carcinogens*, Romualdo Benigni, CRC Press, 26 Feb. 2003, or other standard quantum mechanical quantities that one can calculate directly from the molecular wavefunction). Depending on details of the steps described above, the latent space might be a tensorial object, or a simple vector (which is the usual setup in an autoencoder), or some other mathematical construct such as a graph. The output determined by a given element of the latent space (and in particular the optimal element of the latent space) will in general not be a part of the original dataset. For this reason the approach is termed 'generative', and the novel elements may lie anywhere in an exponentially large space. In particular, in the context of searching through spaces of possible chemical compounds, which is exponentially large in the number of constituent atoms in the compound, the generative tensorial approach described here will explore regions of the huge space of possible compounds not accessible to other methods. The output data may alternatively or additionally be a filtered version of the input data, corresponding to a smaller number of data points.

Figure 6:
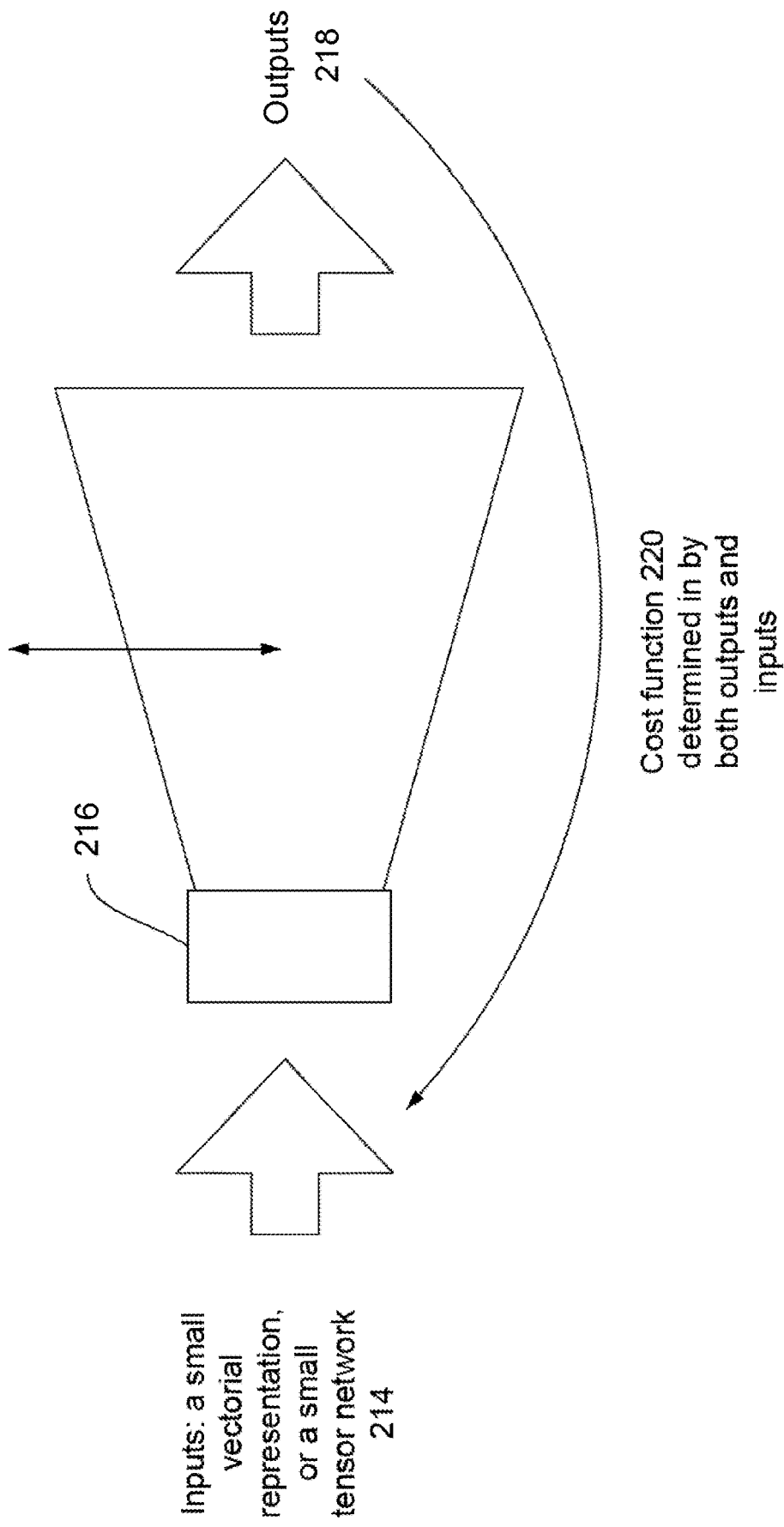
FIG. 6 shows a schematic diagram showing how data is processed to determine an optimum in the latent space.

FIG. 6 is a schematic diagram showing how data is processed to determine an optimum in the latent space. Inputs 214 (in the form of a small vectorial representation or a small tensor network) are applied to a chosen latent state 216. The neural network or tensor network (determined by the particular optimisation of the autoencoder, as shown in FIG. 2) is applied to the elements in the latent space to produce outputs 218. The inputs are optimised by minimising (or maximising, as appropriate) a cost function 220.

In one embodiment, a tensor representing a space of possible chemical compounds is applied to a complete-graph tensor network latent space. A tensor network arranged to find an optimum with respect to the water-octanol partition coefficient of a compound is then applied to the latent space, generating an output in the form of a dataset of novel chemical compounds (represented as a tensor).

Figure 7A:
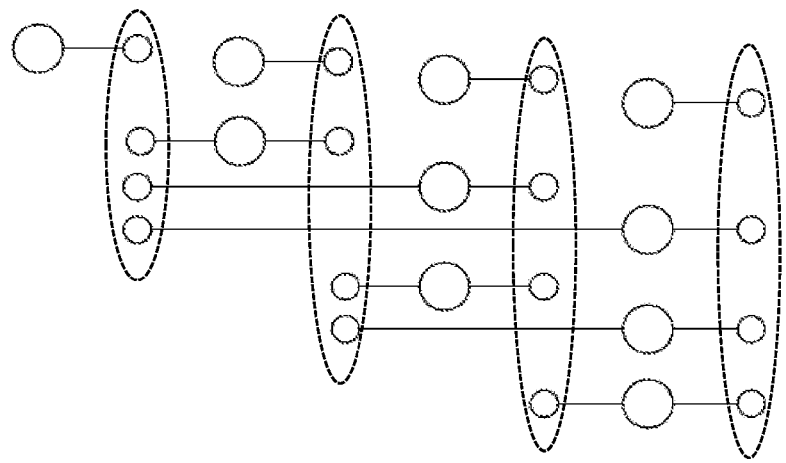
FIG. 7 show schematic representations of suitable tensor networks for use with the method.
Figure 7B:
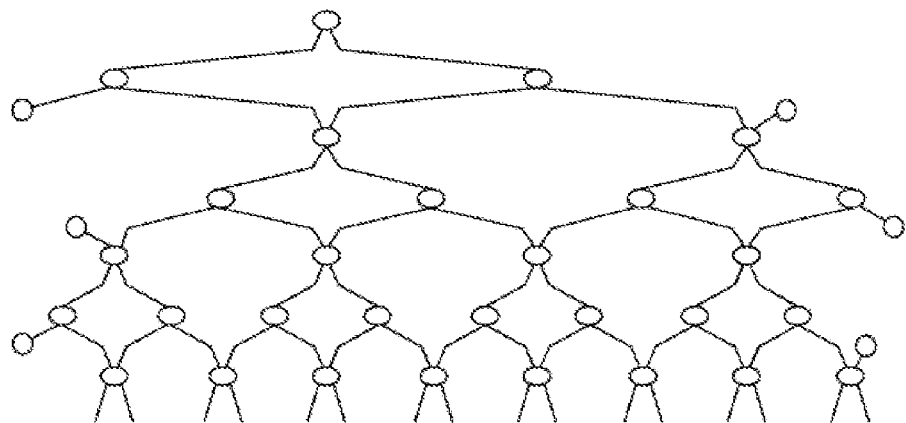
Figure 7C:
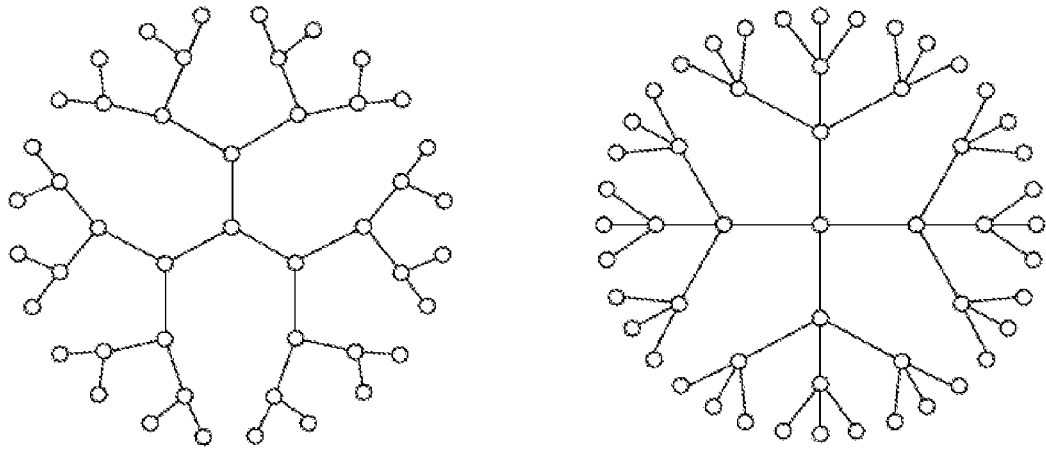

FIGS. 7*a-c* show schematic representations of suitable tensor networks for use with the method 100. FIG. 4*a* shows a schematic representation of a complete graph tensor network state (CGTN) (from Vid Stojevic, Philip Crowley, Tanja Đurić, Callum Grey, Andrew Green, *Time evolution and deterministic optimization of correlator product states, Physical Review B*, Volume 94, Issue 16, id.165135), which also corresponds to a specific restricted type of a correlator product state. Circles and dotted ovals represent different kinds of tensorial mappings. As mentioned, both of these tensor networks show accurate descriptions of electron wave functions in molecules. FIG. 4*b* shows a schematic representation of the MERA tensor network (from "Tensor Network States and Geometry", Evenby, G.; Vidal, G.; *Journal of Statistical Physics*, Volume 145, Issue 4, pp. 891-918) which may provide an optimal description for ground states in the massless limit. FIG. 4*c* shows schematic representations of tree tensor networks (from "*Efficient tree tensor network states (TTNS) for quantum chemistry; Generalizations of the density matrix renormalization group algorithm*", Nakatani, Naoki; Chan, Garnet Kin-Lic, *Journal of*

*Chemical Physics*, Volume 138, Issue 13, pp. 134113-134113-14 (2013)), which capture correlations of image data well.

FIG. 8 is a diagram showing an example of a decomposition of a tensor into a matrix product state. Such an operation is performed in the fourth step 108 of the method 100. The matrix product state shown is also known as a 'tensor train'. Examples of possible decompositions are shown in Roman Orus, *A practical introduction to tensor networks: Matrix product states and projected entangled pair states, Annals of Physics*, Volume 349, p. 117-158 and Cichocki, A.; Lee, N.; Oseledets, I. V.; Phan, A-H.; Zhao, P.; Mandic, D., *Low-Rank Tensor Networks for Dimensionality Reduction and Large-Scale Optimization Problems: Perspectives and Challenges*, eprint arXiv:1609.00893.

d is the size of each of the modes of the order N tensor $\Psi$ (which is assumed to be the same for all modes in this case, however, this need not be the case. For every value of $i_n$, $A^{i_n}$ is a d×d matrix.

FIG. 9 shows a schematic decomposition of a mode-5 tensor as a matrix product state (or 'tensor train').

Figure 10:
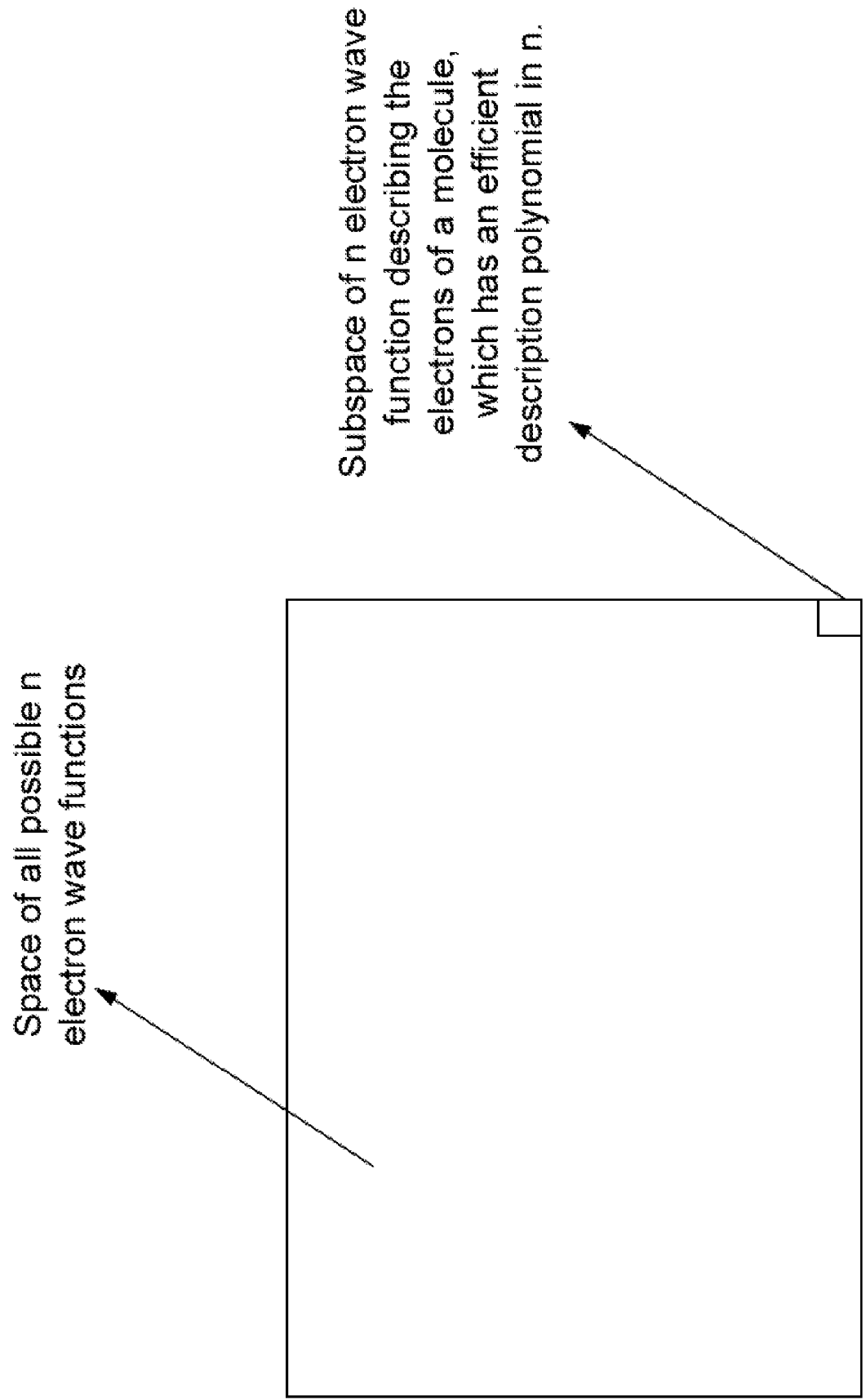
FIG. 10 shows a schematic drawing depicting the effect of a quantum physics tensor decomposition.

FIG. 10 is a schematic drawing depicting the effect of a quantum physics tensor decomposition, reducing a state that is exponentially expensive, in the number of modes, to store and manipulate, to one which imposes a prior and whose representation is polynomial in the number of modes. The exponentially expensive state forms part of the 'curse of dimensionality', in that the size of the quantum wave function is exponential in the number of particles.

APPENDIX 1

Re-Statement of Core Concepts

We will start with schematic illustrations FIG. 16-21.

Figure 16:
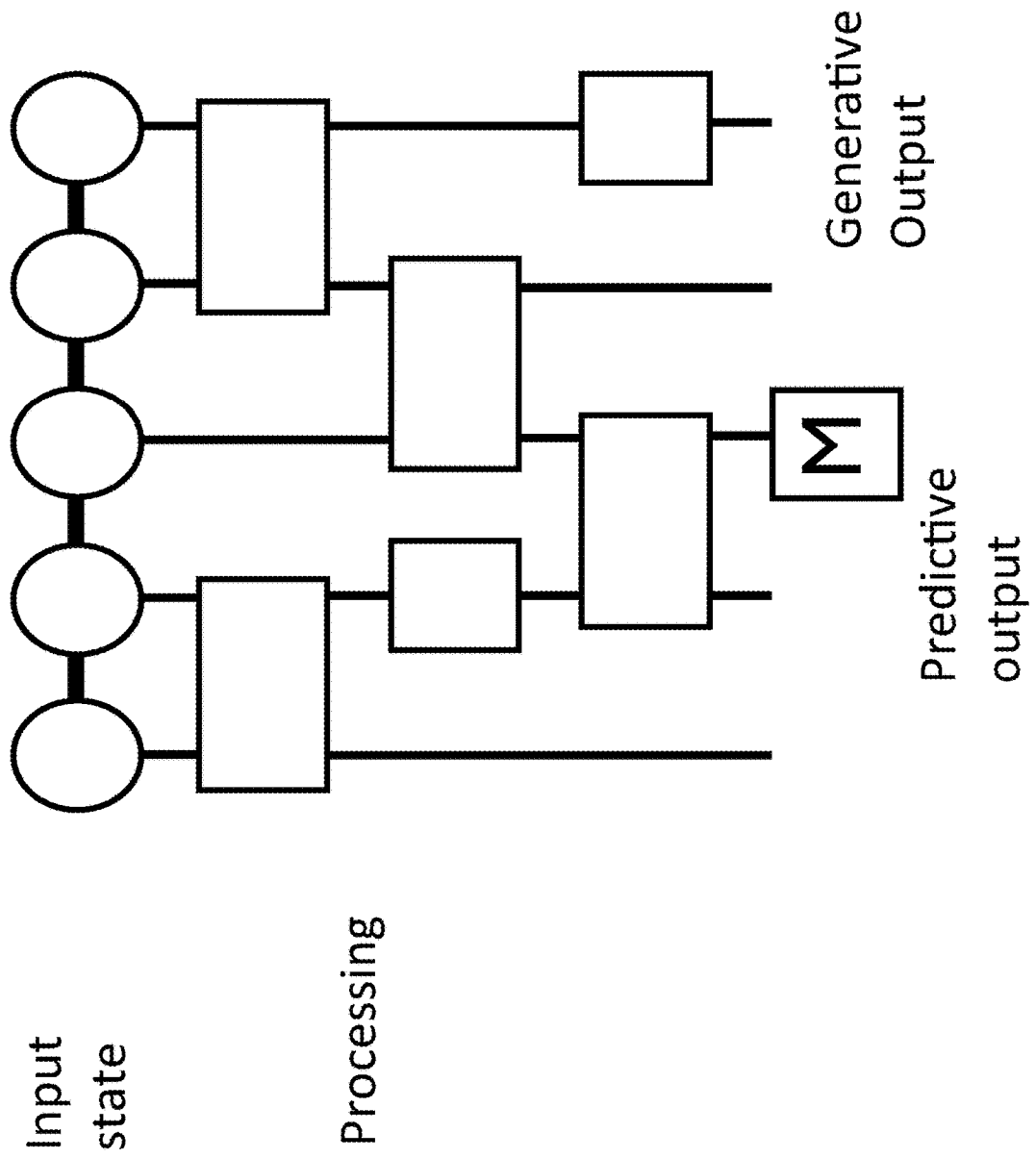
FIG. 16 schematically represents processing tensor network input states to produce a predictive output and a generative output.

FIG. 16 shows an Input state: a general tensor network state—in this example a matrix product state. In the Processing stage, the input is processed by a general tensor network (or, in full generality, a neural network/tensor network hybrid)—in this example a quantum circuit consisting of 1- and 2-qubit unitary gates. If the transformation is to be computable classically, every contraction in the tensor network has to be storable as an efficiently computable tensor network state. The quantum circuit example might constitute a feasible computation only on a quantum chipset.

The Processing stage outputs a Predictive output: in order to obtain a regression or classification output, one can perform a quantum measurement on a desired number of qubits, specified by M here, (this can be a real quantum measurement, or a classically simulated version thereof, see arxiv: 1804.03680), or, classically, pass a subset from the output layer, through an e.g. fully connected set of neural network layers, or e.g. a softmax classifier.

Generative Output: the circuit can itself generate samples. Or, classically, the output vector (or an element of some vector subspace thereof), can be used to reproduce the input via a decoder network, in e.g. a variational autoencoder setting.

Figure 17:
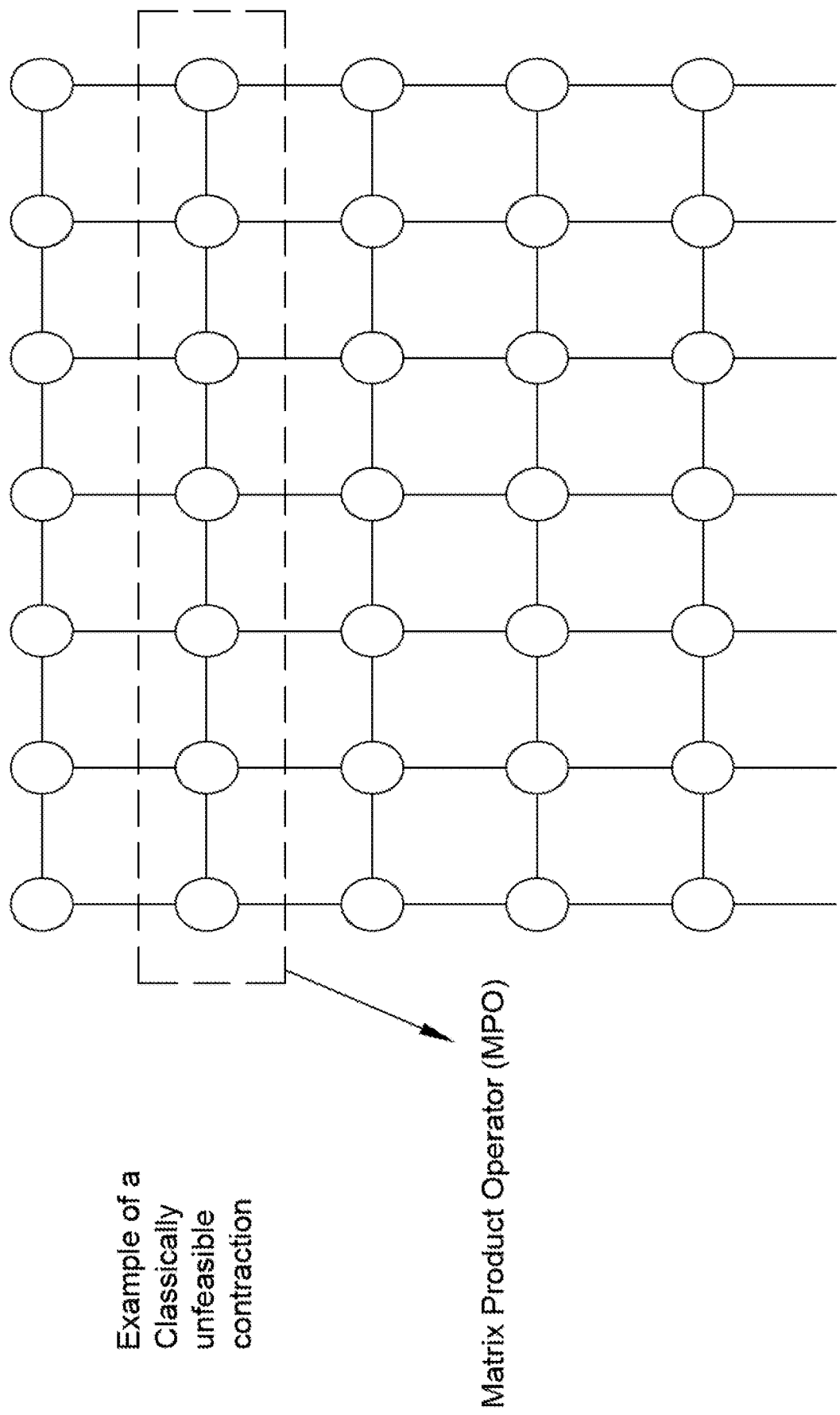
FIG. 17 schematically represents a tensor network of matric product operators.

FIG. 17 is an example of a classically unfeasible contraction: following on from FIG. 16, this is an example of an application of a tensor network of N matrix product operators (MPOs) (in this diagram 4) to an input MPS in succession. This contraction is in general exponential in N. For example, the naive matrix product bond dimension, of the result of the MPO applied to the initial MPS is $D^{(N+1)}$. For a classical contraction of this network to be feasible in general, one therefore has to apply an approximation scheme, for example, a projection to a lower dimensional MPS after every application of an MPO. If the approximation scheme is sufficiently accurate, a classical scheme is possible, otherwise, for a class of MPOs that can be mapped to a quantum circuit, a quantum computing solution becomes necessary. Methods for projecting to smaller MPS, using e.g. singular value decomposition are described here arxiv.org/abs/1306.2164, and in cited references.

Figure 18:
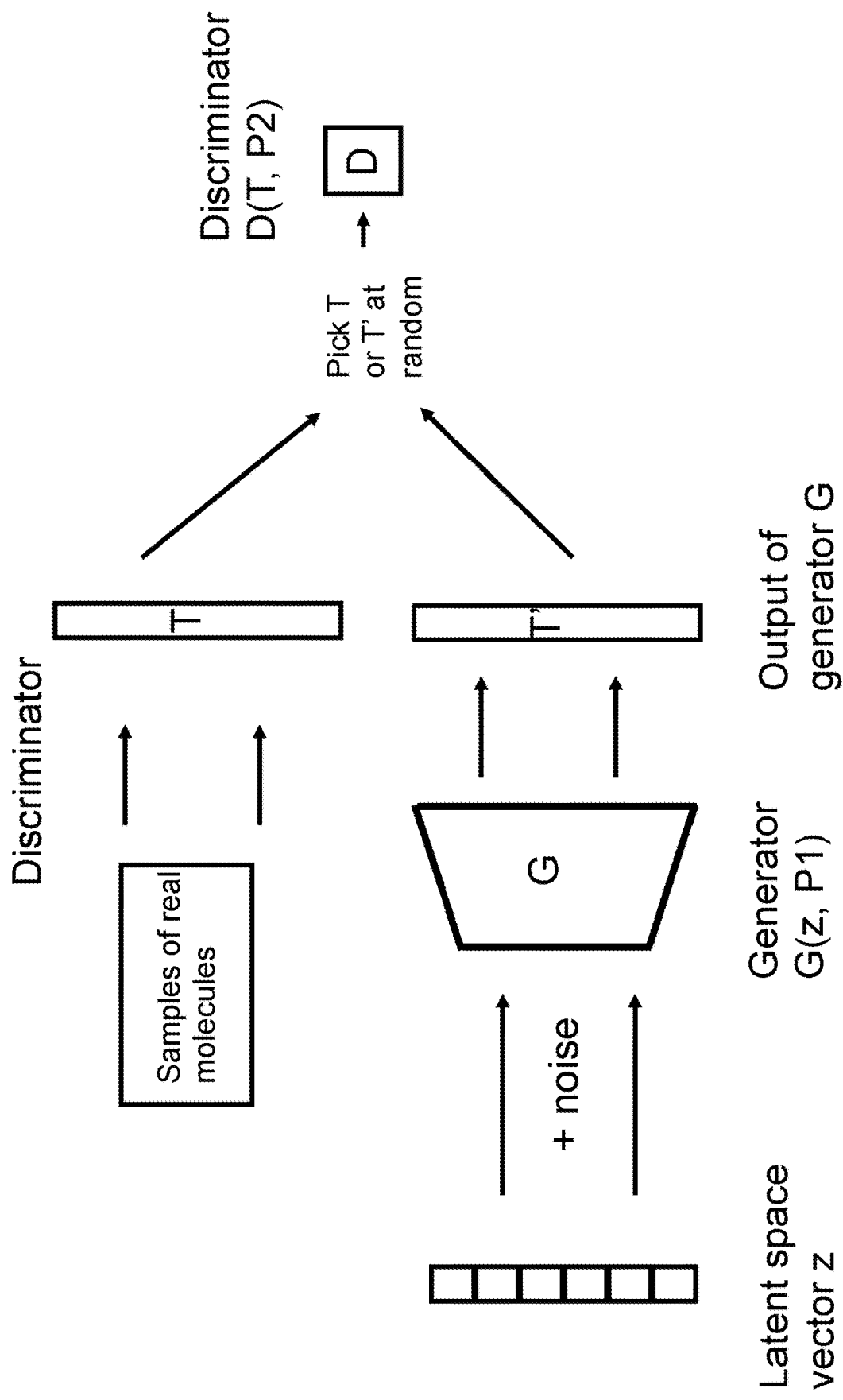
FIG. 18 schematically represents the overall scheme of tensor networks outputting to a generative adversarial network.

In FIG. 18 we show the overall schematic for a generative tensorial adversarial network. For the top limb, samples of real molecules are fed to Discriminator D; molecules are represented as tensor networks T, using quantum mechanics/quantum chemistry methods.

For the lower limb, we start with latent space vector z: traditionally a small dimensional vector (small compared to the dimensionality of the data), but can itself be represented by a 'small' tensor network, is combined with noise and fed to Generator G(z, P1)—in general a neural network/tensor network hybrid, taking z as input, and a function of internal tensors/weight matrices P1. The output of generator G: in general the generator G outputs a tensor network T' description of a molecule.

The system picks T or T' at random and then discriminator D(T, P2) decides whether T/T' is a 'real' or a 'fake' sample. Discriminator network contains internal tensor/weight matrix parameters P2.

Training is a min-max game: Maximise D(T), and minimise D(T') for P2, and maximise D(T') for P1. For details on GANs in general, see medium.com/ai-society/gans-from-scratch-1-a-deep-introduction-with-code-in-pytorch-and-tensorflow-cb03cdcdba0f and references therein.

Figure 19:
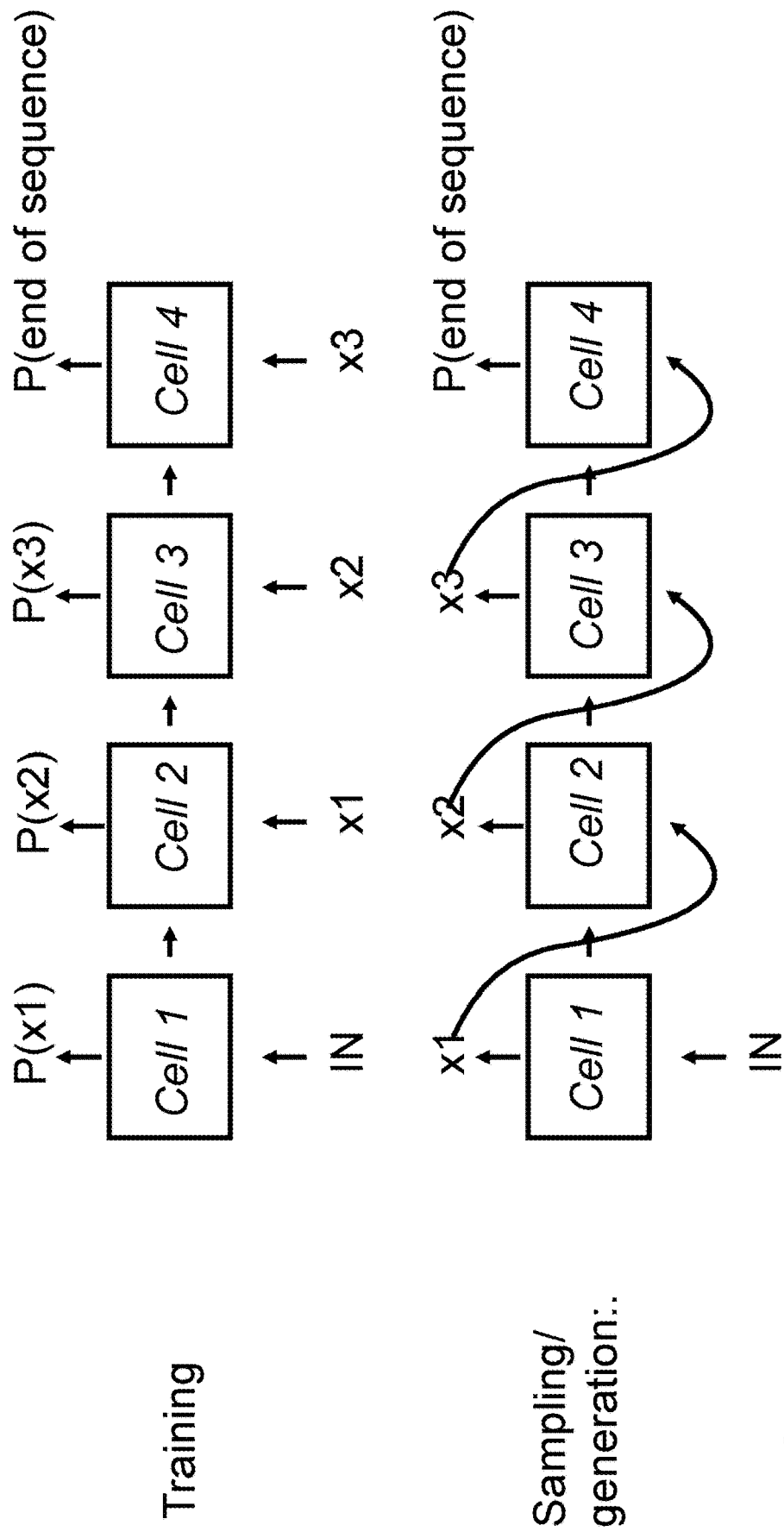
FIG. 19 schematically represents a RNN generative model.

In FIG. 19, we have a schematic of a RNN generative model. The standard RNN approach works on sequences, and is not straightforwardly amenable to working on tensor network data, which is not generally sequential. Nevertheless, a general tensorial RNN can be composed in a manner where each cell is built up from any of the listed combinations of neural networks/tensor networks. A generalised RNN can be trained to predict a sequence of tensors in a linear tensor network.

The system trains the model on sequences (here: {x1, x2, x3, eos}, to predict the next element of a sequence.

Sampling/generation: initialised randomly at IN, the outputs of the model are fed into the next cell along, until EOS (end of sequence) is reached.

Figure 20:
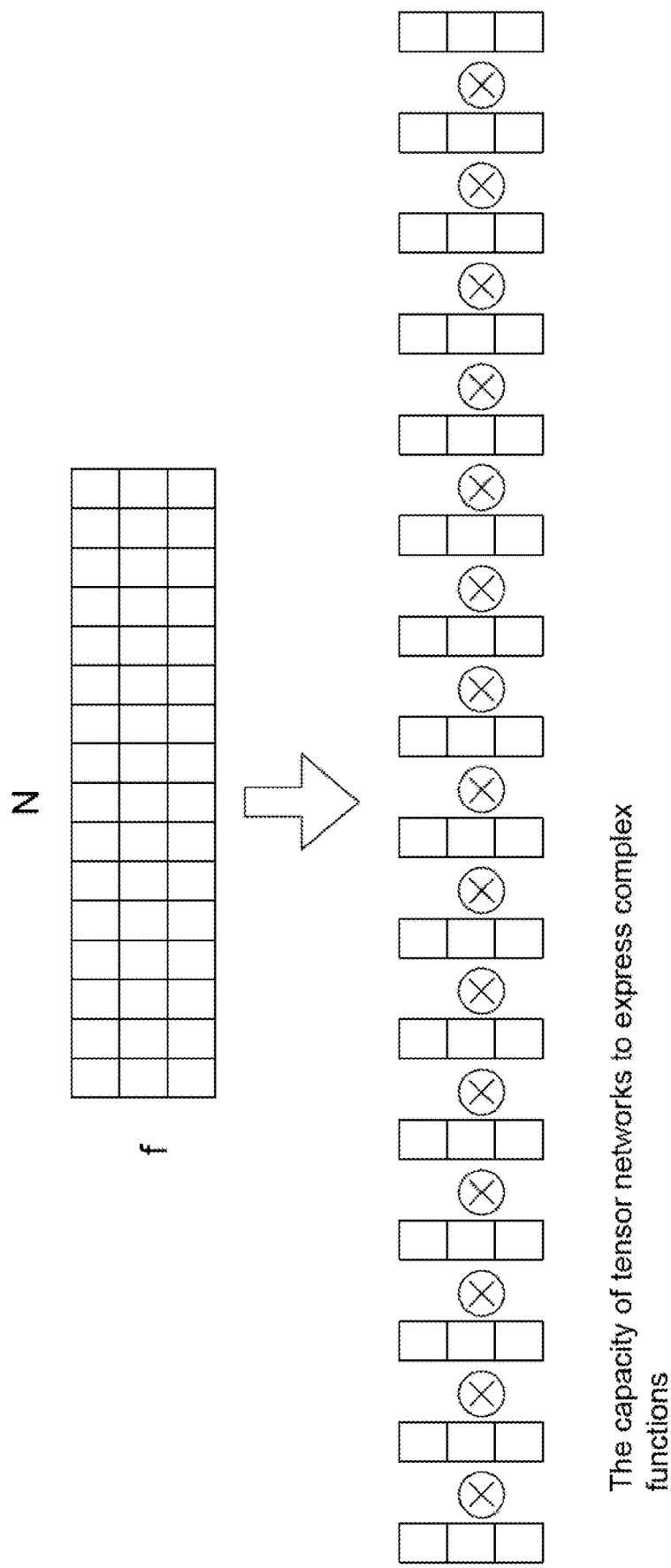
FIG. 20 schematically represents the capacity of tensor networks to express complex functions.

In FIG. 20, we show the capacity of tensor networks to express complex functions. Classical data is represented by a small rank tensor: in this example a matrix of dimensions f×N. This data is first mapped into a huge Hilbert space, in this example by taking a tensor product of all the individual f×1 vectors in the data matrix. The size of this object is $f^N$. Tensor networks are constructs involving multi-linear operations, meaning that the reconstruction of the original high rank tensor is obtained by contractions. Unlike for neural networks, there are no explicit applications of non-linear functions (such as ReLU or sigmoid functions). The power of tensor networks lies in the fact that these multi-linear operations are applied in an exponentially large Hilbert space (see e.g. arxiv.org/abs/1803.09780 for an explanation of an aspect of these ideas), as a trade-off for an explicit non-linearity. Whilst classical data needs this somewhat artificial feature map in order to be inputted into tensor networks, quantum data is naturally expressed in terms of high rank tensors, and associated tensor networks (see arxiv.org/abs/1306.2164 and references therein).

Figure 21:
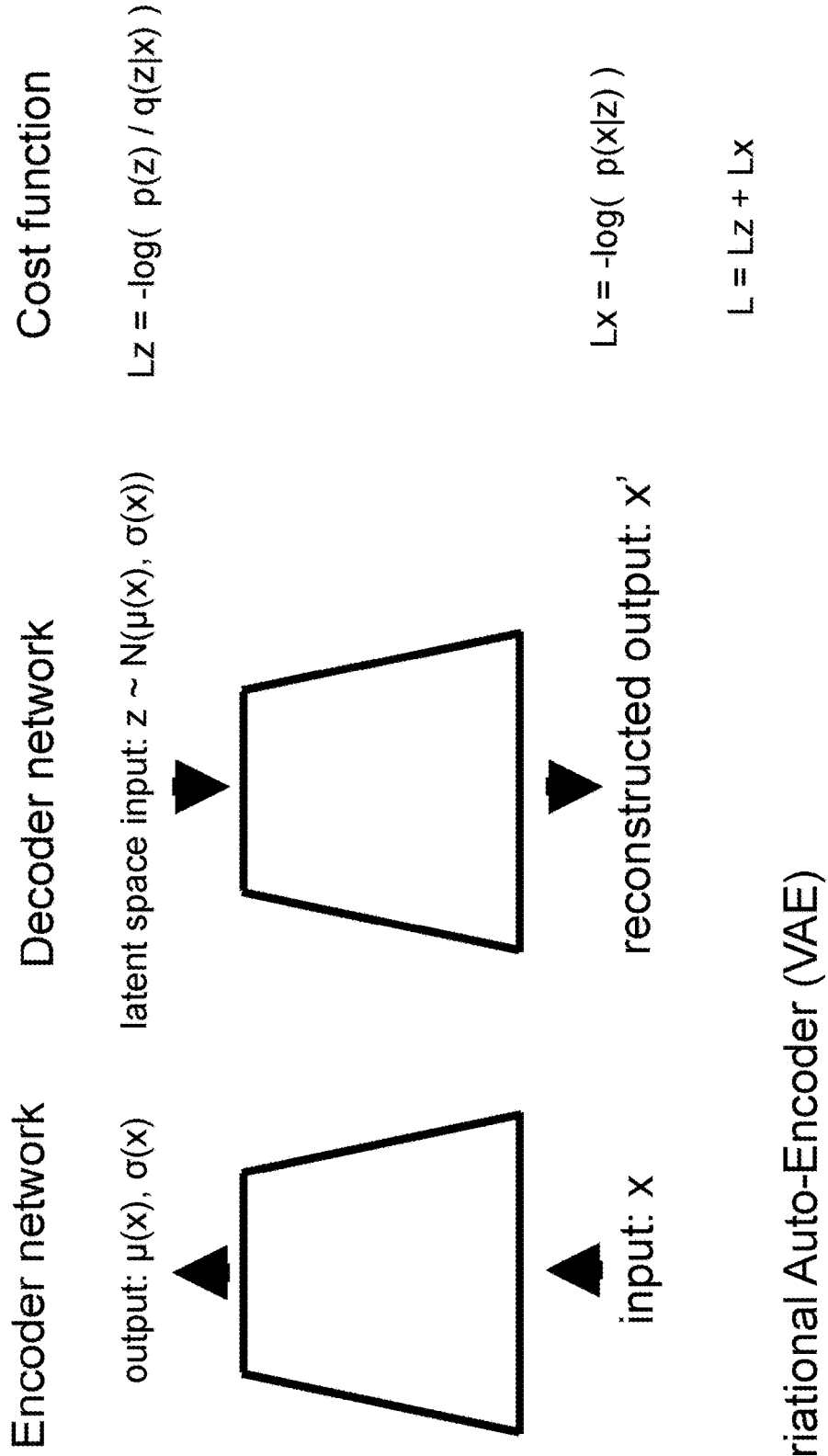
FIG. 21 schematically represents a variational auto-encoder.

In FIG. 21, we show the operation of a Variational Auto-Encoder (VAE): The standard VAE first encodes an input x into a set of latent variables $\mu(x)$, $\sigma(x)$. The decoder network samples the latent space from a prior distribution p(z), usually a Gaussian, and decodes to an output x'. The network is optimised to reproduce the inputs x maximally well, given a small latent space z. Thus the difference between x and x' has to be minimised, as does the amount of information passing through the latent layer. This is encapsulated by minimising the cost function L. A tensorial VAE allows for the inputs, the networks themselves, and the latent space to either include tensor network components, or be fully constructed using tensor networks.

We will now formally re-state the high-level concepts underlying the GTN system that have been discussed in this specification, as well as a large number of implementation features. Note that any high-level concept may be combined with any other high level concept and any one or more features.

Concept A

Providing a tensor network representation of molecular quantum states of small drug-like molecules as an input to a machine learning system, e.g. a neural network system.

Concept B

Providing a tensor network representation of molecular quantum states of small drug-like molecules as an input to a machine learning system, e.g. a neural network system, where the machine learning system is itself configured as a tensor network or includes tensor decompositions in its components.

Concept C

Creating a training dataset for a machine learning system, where the training dataset is a tensor network representation of the molecular quantum states of small drug-like molecules.

Concept D

A machine learning system, e.g. a neural network system, that takes as its input, tensor network representations of the molecular quantum states of small drug-like molecules and provides, as its output, tensor network representations of the molecular quantum states of small drug-like molecules to a predictive model that screens the output from the machine learning system.

Concept E

A machine learning based process for identifying small drug-like molecules including the following steps:
(i) using tensor networks to efficiently represent a set of molecular quantum states of small drug-like molecules;
(ii) providing that tensor network representation as an input to a machine learning system, e.g. a neural network system;
(ii) the machine learning system efficiently searching through, sampling or otherwise analyzing this tensor network representation to identify candidate small drug-like molecules with required properties (e.g. prediction of binding to a target protein).

Subsidiary Features for Concepts A-E

Tensor Networks
the tensor networks contain direct information about quantum correlations and entanglement properties
the tensor network representations include one or more of: matrix product state (MPS), multi-scale entanglement renormalization ansatz (MERA), and projected entangled-pair states (PEPS), correlator product states, tree tensor networks, complete graph network states, tensor network states.
the tensor network representations include networks describing states with volume law entanglement, which can, for example, provide descriptions of highly excited states present in transition states of small molecules in a reaction or a binding process. It also allows for tensor networks describing density matrices—both those that obey the area law, and those that do not, and arbitrary superpositions of tensor networks, containing elements in general from distinct types of architectures (e.g. a superposition of two MPS tensor networks with a MERA network).
the tensor networks efficiently represent a set of molecular quantum states of small drug-like molecules
the set of molecular quantum states of small drug-like molecules is an exponentially large search space, e.g. a part or a significant part of the $10^{60}$ small drug-like molecules.
A feature map is applied to input data to transform that input into a high dimensional tensor network structure
A graph feature map is applied to input data to transform that input into a high dimensional tensor network structure
featurization of graph models is by introducing entanglement features or other quantum mechanically features, derived from approximate molecular wave functions (e.g. from their tensor network descriptions, as obtained by minimising the tensor network components with respect to energy).

Training Datasets
the tensor network representations are or include a training data set of small drug-like molecules
the tensor network represents a set of simple descriptions of a molecule, so that a large set of molecules=1 tensor network
the training dataset is tensor network representation of the molecular quantum states of small drug-like molecules
the tensor network representations include a training data set of small drug-like molecules and a target, in which the small drug-like molecules are known to bind to the target.
the training dataset is tensor network representation of the molecular quantum states of small drug-like molecules and also a tensor network representation of the molecular quantum states of one or more targets, e.g. a protein to which a drug-like molecule may potentially bind, the protein binding pocket, or the description of the protein and small molecule as one large graph or tensor network.
the training dataset is used to train a generative model.
the training dataset is used to train a predictive model.
the predictive model is configured to predict whether a candidate small drug-like molecule is appropriate to a specific requirement
The specific requirement is guided in terms of similarity to a particular molecule, using standard chemistry comparison methods, e.g. Tanimoto similarity, or using the latent space of a trained model, similarity measures between tensor network descriptions of the outputs (e.g. norm of the overlap between the candidate and target molecules).
the predictive model is configured to guide the generative model in determining whether a candidate small drug-like molecule is appropriate to a specific requirement
a specific requirement is the capacity of a small drug-like molecule to bind to a target protein
a specific requirement is one or more of the following: absorption; distribution; metabolism; toxicity, solubility, melting point, log(P).
a specific requirement is another biological process, such as an output of an assay designed to capture a specific phenotype. As an example, eczema results from continuous and unresolved inflammatory responses mediated by cytokines, leading to skin irritation and inflammation. The inflammation can be observed at the molecular level by the overexpression of CCL5, and a machine learning model can be trained to predict results of the assay.

The training dataset is used to train a generative model, which in turn feeds the predictive model The training dataset is fed high-quality molecules by a predictive model predictive model is a feed-forward system Machine Learning the machine learning system is configured to handle tensor network inputs the machine learning system is configured to handle tensor network inputs by applying (tensorial) layers to the input, and using a mechanism to decrease the complexity of the resulting tensor network, so that it can be feasibly run on classical computers. For example, if the input network is a matrix product state (MPS), and the machine learning network consists of N applications of a matrix product operator (MPO), the bond dimension of the resulting MPS that needs to be stored in intermediate points in the calculation grows exponentially with N. A method to reduce the bond dimension (using e.g. standard DMRG SVD style projections), needs to be introduced to keep the calculation feasible on classical computers.

the machine learning system has been trained on a training dataset the machine learning system is supervised, semi-supervised or unsupervised machine learning system is a generative network, or an autoencoder, or RNN, or Monte-Carlo tree search model, or an Ising model or a restricted Boltzmann machine trained in an unsupervised manner.

machine learning system is a generative adversarial network the generative adversarial network is configured to receive a training dataset and to train (a) a generative model G that captures the training dataset distribution and (b) a discriminative model D that estimates the probability that a sample came from the training dataset rather than G.

machine learning system is a neural network that comprises tensorial decompositions or tensor networks.

machine learning system is a neural network constructed as a tensor network.

machine learning system is a quantum computer with quantum circuits configured as a tensor networks machine learning system is a quantum machine learning circuit (optionally based on a tensor network, and obtained by embedding the tensors in the networks into unitary gates). Such a circuit could take a machine learning computation that is classically not feasible, such as the MPO example above without SVD projections, and run it efficiently.

Predictive Model the machine learning system outputs tensor network representations of the molecular quantum states of small drug-like molecules to a predictive model the predictive model screens the output from the machine learning system.

the predictive model screens the output from the machine learning system by assessing the capacity of each sampled molecule to meet a specific requirement the predictive model is a feed-forward system that adds high-quality molecules to a source training dataset.

The predictive model is based on graph input data, or on graph input data enhanced by quantum features (as described in Appendix 2).

Concept F

A method of analysing a chemical compound dataset so as to determine suitable chemical compounds, the method comprising:
  (i) determining a tensorial space for said chemical compounds dataset;
  (ii) correlating the tensorial space with a latent space (and which may itself have a tensorial description); and
  (iii) outputting a further dataset of candidate chemical compounds.

A system for analysing a chemical compound dataset so as to determine suitable candidate chemical compounds, the system comprising:
  (i) means for receiving a chemical compound dataset;
  (ii) a processor for processing the chemical compound dataset to determine a tensorial space for said chemical compound dataset;
  (iii) a processor for correlating said tensorial space with a latent space; and
  (iv) means for outputting a further dataset of candidate chemical compounds A method of analysing a chemical compound dataset so as to determine suitable chemical compounds, the method comprising:
  (i) generate tensor networks for a dataset of small drug like molecules, or other chemical compounds;
  (ii) correlate the tensor network description of chemical compounds, with machine learning models, where the machine learning models may themselves contain tensor network components, or be tensor networks in their entirety;
  (iii) in the context of generative models, correlate the inputs and models with a latent space of a variational autoencoder model, or use it in the context of other generative models (the latent space is usually a small vector space, but may have a more general tensor network structure);
  (iv) output a further dataset of candidate small drug like molecules, or other chemical compounds, via generative models.
  (v) use a combination of tensorial predictive and generative molecules to guide the search through the space of small chemical compounds.

Subsidiary Features for Concept F the tensorial space is a wave function space.

latent space represents physically relevant wave functions.

latent space represents physically relevant wave functions in conjunction with a decoder network.

the further dataset of candidate chemical compounds is a filtered dataset of candidate chemical compounds.

the further dataset of candidate chemical compounds is a novel dataset of candidate chemical compounds.

Wave functions describing elements in some (e.g. molecular) datasets are each represented by an appropriate tensor network. A whole set of wave functions could be described by an appropriate tensor network as well.

the tensor network is one of: complete-graph tensor network state, correlator product state, projected entanglement pair states (PEPS), matrix product states (MPS)/tensor train, tree tensor network, and matrix product operator.

the dataset is mapped into a higher dimensional tensor.

the correlating process includes optimising over the latent space.

the correlating process includes determining an optimal tensor network to describe the mapping of the input data set to a more general description.

the latent space represents desired properties of a set of candidate chemical compounds.

the correlating process includes maximising a cost function, said cost function representing desirable properties of the candidate chemical compounds.

determining the tensorial space for the chemical compounds dataset comprises encoding said dataset using a generative model.

The outputting process includes the process of decoding using a generative model.

the generative model comprises a neural network.

the generative model comprises a graph variational auto encoder or graph based GAN, with enhanced featurisation based on separate quantum mechanical calculations (perhaps done using tensor network methods, or other quantum chemistry methods).

the neural network is in the form of an autoencoder.

the autoencoder is a variational autoencoder.

the neural network is any of the following: generative auto encoder, RNN, GAN, Monte-Carlo tree search model, an Ising model or a restricted Boltzmann machine trained in an unsupervised manner etc. (see openreview.net/pdf?id=Bk0xiI1Dz, arxiv.org/abs/1710.07831, and references therein]

the neural network comprises tensorial decompositions or tensor networks, or is constructed as a tensor network in its entirety.

the tensor network comprises a tensorial generative autoencoder.

A visualisation of the tensorial space is generated and output.

candidate chemical compounds are active elements of a pharmaceutical compound.

candidate chemical compounds are suitable for use in an organic light emitting diode.

The chemical compound dataset is a dataset of possible molecules containing up to a predetermined maximum number of atoms.

System

A system configured to perform any of the preceding methods.

Molecules

A molecule or class of molecules identified using any of the above processes or systems.

Some Formal Points on the Scope of the Invention

The invention extends to methods, system and apparatus substantially as herein described and/or as illustrated with reference to the accompanying figures. The invention also provides a computer program or a computer program product for carrying out any of the methods described herein, and/or for embodying any of the apparatus or system features described herein, and a computer readable medium having stored thereon a program for carrying out any of the methods described herein and/or for embodying any of the apparatus features described herein. The invention also provides a signal embodying a computer program or a computer program product for carrying out any of the methods described herein, and/or for embodying any of the apparatus features described herein, a method of transmitting such a signal, and a computer product having an operating system which supports a computer program for carrying out the methods described herein and/or for embodying any of the apparatus features described herein.

Any feature in one aspect of the invention may be applied to other aspects of the invention, in any appropriate combination. In particular, method aspects may be applied to apparatus aspects, and vice versa. As used herein, means plus function features may be expressed alternatively in terms of their corresponding structure, such as a suitably programmed processor and associated memory. Furthermore, features implanted in hardware may generally be implemented in software, and vice versa. Any reference to software and hardware features herein should be construed accordingly. It will be appreciated that although the present invention has been described principally in the field of filtering molecule datasets for drug development (and the like), the described methods may also be used in any field in which a large, multi-dimensional search space exists. It will be understood that the invention has been described above purely by way of example, and modifications of detail can be made within the scope of the invention. Each feature disclosed in the description, and (where appropriate) the claims and drawings may be provided independently or in any appropriate combination. Reference numerals appearing in the claims are by way of illustration only and shall have no limiting effect on the scope of the claims. Inclusion of a reference or citation in this specification is neither acceptance nor implication that it is valid or relevant prior art; for example, in light of the fast moving field of this invention, references have been included in this specification that post-date the priority date, but precede its filing date, and these references should be assumed to be non-citable prior art.

APPENDIX 2

Primer on Graph Featurization and Tensor Networks

This Appendix 2 contain background, ideas, details, and preliminary results on how we go about adding physically-inspired entanglement features to the GTN system's machine learning graph models using well-established quantum chemistry methods and tensor network algorithms.

1. High Level Overview

According to some, the holy grail of rational drug design would be the advent of large scale quantum computers capable of aiding and guiding scientists at every step in the drug discovery process. These devices would exploit our understanding of quantum mechanics to directly simulate nature. Since quantum computing in its current form is very much a toy project in its infancy, decades away from any applications, one feels obliged to come up with other strategies in the meantime.

One such strategy involves combining machine learning algorithms with computational chemistry, leveraging recent advances in computational infrastructure. Let us focus on ligand-based drug design for now since structure-based drug design comes with its additional set of complications, assumptions, and approximations. Ideally, from a physics perspective, one would like to feed the molecule's wave function (or its tensor network representation) as input to a machine learning (ML) pipeline. The intuitive reason for this is that you want to make the algorithm focus on calculating properties and not on finding the ground state by already providing it with the wave function as input data. Not doing so arguably makes the learning much harder, since, by refusing to input anything interesting on the structure of the wave function, machine learning algorithms can get confused when trying to build a statistical model of the data. Given oversimplified proxies of the wave function like fingerprints and SMILES strings, the model has to learn how to run (what is measurable property X calculated from the wave function?) before it can even walk (what is a wave function?). One can argue that it is naive to think that a ML algorithm implicitly has to first solve the Schrödinger equation and calculate the ground state before calculating properties like humans do, but it is equally questionable to assume that it finds a set of magical weights which bypass quantum mechanics altogether. Machine learning is far from a black box and it is advisable to find a delicate balance between letting the algorithm figure out things on its own and steering the learning process.

Since inputting the full wave function (or its tensor network representation) is intractable at the moment, one can input SMILES or graphs or other proxies for the wave function data, together with a list of observed or measured global properties of the molecule. But there's more to chemistry than SMILES strings and atom connectivity. In the short-term, the idea would be to improve the ad hoc featurization of graph models by introducing features derived from approximate molecular wave functions, supplying fine-grained information about the underlying chemistry/physics. The expectation is that this should lead to stronger learning capabilities, better generalization, and improved latent representations without overfitting, which is important for both predictive and generative models. Starting from a molecule's composition, ab initio quantum chemistry methods try to approximate the molecular wave function in some appropriately chosen orbital basis set. The properties/features we extract from these methods should in some sense be raw, i.e. independent of the method or basis used and as close as possible to the wave function data. It is important to stress that our goal is not to obtain the best possible ground state energies for every particular conformation of the molecules in a dataset. That would be silly and also quite impossible for the sizes of the datasets we are interested in. We need something quick and reasonably accurate to deduce qualitatively correct information about the electronic correlations, under the implicit assumption that any information on quantum correlations and actual chemistry will be better than just inputting SMILES.

2. Quantum Chemistry 101 (for Physicists)

We will focus on ab initio quantum chemistry methods for the electronic structure of small molecules within the Born-Oppenheimer approximation of the time-independent non-relativistic quantum many-body Schrodinger equation.

$$H(R,r)\Psi(R,r)=E(R)\Psi(R,r), \quad (1)$$

with the molecular Hamiltonian $$H_{elec}(R, r) = -\frac{1}{2}\sum_{i=1}^{N}\nabla_i^2 - \frac{1}{2}\sum_{A=1}^{M}\frac{1}{M_A}\nabla_A^2 - \sum_{i=1}^{N}\sum_{A=1}^{M}\frac{Z_A}{r_{iA}} + \sum_{i=1}^{N}\sum_{j>i}^{N}\frac{1}{r_{ij}} + \sum_{A=1}^{M}\sum_{B>A}^{M}\frac{Z_A Z_B}{R_{AB}}, \quad (2)$$

where $Z_A$, $M_A$, M, and N denote respectively nuclear charges, nuclear masses relative to the electron's mass, the number of nuclei, and the number of electrons. The electronic part of the Schrödinger equation looks like $$H_{elec}(R, r)\chi(R, r) = E_{elec}(R)\chi(R, r) \quad (3)$$

where $$H_{elec}(R, r) = -\frac{1}{2}\sum_{i=1}^{N}\nabla_i^2 - \sum_{i=1}^{N}\sum_{A=1}^{M}\frac{Z_A}{r_{iA}} + \sum_{i=1}^{N}\sum_{j>i}^{N}\frac{1}{r_{ij}}, \quad (4)$$

so that the total energy is simply $$E_{tot}=E_{elec}+E_{nucl}$$

FIG. 22 reproduces equations (1) to (4).

In practice, one uses a finite set of basis functions to turn the above partial differential equations into algebraic equations amenable to numerical simulation. In electronic structure calculations for condensed-matter physics plane waves are natural whereas in quantum chemistry people are fond of atomic orbitals. Note that basis functions are most often not true atomic orbitals, apart from hydrogen and other one-electron systems. It is important to remember that orbitals, like anything in physics, are just mathematical constructs which approximate reality. Common basis sets are Gaussian-type orbitals, Slater-type orbitals, or other numerically obtained orbitals. While atomic orbitals contain the electrons of a single atom, molecular orbitals, which surround a number of atoms in a molecule, are said to describe valence electrons shared between atoms. To understand bonding, molecular orbital theory thus approximates the molecular orbitals (which, essentially, correspond to delocalized electrons) as linear combinations of atomic orbitals (LCAO).

2.1 Hartree-Fock Method

The Hartree-Fock (HF) method is a variational procedure which approximates energy eigenfunctions of the electronic Schrodinger equation (3) by a single Slater determinant, i.e. an anti-symmetrized product of one-electron wave functions (orbitals), $$\Psi(x_1, x_2, \ldots, x_N) = \frac{1}{\sqrt{N!}}\begin{vmatrix} \chi_1(x_1) & \chi_2(x_1) & \cdots & \chi_N(x_1) \\ \chi_1(x_2) & \chi_2(x_2) & \cdots & \chi_N(x_2) \\ \vdots & \vdots & \ddots & \vdots \\ \chi_1(x_N) & \chi_2(x_N) & \cdots & \chi_N(x_N) \end{vmatrix} \quad (5)$$

$$\equiv |\chi_1, \chi_2, \ldots, \chi_N\rangle, \quad (6)$$

where the $$\chi_i(x), \forall i \in \{1, 2, \ldots N\}$$

are a set of one-electron spin-orbital wave functions. FIG. 23 reproduces equations (5) to (6). These are products of a spatial orbital $\psi_i(r)$ and a spin function $\alpha$ or $\beta$. Note that each electron is actually associated with every orbital (the electrons are indistinguishable) and that the number of electrons N is taken to be equal to the number of orbitals L.

The Fermi correlation due to electron exchange (Pauli exclusion principle) is accounted for via the explicit anti-symmetrization. Electrons move independently within molecular orbitals, each of which describes the probability distribution of a single electron. On top of that, the HF approximation also resorts to a mean-field treatment of the interactions among electrons, neglecting the instantaneous electron-electron correlations. Every electron only feels an average contribution of all other electrons.

2.1.1 Self-Consistent Field Algorithm

The starting point of HF calculations is the molecular geometry (3D coordinates) and a finite set of approximate one-electron wave functions (spin-orbitals). For a molecular orbital calculation, the initial one-electron wave functions are typically already a linear combination of atomic orbitals (LCAO). One obtains the optimum set of molecular orbitals by variationally minimizing the energy in what is called a "self-consistent field" or SCF approximation to the many-electron problem. Given a set of molecular orbitals, the energy expectation value is minimized by solving one-particle eigenvalue equations (Hartree-Fock-Roothan generalized eigenvalue equations) for the molecular orbitals. These new eigenfunctions can then be used to recalculate the average field felt by each electron, after which the procedure is repeated until the set of molecular orbitals converges to the so-called Hartree-Fock molecular orbitals.

In practice, there's a number of methods. Restricted Hartree-Fock (RHF) is used for closed-shell molecules at their equilibrium geometry, where electrons occupy orbitals in pairs. Restricted open-shell Hartree-Fock (ROHF) is used for open-shell molecules where the spin parts α and β of the orbitals are constrained to be identical, leading to proper eigenfunctions of the total spin operator but lacking a unique set of molecular orbitals since the form of the Fock matrix is often not unique. Unrestricted Hartree-Fock (UHF) is used for open-shell molecules and uses different molecular orbitals for the α and β electrons, leading a ground state which can be contaminated by excited states since spin is not conserved.

2.1.2 Hartree-Fock Wave Functions and Entanglement

Since the HF algorithm is variational, the HF energy is an upper bound to the true ground state energy of a given molecule, corresponding to the minimal energy for a single Slater determinant. The best possible solution is called the HF limit, where the basis set approaches completeness. On the other hand, dropping the HF approximations of a single Slater determinant and mean-field interactions, we arrive at the full-CI (configuration interaction) limit, which corresponds to the exact solution up to the Born-Oppenheimer approximation. The energy difference between the HF solution and the exact ground state is sometimes called the electron correlation energy. The exact ground state corresponding to the full-CI limit will be important to connect quantum chemistry methods to tensor networks (see Section 3.2 below).

In physics, we would call the wave function obtained from Hartree-Fock a mean-field solution, or a product state, or quite simply a boring state without any entanglement. The probability $P(r_1, r_2)$ of finding an electron at $r_1$ and $r_2$ is not simply $p(r_1)p(r_2)$. To deal with this weakness, a lot of post-Hartree-Fock methods have been devised, correcting for the neglected electron-electron correlation in different ways. Still, because HF is so cheap and often qualitatively correct, many types of calculations are initialized with a HF calculation.

2.2 Post-Hartree—Fock Methods

In general, the exact ground state wave function of the electronic Hamiltonian Equation (4) entails a superposition of all possible distributions of N electrons over L orbitals, i.e. a linear combination over all possible Slater determinants, which blows up factorially. In this sense, HF boils down to the simplest possible approximation by picking only a single Slater determinant. The occupancy of the HF orbitals is fixed: occupied orbitals are filled with probability 1 and virtual orbitals are empty with probability 1. Post-Hartree-Fock methods improve upon the HF-SCF method by adding the effects of electron correlation, which HF completely neglects apart from the exchange energy resulting from the explicit anti-symmetrization of the wave function. Note that there are many more post-Hartree-Fock methods than the ones we will mention below, including subtle variations and combinations with other methods.

2.2.1 Intuition

In second quantization (Fock space), orbitals are either doubly, singly, or unoccupied by an electron. We can conceptually regard Hartree-Fock with mostly paired electrons as optimizing occupied (lower 4 lines—red) and virtual (upper 4 lines—blue) orbital spaces such that the energy expectation value is minimized (also shown in FIG. 24):

$$|\psi_{HF}\rangle = \begin{array}{c} \underline{\phantom{xx}} \\ \underline{\phantom{xx}} \\ \underline{\phantom{xx}} \\ \underline{\uparrow\downarrow} \\ \underline{\uparrow\downarrow} \\ \underline{\uparrow\downarrow} \\ \underline{\uparrow\downarrow} \end{array} \qquad (7)$$

The configuration interaction (CI) method is a post-Hartree-Fock variational method which accounts for electron correlation by using a variational wave function that is a linear combination of configuration state functions (CSFs) built from spin orbitals. A configuration state function is a symmetry-adapted linear combination of Slater determinants.

$$|\psi_{CI}\rangle = C_0 \begin{array}{c}\underline{\phantom{x}}\\\underline{\phantom{x}}\\\underline{\uparrow\downarrow}\\\underline{\uparrow\downarrow}\\\underline{\uparrow\downarrow}\end{array} + \sum_{ia} C_i^a \begin{array}{c}\underline{\phantom{x}}\\\underline{\downarrow a}\\\underline{\uparrow\downarrow}\\\underline{\uparrow i}\\\underline{\uparrow\downarrow}\end{array} + \sum_{ijab} C_{ij}^{ab} \begin{array}{c}\underline{\uparrow b}\\\underline{\downarrow a}\\\underline{\uparrow\downarrow}\\\underline{\uparrow i}\\\underline{\downarrow j}\end{array} \qquad (8)$$

or $$|\Psi_{CI}\rangle = (1+T_1+T_2+\ldots)|\Psi_{HF}\rangle. \qquad (9)$$

FIG. 25 reproduces (8) to (9). The first term in the expansion is usually the HF determinant $$|\Psi_{HF}\rangle$$

and this reference state is assumed to be qualitatively correct and dominant. If the expansion includes all possible CSFs of the appropriate symmetry by exciting all possible electrons to all possible virtual orbitals, then this is a full configuration interaction procedure which exactly solves the electronic Schrodinger equation within the space spanned by the one-particle basis set. Usually though, the series is truncated to single and double excitations, leading to problems with size-consistency. Other methods like coupled cluster (CC) use an exponential trial wave function $$|\Psi_{CC}\rangle = e^{T_1+T_2+\cdots}|\Psi_{HF}\rangle$$

as an ansatz, which is size-consistent. On the other hand, coupled cluster is not variational since the normalisation of the wave function cannot be enforced. In practice that doesn't really matter though, since, for properties such as energy, it is known how to truncate the ansatz when examining expectation values (but not for the wave function itself!). The gold standard of quantum chemistry is often said to be CCSD(T), i.e. coupled cluster which includes singles, doubles, and perturbative triples corrections. Recent advances to improve computational costs of CCSD(T) and to counter the requirements for large basis sets have led to the development of DLPNO-CCSD(T) methods which exploit locality of correlations using strong pair approximations and pair natural orbitals.

For nearly degenerate states contributing to the ground state Eq. 8 one should use multi-configurational self-consistent field (MC-SCF) methods (see Section 2.2.3). In that case, the Hartree-Fock determinant reference state is qualitatively wrong, since the weight $|C_0|$ is not dominant, and so are the resulting CI wave functions and energies. This can happen when the ground state is strongly-correlated and static correlations have to be taken into account.

2.2.2 Static and Dynamic Correlations

Electron correlations are often rather artificially divided into two contributions: static and dynamic correlations. The former corresponds to configurations which are nearly degenerate with respect to the reference Slater determinant, while the latter arises from the need of mixing the Hartree-Fock state with a bunch of higher-order excited states. In systems with (strong) static correlation the wave function is said to differ qualitatively from the reference Slater determinant, while strong dynamic correlation implies a wave function which includes a large number of excited determinants, all with comparable, small occupations. An example of a method that recovers primarily dynamic correlation is Moller-Plesset perturbation theory (MPn), while multi-configurational self-consistent field (MC-SCF) methods primarily take care of static correlations. It is almost impossible to keep dynamic and static correlation effects separated since, from a physical point of view, they both arise from the very same interaction.

Dynamic correlation can also be captured with ab initio post-Hartree-Fock methods. These start from the optimized HF orbitals and the corresponding Slater determinant and build in dynamic correlation on top of that single reference state. Examples include the aforementioned MPn perturbation theory, the configuration interaction (CI) expansion, and coupled cluster (CC) theory. Because these post-Hartree-Fock methods start from a single Slater determinant reference, they have difficulty building in static correlation. It is therefore better to resort to multi-configurational self-consistent field (MC-SCF) methods for systems with pronounced static correlation, e.g. for molecular ground states which are quasi-degenerate with low-lying excited states or in bond breaking situations.

2.2.3 Multi-Configurational Methods

Figure 26:
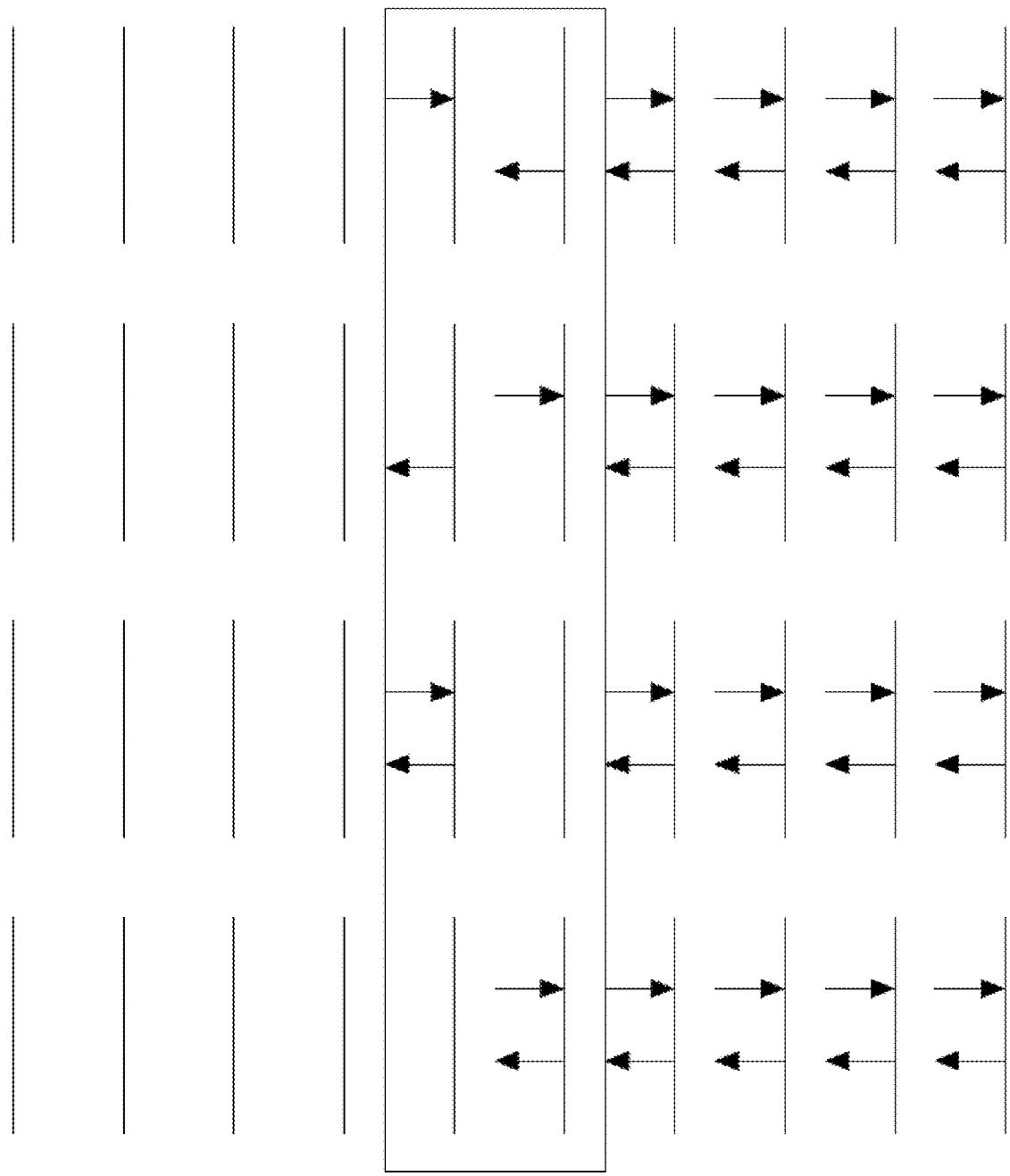
FIG. 26 schematically represents occupied, active and virtual orbitals.

Multi-configurational self-consistent field (MC-SCF) methods come into play when a single electron configuration does no longer provide an adequate description of the electronic structure. An important MC-SCF approach is the complete active space SCF (CAS-SCF) method which can be used to obtain an approximation of the static correlation. In this framework, orbitals can be classified as either occupied (always containing two electrons), active (partially occupied and relevant for the chemistry), and virtual (always empty). Intuitively, this is shown in FIG. 26.

From a HF solution, a subset of occupied and virtual orbitals is selected to act as active space. The remaining occupied and virtual orbitals are kept frozen at HF level and the electronic structure in the active space is solved for exactly. The notation CAS(N, L) refers to an active space containing N electrons distributed between all configurations that can be constructed from L molecular orbitals. A CAS-SCF simulation is a two-step process where the energy can be iteratively minimized by doing a full-CI calculation only in the active space (CAS-CI). That information is then used to rotate the occupied and active orbital spaces to minimize the energy even further. Because the many-body Hilbert space grows exponentially with the number of single-particle states, only small active spaces up to 18 electrons in 18 orbitals can be treated with CAS-CI (cf. exact diagonalization). Dynamic correlation is usually small and can be recovered with good accuracy by means of perturbative methods on top of the CAS solution which should contain the proper static correlation.

2.3 Remarks for Confused Physicists 2.3.1 Density Matrices

Density matrices are fundamental objects in quantum mechanics. To avoid confusion with the notion of a density matrix as used by physicists, let us explicitly state what is meant by the term in quantum chemistry and electronic structure calculations. In particular, the N-particle density matrix refers to:

$$\rho = |\Psi(x_1, x_2, \ldots, x_N)\rangle\langle\Psi(x_1, x_2, \ldots, x_N)|, \quad (10)$$

which specifies everything there is to know about the wave function of the system since it gives the probability of the state with a given set of coordinates xi (space and spin) for all electrons in the system. Since most physical operators are not N-electron operators (e.g. the kinetic energy operator is a one-electron operator and the Coulomb interaction is a two-electron operator), we do not require the full N-particle density matrix to calculate energies and local properties. If we trace out all coordinates except for x1, we arrive at the one-particle reduced density matrix (1PDM, ODM, 1RDM, ...)

$$\rho^{(1)}(x_1, x_1') = N \int \Psi^*(x_1', x_2, \ldots, x_N)\Psi(x_1, x_2, \ldots, x_N) \, dx_2 \ldots dx_N, \quad (11)$$

which is a generalization of the one-electron density $$\rho^{(1)}(x_1) = \int \Psi^*(x_1, x_2, \ldots, x_N)\Psi(x_1, x_2, \ldots, x_N) dx_2 \ldots dx_N. \quad (12)$$

Integrating the one-electron density over the spin of the first electron yields the following spin-free first-order reduced density matrix, $$P^{(1)}(r_1) = \int \rho^{(1)}(r_1; s_1) ds_1. \quad (13)$$

Similarly, we can also define a two-particle reduced density matrix $$\rho^{(2)}(x_1, x_2; x_1', x_2') = N(N-1) \int \Psi^*(x_1', x_2', \ldots, x_N) \Psi(x_1, x_2, \ldots, x_N) dx_3 \ldots dx_N, \quad (14)$$

which is a generalization of the two-electron density $$\rho^{(2)}(x_1, x_2) = N(N-1) \int \Psi^*(x_1, x_2, \ldots, x_N) \Psi(x_1, x_2, \ldots, x_N) dx_3 \ldots dx_N. \quad (15)$$

FIG. 27 reproduces equations (10) to (15). Determining the one- and two-particle RDMs is enough for the electronic structure problem. In the Hartree-Fock approximation, the one-particle RDM is enough since the two-particle, three-particle, ... density matrices can all be expressed in terms of direct products of the one-particle RDM. For correlated methods however, the $\rho^{(i)}$ density matrices have to be determined separately.

2.3.2 Orbitals

The one-particle RDM Eq. (11) can be written in terms of a complete set of spin-orbitals $$\rho^{(1)}(x_1, x_1') = \sum_{i,j} \rho_{ij}^{(1)} \phi_i(x_1) \phi_j^*(x_1'). \quad (16)$$

The diagonal elements $\rho^{(1)}$ are called orbital occupation numbers. Since a unitary transformation on the set of spin-orbitals leaves the wave function invariant, the matrix $\rho^{ij}$ can be transformed into diagonal form with diagonal elements $0 \leq n_i \leq 1$ corresponding to the occupation numbers of the natural spin-orbitals (NSOs), satisfying $$\Sigma_i n_i = N.$$

The one-particle RDM then becomes $$\rho^{(1)}(x_1, x_1') = \sum_i n_i \phi_i^{NSO}(x_1) \phi_j^{*NSO}(x_1'). \tag{17}$$

Diagonalizing the spin-free first-order RDM yields so-called natural orbitals (NOs), which constitute an orthonormal set of eigenorbitals intrinsic to the N-electron wave function, $$P^{(1)}(r_1, r_1') = \sum_i n_i \phi_i^{NO}(r_1) \phi_j^{*NO}(r_1'). \tag{18}$$

where now $0 \leq n_i \leq 2$.

FIG. 28 reproduces equations (16) to (18).

Molecular orbitals are completely fictitious constructs used to piece together a wave function of the molecule. As we have seen above, solving an energy eigenvalue equation using a set of basis orbitals (orthogonal or non-orthogonal) yields so-called canonical molecular orbitals (CMOs), which represent specific electrons and can generically be completely delocalized over the entire molecule. For our purposes, it may prove fruitful to consider localized molecular orbitals (LMOs), which are concentrated in a limited spatial region of a molecule and relate MO calculations back to theory of chemical bonding. These LMOs are obtained from a unitary transformation on a set of delocalized CMOs (a linear combination) by optimizing the expectation value of some operator. For closed-shell molecules, the localized and delocalized orbital descriptions are equivalent and represent the same physical state. Different prescriptions (Foster-Boys, Edmiston-Ruedenberg, Pipek-Mezey) optimize different quantities and can thus lead to different localized orbitals.

Another approach to localization of molecular orbitals is given by natural bond orbitals (NBOs) which represent electron density and stay closer to the intuitive picture of chemical bonding (on the other hand, NBOS can have any occupancy since this property is no longer well defined). These orbitals are constructed to have maximum electron density, corresponding to the best possible Lewis structure, and are part of a sequence of orbital sets related by similarity/unitary transformations (also shown in FIG. 28):

$$\text{Atomic orbital} \rightarrow \text{NHO} \rightarrow \text{NBO} \rightarrow \text{NLMO} \rightarrow \text{Molecular orbital}, \tag{19}$$

which includes natural atomic orbitals (NAO), natural hybrid orbitals (NHO), natural bonding orbitals (NBO) and natural (semi-)localized molecular orbitals (NLMO). These natural localized sets of orbitals are in between atomic orbitals and molecular orbitals. Natural atomic orbitals (NAOs) correspond to the effective natural orbitals of an atom in the molecular environment, with core and valence-shell NAOs having significant occupancies. Natural bond orbitals (NBOs) are optimized linear combinations of NAOs which attempt to give the best possible valence bond-type description of the wave function. They are said to be insensitive to variations of basis sets or approximation methods and to reflect the character of the wave function uniquely. Finally, the natural localized molecular orbitals (NLMOs) are LMOs which are obtained by optimizing for minimal delocalization of NBOs.

2.3.3 Wave Functions and Relaxed Density Matrices

For wave functions which are exact solutions of the Schrödinger equation, obtaining one-particle RDMs boils down to a pretty straightforward application of quantum mechanics.

But quantum chemistry uses incomplete basis sets and a whole host of approximations, invalidating this naive physicists' picture. Computational methods like HF, CI, MC-SCF, and QC-DMRG do have approximate wave functions associated to them in the sense that their expressions for the energy correspond to the expectation value of the Hamiltonian operator calculated using those approximate wave functions. The one particle RDM derived from these approximate wave function methods is well-defined and the expectation value of any one-electron property is simply the trace of the density matrix multiplied by the operator representing that property.

However, it is important to stress that other methods (DFT, MPn, and coupled cluster) do not have wave functions at all, not even approximate ones. What this means is that the approximate "wave function" simply does not exist (like in DFT where the quantity of interest is an effective density), or that the energy evaluated in these methods using the corresponding approximate "wave function" does not at all correspond to the expectation value of the Hamiltonian using this same "wave function" (MPn and CC methods). To appreciate this, let us define a response-type density matrix D, defined such that the derivative of the energy E with respect to any one-electron perturbation is xV is E'=Tr(DV); which leads to identical results for methods which optimize the energy with respect to molecular orbitals (HF, MC-SCF, full-CI). For approximate solutions (like CISD), they can differ and one can define both expectation value and response-type density matrices with different properties. Calculating quantities like dipole moments then gives two different answers for the two kinds of density matrices, namely the expectation value of the dipole operator and the derivative of the energy with respect to the applied electric field. The response-type density matrix is often called the relaxed density matrix and does not require a wave function to be defined. For methods without an approximate wave function, one can still construct approximations to the expectation value density matrix, which are then called unrelaxed densities.

3. Tensor Networks and Quantum Chemistry

Applying tensor network ideas to quantum chemistry has been initiated in the group of White [cite 3 Wouters 2014] and has been subsequently developed in the groups of Legeza, Chan, Reiher, and Van Neck during the past 15 years. For a more extensive overview of ab initio DMRG in quantum chemistry, we refer to the introductory chapters of the PhD dissertations of Sebastian Wouters [cite 4: Wouters 2014] and Johannes Hachmann [cite 5: Hachmann 2010].

3.1 What is a Tensor Network?

Tensor networks are entanglement-based ansätze for ground and excited states of quantum many-body systems. There exist lots of different tensor networks tailored to different kinds of entanglement structure, but they all boil down to the same idea: efficient ways of exploring the 'physical" part of an exponentially large many-body Hilbert space. The reason this even works at all can be understood in terms of entanglement area laws and the local nature of interactions. Put differently, a tremendous amount of information in the 'mathematical" exponential Hilbert space is completely redundant and superfluous if you are interested in 'physical' ground states and low-lying excited states of local Hamiltonians.

3.2 Matrix Product States: QC-DMRG

Figures 29, 30, 31:
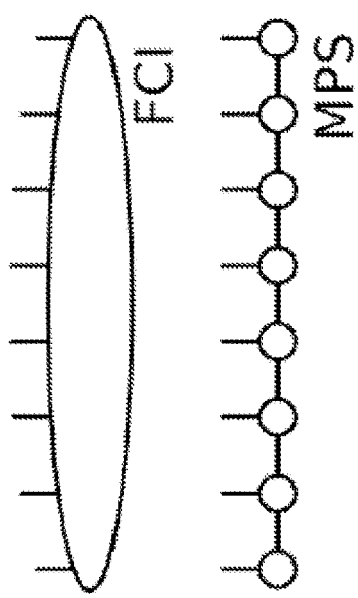
FIG. 29 shows equations (20) from Appendix 2.
FIG. 30 pictorially represents MPS tensors
FIG. 31 shows equations (11) from Appendix 2.

For our purposes, we will focus on matrix product states (MPS), which is the particular kind of linear ansatz underlying the influential density matrix renormalization group (DMRG) algorithm. The quantum chemistry version of DMRG (QC-DMRG) naturally emerges when trying to construct a tensor decomposition of the full-CI wave function. Recall that in the CAS-SCF approach, we select an active space of N electrons in L orbitals, on which a full-CI expansion is applied [cite 6].

$$|\Psi_{CAS-CI}\rangle = \sum_{n_1,\ldots,n_L} C_{n_1,\ldots,n_L}|n_1 n_2 \ldots n_L\rangle, \quad (20)$$

where $|n_1 n_2 \ldots n_L\rangle$ is an occupation number vector (Fock space). FIG. 29 reproduces equation (20). This ansatz scales exponentially since the calculations of the full-CI tensor is limited to CAS(18,18) spaces (cf.~exact diagonalization). By doing successive singular value decompositions (SVDs) on the rank-n tensor C, we arrive at an ansatz in terms of local tensors. Pictorially, this is shown in FIG. 30 [cite 7].

This leads to an ansatz for the wave function where the FCI tensor is rewritten as a contracted matrix product. Unlike most wave function methods in quantum chemistry, the MPS wave function is not parametrized by excitations from an underlying reference state but built directly from these local variational objects (tensors). Rather than truncating the number of excitations on top of some single reference state, QC-DMRG truncates in a virtual space of bond dimension D (the horizontal legs) containing entanglement degrees of freedom with no preferences towards any particular state, which makes it a natural candidate to study multi-configurational systems where static correlations are important. The error in the MPS wave function can be quantified by the truncation error $$\epsilon = \||\Psi\rangle - |\tilde{\Psi}\rangle\|^2 = 1 - \sum_{\alpha=1}^{D} w_\alpha, \quad (21)$$

where the target wave function $|\Psi\rangle$ is approximated by $|\tilde{\Psi}\rangle$ and $\omega_\alpha$ are the eigenvalues of the local reduced density matrix which you throw away. FIG. 31 reproduces equation (21). The DMRG is an iterative algorithm which optimizes over MPS wave functions to converge to the exact solution of the electronic Schrodinger equation in a given active orbital space with polynomial rather than exponential cost. Unlike traditional CAS-based approaches, DMRG is a local multi-configurational approach which, thanks to its polynomial scaling, can deal with active spaces comprising up to 50 orbitals. In terms of the number of orbitals L (corresponding to the number of lattice sites) and the bond dimension D, the QC-DMRG algorithm has an overall scaling per sweep of $\mathcal{O}(L^4 D^2 + L^3 D^3)$ in CPU time, $\mathcal{O}(L^2 D^2)$ in memory, and $\mathcal{O}(L^3 D^2)$ in disk.

The correlations among the orbitals are characterized by the bond dimension D which sets the number of variational parameters (for $D \to \infty$, the wave function would become exact for a given active space). The one-dimensional nature of the ansatz suggests that it is important to order orbitals along the chain such that strongly-correlated ones are close to each other (otherwise, correlations would have to travel "through" many sites of the chain to communicate). The QC-DMRG algorithm has been combined with CAS-SCF methods to optimize the orbitals themselves, using the QC-DMRG method as an approximate solver in the active space instead of CI. Dynamical correlations can be added on top of the MPS reference wave function by resorting to N-electron valence perturbation theory to second-order (NEVPT2) and complete-active space perturbation theory to second order (CASPT2) [Cite 6: Knecht 2015].

Recent applications of QC-DMRG are listed in the review article [Cite 7: Wouters 2014a]. For more details, we recommend the very same review article [cite 7: Wouters 2014a] by Sebastian Wouters since he uses modern MPS notation rather than old-fashioned DMRG-block style notation. Other reviews are included in the references [Cite 6: Chan 2008; Cites 8-10: Chan 2011, Olivares-Amaya 2015, Knecht 2015] and another extensive list of references can be found at quattro.phys.sci.kobe-u.ac.jp/dmrg/prop4.pdf. A great introductory talk is the one by Chan [Cite 11: Chan2015].

3.3 Software Packages for QC-DMRG

Since it takes an entire PhD to develop a decent QC-DMRG code which implements symmetries and supports parallelization through OpenMP and MPI, we should use an already developed package. Considering freely available packages: There's QuMaquis by the Eihert group but the code is stored on a private repository which you have to request access to. There's Block by the Chan group and CheMPS2 by Sebastian Wouters, both of which are written in C++ with Python wrappers.

3.4 Entanglement Measures

One reason to try QC-DMRG is that the one-orbital von Neumann entropy $$S_i = -\sum_{\alpha=1}^{4} w_{\alpha,i} \ln w_{\alpha,i}, \quad (22)$$

the two-orbital von Neumann entropy $$S_{ij} = -\sum_{\alpha=1}^{16} w_{\alpha,ij} \ln w_{\alpha,ij}, \quad (23)$$

and the mutual information between a pair of orbitals $$I_{ij} = \tfrac{1}{2}(S_i + S_j - S_{ij})(1 - \delta_{ij}) \quad (24)$$

can be calculated in a straightforward way from the tensor network representation of the molecular wave function in orbital space (see also Question 1 below). FIG. 32 reproduces equations (22) to (24). These bipartite entanglement measures reveal a lot about the correlations in the quantum state. In particular, calculating these quantities using QC-DMRG, for a given choice of orbitals and orbital order, leads to complex diagrams where the linear, one-dimensional MPS chain has been plotted as a circle. Every dot in corresponds to an style of the lines connecting the orbitals denote the value of the mutual information for those two orbitals.

Note that a correlated wavefunction is required to have non-zero orbital entanglement and correlation. In the case of an uncorrelated wavefunction (for instance, a single Slater determinant) the (orbital) entanglement entropy is zero.

Stein and Reiher have proposed to use these measures to automate the selection of active orbital spaces in CAS-DMRG by exploiting the capability of QC-DMRG to include up to about one hundred orbitals in the active space to systematically assess and select active orbitals [Cite 16: Stein 2016].

3.5 Other QC-TNS Ansätze

Apart from the linear matrix product state (MPS) ansatz, people have also considered using tree tensor networks (TNS) [Cites 12-14: Nakatani 2013, Murg 2015, Gunst 2018] and other tensor product states like complete graphs [Cite 15: Marti 2010a]. Even though these alternative ansätze might seem more appealing because trees kind of look like molecules, we should go with DMRG (see also Question 2 in the FAQ section) since we want a workhorse that does its job. More importantly, there is no code available for these alternative ansätze which comes anywhere near the level of performance we require.

4. Integration into GTN Pipeline: Featurization 4.1 Featurization and Generalization of Graph Models As mentioned in the overview, a short-term application would be to enhance 2D molecular graphs of deep learning models with quantum features derived from ab initio quantum chemistry simulations. Rather than familiar, global molecular descriptors, these features ought to be sufficiently indicative of the electronic correlations and serve as a proxy for the information contained in the wave function. Localized features would facilitate the transformation to atoms (nodes) and bonds (edges) and could be incorporated in the feature descriptions of known graph models. Delocalized features would require generalizing graph models to include additional structure capable of accommodating quantum correlations.

4.2 Challenges, Questions, and Remarks 4.1.1 Quantum Chemistry

What QC method to use? One reason to pick QC-DMRG is its natural connection to tensor networks, quantum information, and entanglement theory. Additionally, people have observed that cheap calculations at low bond dimensions already incorporate qualitatively okay entanglement features, in the sense that orbital entanglement entropies calculated at low bond dimension already give a measure of the entanglement in the wave function which generically survives when going to higher bond dimensions [Cite 16-18: Keller 2015, Stein 2016, Stein 2017]. That's a great observation for our purposes: this means we can get away with low bond dimensions to extract qualitatively okay information on the correlations.

If QC-DMRG turns out to not be optimal, we can resort to other more well-known ab initio quantum chemistry methods, for which we would need additional input from experienced computational chemists to decide on what is feasible and what is not. It is important to stress that our goal is not to obtain the best possible ground state energies for every particular conformation of the molecules in a dataset. That would be silly (and infeasible for the sizes of the datasets we're interested in). We need something quick and reasonably accurate.

Choice of Orbitals and Active Space?

As mentioned by the ORCA user guide
[ref: orcaforum.cec.mpg.de/OrcaManual.pdf]:
Let us stress again: it is strongly recommended to first LOOK at your orbitals and make sure that the ones that will enter the active space are really the ones that you want to be in the active space! Many problems can be solved by thinking about the desired physical contents of the reference space before starting a CASSCF. A poor choice of orbitals results in poor convergence or poor accuracy of the results! Choosing the active orbitals always requires chemical and physical insight into the molecules that you are studying!}

There's also these snippets from the MOLCAS manual:
molcas.org/documentation/manual/node60.html
molcas.org/documentation/manual/
    node61.html#SECTION0432740000000000000000

The bottom-line appears to be that 'chemical intuition" is required.

For QC-DMRG specifically, there is also the issue of the ordering of the orbitals on the one-dimensional chain. Finding the optimal ordering is in general NP-hard, so people use heuristics, chemical intuition, or a Fiedler vector ordering obtained from the Laplacian matrix of the graph [Cite 6, 7, 9, 10, 19: Chan 2011, Wouters 2014a, Olivares-Amaya 2015, Ghosh 2008, Knecht 2015].

Irrespective of the underlying quantum-chemical method and the mapping to the atomic graphs, at least the following steps will need to be (semi-)automated when dealing with thousands of molecules (and their different confirmations):

Choice of orbitals: determines basis for the QC-DMRG calculation but is also required and extremely important for every other quantum chemistry method. We could design a heuristic scheme which takes into account a list of recommendations and proposes molecular orbitals/active spaces, plots the orbitals in real-time, and have a chemist monitor the plots to intervene when something weird is going on, preferably before doing any more time-consuming (and wrong) calculations.

Conformations: In reality, different possible conformations contribute to what is actually measured in the lab. From the point of view of the input to ab initio QC methods, one would just view every different conformation as a different problem (since it is a different geometrical configuration) and sample/average out before the conversion to the graph features.

According to Chan [cite 11: Chan2015], DMRG is part of a wider ecosystem—except in the smallest molecules, DMRG cannot treat all degrees of freedom.

Parallelization and scaling: Computationally, the QC(-DMRG) calculations for different molecules can obviously be parallelized. For every molecule, the optimization of the wave function and subsequent calculation of all the one- and two-orbital reduced density matrices are independent. However, scaling this up will require considerations on what data we do and do not store on disk since the explicit wave functions and RDMs can get very big for a large amount of orbitals. If the calculations turn out to be sufficiently cheap, we just might want to store the correlation information and forget about the wave.

Frequently Asked Questions

1. Is it possible to calculate entanglement entropies of orbitals and mutual information between pairs of orbitals using methods other than QC-DMRG?

Yes, sure, it's just some operation on a bunch of eigenvalues of density matrices. Even though the one-orbital and two-orbital RDMs can be naturally calculated from a QC-DMRG simulation, they can also be derived from any other method which yields N-representable one-, two-, three-, and four-particle RDMs (so you have to be very careful with methods like coupled cluster which arrive at these operators using response theory). In particular, the one-orbital RDM is given in terms of a subset of elements of the one- and two-particle RDMs and the two-orbital RDM in terms of specific elements of the one-, two-, three-, and four-particle RDMs. See Refs [Cite 20-26: Rissler 2006, Barcza 2010, Boguslawski 2012, Boguslawski 2012a, Boguslawski 2013a, Boguslawski 2015, Barcza 2015] for more details.

Why bother using MPS wave functions with a 1D entanglement structure for something as complex as molecules? Don't these ansätze limit the molecules we can study to 1D topologies, with orbitals arranged in chains or rings?

In the tensor network community, people often study strongly-correlated 2D quantum systems using DMRG/MPS by curling up the 1D ansatz like a snake to cover the 2D lattice, thereby introducing unnatural long-range interactions between neighbouring sites. In many cases, the computational efficiency of MPS [due to the existence of isometric, canonical forms of the tensors which simplify the contractions (number of matrix multiplications) and also stabilize the eigenvalue problems (conditioning)] outweighs the additional complexity of 2D extensions of the MPS ansatz such as Projected-entangled Pair States (PEPS). Actually, the development of fast and accurate numerical PEPS algorithms for 2D quantum lattice systems is still very much an active area of research.

APPENDIX 2 REFERENCES

1 C. Riplinger, and F. Neese, "An efficient and near linear scaling pair natural orbital based local coupled cluster method", Journal of Chemical Physics 138, 34106 (2013).

2 C. Riplinger, B. Sandhoefer, A. Hansen, and F. Neese, "Natural triple excitations in local coupled cluster calculations with pair natural orbitals", Journal of Chemical Physics 139, 134101 (2013).

3 S. R. White, and R. L. Martin, "Ab initio quantum chemistry using the density matrix renormalization group", Journal of Chemical Physics 110, 4127-4130 (1999).

4 S. Wouters, "Accurate variational electronic structure calculations with the density matrix renormalization group", Ghent University (2014).

5 J. Hachmann, "Ab initio density matrix renormalization group methodology and computational transition metal chemistry", Cornell University (2010).

6 S. Knecht, E. D. Hedegård, S. Keller, A. Kovyrshin, Y. Ma, A. Muolo, C. J. Stein, and M. Reiher, "New Approaches for ab initio Calculations of Molecules with Strong Electron Correlation", CHIMIA International Journal for Chemistry 70, 244-251 (2015).

7 S. Wouters, and D. Van Neck, "The density matrix renormalization group for ab initio quantum chemistry", European Physical Journal D 68 (2014) 10.1140/epjd/e2014-50500-1.

8 G. K.-L. Chan, J. J. Dorando, D. Ghosh, J. Hachmann, E. Neuscamman, H. Wang, and T. Yanai, "An Introduction to the Density Matrix Renormalization Group Ansatz in Quantum Chemistry", Progress in Theoretical Chemistry and Physics 18, 49-65-65 (2008).

9 G. K.-L. Chan, and S. Sharma, "The Density Matrix Renormalization Group in Quantum Chemistry", Annual Review of Physical Chemistry 62, 465-481 (2011).

10 R. Olivares-Amaya, W. Hu, N. Nakatani, S. Sharma, J. Yang, and G. K. L. Chan, "The ab-initio density matrix renormalization group in practice", Journal of Chemical Physics 142, 34102 (2015).

11 G. K.-L. Chan, *Ab initio DMRG and beyond for realistic systems*, 2015.

12 N. Nakatani, and G. K. L. Chan, "Efficient tree tensor network states (I INS) for quantum chemistry: Generalizations of the density matrix renormalization group algorithm", Journal of Chemical Physics 138, 134113 (2013).

13 V. Murg, F. Verstraete, R. Schneider, P. R. Nagy, and Legeza, "Tree tensor network state with variable tensor order: An efficient multireference method for strongly correlated systems", en, Journal of Chemical Theory and Computation 11, 1027-1036 (2015).

14 K. Gunst, F. Verstraete, S. Wouters, Ö. Legeza, and D. Van Neck, "T3NS: Three-Legged Tree Tensor Network States", Journal of Chemical Theory and Computation 14, 2026-2033 (2018).

15 K. H. Marti, B. Bauer, M. Reiher, M. Troyer, and F. Verstraete, "Complete-graph tensor network states: A new fermionic wave function ansatz for molecules", New Journal of Physics 12, 103008 (2010).

16 C. J. Stein, and M. Reiher, "Automated Selection of Active Orbital Spaces", Journal of Chemical Theory and Computation 12, 1760-1771 (2016)

17 C. J. Stein, and M. Reiher, "Measuring multi-configurational character by orbital entanglement", Molecular Physics 115, 2110-2119 (2017).

18 S. Keller, K. Boguslawski, T. Janowski, M. Reiher, and P. Pulay, "Selection of active spaces for multiconfigurational wavefunctions", eng, Journal of Chemical Physics 142, 244104 (2015).

19 D. Ghosh, J. Hachmann, T. Yanai, and G. K. L. Chan, "Orbital optimization in the density matrix renormalization group, with applications to polyenes and ß-carotene", Journal of Chemical Physics 128, 144117 (2008).

20 K. Boguslawski, P. Tecmer, Ö. Legeza, and M. Reiher, "Entanglement measures for single- and multireference correlation effects", en, Journal of Physical Chemistry Letters 3, 3129-3135 (2012).

21 K. Boguslawski, P. Tecmer, G. Barcza, Ö. Legeza, and M. Reiher, "Orbital entanglement in bond-formation processes", Journal of Chemical Theory and Computation 9, 2959-2973 (2013).

22 K. Boguslawski, K. H. Marti, Ö. Legeza, and M. Reiher, "Accurate ab initio spin densities", Journal of Chemical Theory and Computation 8, 1970-1982 (2012).

23 G. Barcza, R. M. Noack, J. Sólyom, and Ö. Legeza, "Entanglement patterns and generalized correlation functions in quantum many-body systems", Physical Review B 92, 125140 (2015).

24 J. Rissler, R. M. Noack, and S. R. White, "Measuring orbital interaction using quantum information theory", Chemical Physics 323, 519-531 (2006).

25 G. Barcza, Ö. Legeza, K. II. Marti, and M. Reiher, "Quantum information analysis of electronic states at different molecular structures", Physical Review A 83 (2010) 10.1103/PhysRevA.83.012508.

26 K. Boguslawski, and P. Tecmer, "Orbital entanglement in quantum chemistry", International Journal of Quantum Chemistry 115, 1289-1295 (2015).

27 G. K. L. Chan, "Low entanglement wavefunctions", en, Wiley Interdisciplinary Reviews: Computational Molecular Science 2, 907-920 (2012).

28 S. Szalay, G. Barcza, T. Szilvási, L. Veis, and Ö. Legeza, "The correlation theory of the chemical bond", en, Scientific Reports 7, 2237 (2017).

29 E. Fertitta, B. Paulus, G. Barcza, and Ö. Legeza, "Investigation of metal-insulator like transition through the <i>ab initio</i> density matrix renormalization group approach", Physical Review B 90, 245129 (2014).

30 C. Duperrouzel, P. Tecmer, K. Boguslawski, G. Barcza, Ö. Legeza, and P. W. Ayers, "A quantum informational approach for dissecting chemical reactions", Chemical Physics Letters 621, 160-164 (2015).
31. G. K. L. Chan, and M. Head-Gordon, "Highly correlated calculations with a polynomial cost algorithm: A study of the density matrix renormalization group", Journal of Chemical Physics 116, 4462-476 (2002).
32. R. J. Bartlett, and M. Musial, "Coupled-cluster theory in quantum chemistry", Reviews of Modern Physics 79, 291-352 (2007).
33. D. Zgid, and M. Nooijen, "Obtaining the two-body density matrix in the density matrix renormalization group method", The Journal of Chemical Physics 128, 144115 (2008).
34. Y. Ma, and H. Ma, "Assessment of various natural orbitals as the basis of large active space density-matrix renormalization group calculations", Journal of Chemical Physics 138, 224105 (2013).
35. Z. Li, H. Li, B. Suo, and W. Liu, "Localization of molecular orbitals: From fragments to molecule", Accounts of Chemical Research 47, 2758-2767 (2014).
36. S. F. Keller, and M. Reiher, "Determining Factors for the Accuracy of DMRG in Chemistry", en, CHIMIA International Journal for Chemistry 68, 200-203 (2014).
37. S. Wouters, T. Bogaerts, P. Van Der Voort, V. Van Speybroeck, and D. Van Neck, "Communication: DMRG-SCF study of the singlet, triplet, and quintet states of oxo-Mn(Salen)", en, Journal of Chemical Physics 140 (2014) 10.1063/1.4885815.
38. A. Kovyrshin, and M. Reiher, "Self-adaptive tensor network states with multi-site correlators", en, Journal of Chemical Physics 147, 214111 (2017).
39. M. Reiher, *Three Lectures on DMRG in Quantum Chemistry Three Lectures on DMRG in Quantum Chemistry*, en, edited by M. Reiher, 2014.
40. M. Reiher, *DMRG in Quantum Chemistry: From its relation*
41. G. Moritz, B. A. Hess, and M. Reiher, "Convergence behavior of the density-matrix renormalization group algorithm for optimized orbital orderings", Journal of Chemical Physics 122, 24107 (2005).
42. Y. Ma, J. Wen, and H. Ma, "Density-matrix renormalization group algorithm with multi-level active space", Journal of Chemical Physics 143, 34105 (2015).
43. K. Boguslawski, "How quantum entanglement can promote the understanding of electronic structures of molecules", en, 37 (2013).
44. M. Reiher, ed., *The first second-generation DMRG program for quantum chemistry*, en, 2014.
45. S. Sharma, and G. K.-L. Chan, "Spin-adapted density matrix renormalization group algorithms for quantum chemistry", The Journal of Chemical Physics 136, 124121 (2012).
46. C. Krumnow, L. Veis, Legeza, and J. Eisert, "Fermionic orbital optimization in tensor network states", Physical Review Letters 117 (2016) 10.1103/PhysRevLett.117.210402.
47. F. Liu, Y. Kurashige, T. Yanai, and K. Morokuma, "Multireference ab initio density matrix renormalization group (DMRG)-CASSCF and DMRG-CASPT2 study on the photochromic ring opening of spiropyran", Journal of Chemical Theory and Computation 9, 4462-4469 (2013).
48. K. H. Marti, and M. Reiher, "The density matrix renormalization group algorithm in quantum chemistry", Zeitschrift fur Physikalische Chemie 224, 583-599 (2010).
49. C. J. Stein, V. Von Burg, and M. Reiher, "The Delicate Balance of Static and Dynamic Electron Correlation", Journal of Chemical Theory and Computation 12, 3764-3773 (2016).
50. M. W. Schmidt, and M. S. Gordon, "the Construction and Interpretation of Mcscf Wavefunctions", Annual Review of Physical Chemistry 49, 233-266 (1998).
51. F. Neese, *Local Correlation Approaches*, en, edited by F. Neese,
52. J. B. Parkinson, and D. J. J. Farnell, "The Coupled Cluster Method", arXiv:1506.06914 [math-ph, physics: quant-ph], 109-134 (2010).
53. G. K.-L. Chan, A. Keselman, N. Nakatani, Z. Li, and S. R. White, "Matrix Product Operators, Matrix Product States, and ab initio Density Matrix Renormalization Group algorithms", arXiv:1605.02611 [cond-mat, physics:physics, physics:quant-ph] (2016) 10.1063/1.4955108.
54. Legeza, and J. Sólyom, "Optimizing the density-matrix renormalization group method using quantum information entropy", Physical Review B—Condensed Matter and Materials Physics 68, 195116 (2003).
55. D. A. Mazziotti, "Structure of Fermionic density matrices: Complete N-representability conditions", Physical Review Letters 108, 263002 (2012).
56. D. Ma, G. Li Manni, and L. Gagliardi, "The generalized active space concept in multiconfigurational self-consistent field methods", Journal of Chemical Physics 135, 44128 (2011).
57. D. Zgid, and M. Nooijen, "The density matrix renormalization group self-consistent field method: Orbital optimization with the density matrix renormalization group method in the active space", Journal of Chemical Physics 128, 144116 (2008).
58. L. Veis, A. Antalik, J. Brabec, F. Neese, Ö. Legeza, and J. Pittner, "Coupled Cluster Method with Single and Double Excitations Tailored by Matrix Product State Wave Functions", Journal of Physical Chemistry Letters 7, 4072-4078 (2016).
S. Wouters, W. Poelmans, P. W. Ayers, and D. Van Neck, "CheMPS2: A free open-source spin-adapted implementation of the density matrix renormalization group for ab initio quantum chemistry", Computer Physics Communications 185, 1501-1514 (2014).
60. A. Kovyrshin, and M. Reiher, "Tensor network states with three-site correlators", en, New Journal of Physics 18, 113001 (2016).

APPENDIX 3

Compact neural networks based on multiscale entanglement renormalization Ansatz. (A. Hallam, E. Grant, V. Stojevic, S. Severini, and A. G. Green, ArXiv e-prints (2017), arXiv:1711.03357.)

This Appendix 3 describes a method for tensorizing neural networks based upon an efficient way of approximating scale invariant quantum states, the Multi-scale Entanglement Renormalization Ansatz (MERA). We employ MERA as a replacement for the fully connected layers in a convolutional neural network and test this implementation on the CIFAR-10 and CIFAR-100 datasets. The proposed method outperforms factorization using tensor trains, providing greater compression for the same level of accuracy and greater accuracy for the same level of compression. We demonstrate MERA layers with 14000 times fewer parameters and a reduction in accuracy of less than 1% compared to the equivalent fully connected layers, scaling like O(N).

1 Introduction

The curse of dimensionality is a major bottleneck in machine learning, stemming from the exponential growth of variables with the number of modes in a data set (Cichocki et al. (2016)). Typically state-of-the-art convolutional neural networks have millions or billions of parameters. However, previous work has demonstrated that representations stored in the network parameters can be highly compressed without significant reduction in network performance (Novikov et al. (2015), Garipov et al. (2016)). Determining the best network architecture for a given task remains an open problem. Descriptions of quantum mechanical systems raise a similar challenge; representing n d-dimensional particles requires a rank-n tensor whose memory cost scales as $d^n$. Indeed, it was the promise of harnessing this that led Richard Feynman to suggest the possibility of quantum computation. In the absence of a quantum computer, however, one must use compressed representations of quantum states.

A level of compression can be achieved by factorizing the tensorial description of the quantum wavefunction. Many such factorizations are possible, the optimal structure of the factorization being determined by the structure of correlations in the quantum system being studied. A revolution in quantum mechanics was made by realizing that the best way to characterize the distribution of correlations and information in a state is by a quantity known as entanglement—loosely the mutual quantum information between partitions of a quantum system (Eisert et al. (2010)).

This has led to many successful applications of tensorial approaches to problems in solid state physics and quantum chemistry over the past 25 years (Orus (2014), Kin-Lic Chan et al. (2007)).

Intriguing ideas have also emerged over the past few years attempting to bridge the successes of neural networks in machine learning with those of tensorial methods in quantum physics, both at a fundamental level (Lin et al. (2017), Mehta & Schwab (2014)), and as a practical tool for network design (Levine et al. (2017)). Recent work has suggested that entanglement itself is a useful quantifier of the performance of neural networks (Levine et al. (2017), Liu et al. (2017))

The simplest factorization employed in quantum systems is known as the matrix product state (Orus (2014)). In essence, it expresses the locality of information in certain quantum states. It has already been adopted to replace expensive linear layers in neural networks—in which context it has been independently termed tensor trains (Oseledets (2011)). This led to substantial compression of neural networks with only a small reduction in the accuracy (Novikov et al. (2015), Garipov et al. (2016)). Here we use a different tensor factorization—known as the Multi-scale Entanglement Renormalization Ansatz (MERA)—that encodes information in a hierarchical manner (Vidal (2008)). MERA works through a process of coarse graining or renormalization. There have been a number of papers looking at the relationship between renormalization and deep learning. MERA is a concrete realization of such a renormalization procedure (Vidal (2009)) and so possesses a multi-scale structure that one might anticipate in complex data. A number of works have utilized tree tensor network models that possess a similar hierarchical structure. However, they do not include the disentangler tensors that are essential if each layer of the MERA is to capture correlations on different length scales (Liu et al. (2017)).

In this work we employ MERA as a replacement for linear layers in a neural network used to classify the CIFAR-10 and CIFAR-100 datasets. Our results show that this performs better than the tensor train decomposition of the same linear layer, and gives better accuracy for the same level of compression and better compression for the same level of accuracy. In Section 3.2 we introduce factorizations of fully connected linear layers, starting with the tensor train factorization followed by a tree-like factorization and finally the MERA factorization. In Section 3.3 we discuss how this is employed as a replacement for a fully connected linear layer in deep learning networks. Section 3.4 gives our main results and we note connections with the existing literature in Section 3.5. Finally, in Section 3.6 we discuss some potential developments of the work.

2 Tensor Factorization of Linear Layers

In this report we have replaced the linear layers of the standard neural network with tensorial MERA layers. The first step in achieving this involves expressing a linear layer as a tensor. This can be accomplished by taking a matrix W and reshaping it to be a higher dimensional array. For example, suppose W is $d^n$ by $d^n$ dimensional with components $W_{AB}$. It can be transformed into a rank 2n tensor by mapping A to n elements A→$i_1, i_2, \ldots, i_n$ and B to another n elements B→$j_1, j_2, \ldots, j_n$. In this case each of the elements of the new tensor will be of size d.

Figure 11:
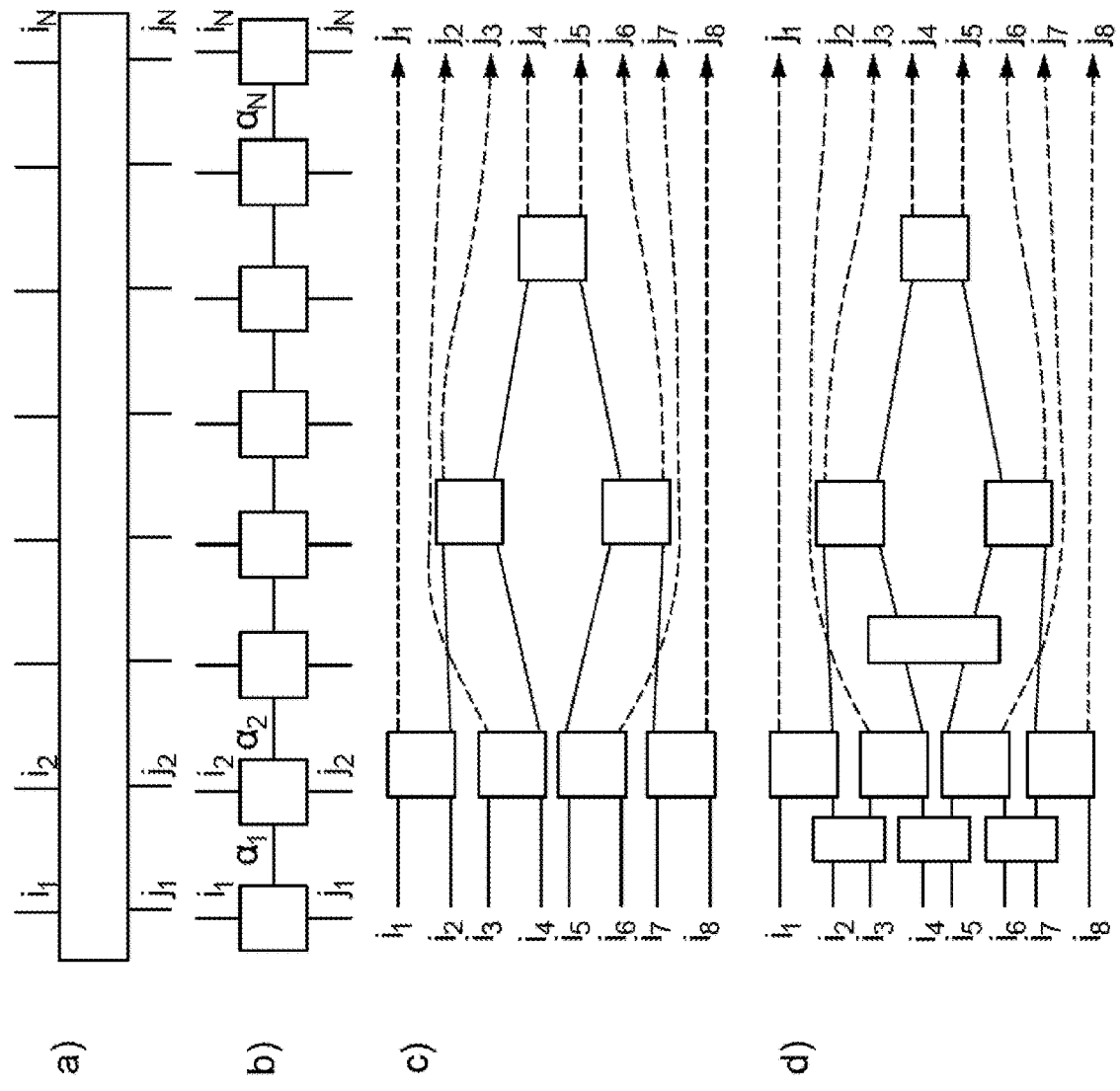
FIG. 11 shows schematic diagrams of various tensor factorizations of linear layers.

FIG. 11 shows schematic diagrams of various tensor factorizations of linear layers: a) a general linear layer, b) its tensor train factorization. The squares represent smaller tensors. Connections represent contractions as indicated in Equation 1 (as seen in FIG. 12) c) Tree network factorization. d) MERA factorization.

FIG. 11a gives a graphical representation of this rank $2_n$ tensor $$W^{i_1, i_2, \ldots, i_n}_{j_1, j_2, \ldots, j_n}.$$

It is important to note that in this representation, the lines represent the indices of the tensors rather than weights. FIG. 1b illustrates the tensor train decomposition of W. This consists of writing the larger tensor as the contraction of a train of smaller tensors, as shown in Equation 1 (FIG. 12).

$$W^{i_1, i_2, \ldots, i_n}_{j_1, j_2, \ldots, j_n} = \sum_{\alpha_1, \alpha_2, \ldots, \alpha_{n-1}} A^{i_1}_{j_1, \alpha_1} A^{\alpha_1, i_1}_{j_1, \alpha_2} \ldots A^{\alpha_{n-1}, i_n}_{j_n}. \quad (1)$$

In the tensor graphical notation, closed legs represent indices being summed over and free legs represent indices that aren't being summed over. For example, in equation 1 the $\alpha_i$ indices are being summed over and in FIG. 11b the $\alpha_i$ lines are connected to tensors at both ends.

If each index runs over values from 1 to d, this represents an exponential reduction from $d^{2n}$ parameters to $n(Dd)^2$, where the indices $\alpha$ run over values from 1 to D (known as the bond order or Schmidt rank in the quantum context). As noted above, this type of tensor factorization works well in physics when the information has a local structure (Eisert et al. (2010), Verstraete & Cirac (2006)); tensor trains capture correlations effectively up to length scales of order log D (Schollwock (2011)). This means that while useful for many tasks, the learned representations will be highly local. Tensors at either end of a tensor train decomposition of a linear layer will not be strongly correlated with one another.

A hierarchically structured tensor network can better represent correlations across the linear layer.

The tree tensor network shown in FIG. 11c represents one possible hierarchical factorization. Each element of this network is a rank 4 tensor. The two tensors on the top left would have the form:

$$M_{i_1,i_2}^{j_1,\alpha_1} \text{ and } N_{i_3,i_4}^{j_2,\alpha_2}.$$

The $i_n$ elements being represented by the lines on the left of the figure, the $j_n$ elements represented by the dotted lines on the right of the figure and the $\alpha_n$ lines being those connected with the tensor immediately to the right of $M$ and $N$.

Reading from left to right FIG. 11c can be interpreted as follows: the tree-like connectivity imbues the network with a causal structure whereby a given linear element and its outputs are influenced by inputs in a region determined by its height in the tree.

For example, the rightmost element in FIG. 11c is influenced by all of the inputs, whereas the top element in the middle column is influenced by inputs $i_1$ to $i_4$. Elements other than the rightmost tensor have one dashed output (that connects directly to the overall output) and one solid output (that ties it to the branching tree structure). These dashed lines are controlled by representations occurring on a particular scale in the data.

Notice that removing these dashed lines, the network has a true tree structure and represents a coarse graining or renormalization of the network. In this case, the linear elements are the isometrics of the original MERA's definition (Vidal (2008; 2009)).

The simple tree network, which has been studied before in the context of neural networks, has a major deficiency. At each branching, it partitions the system in two, so that in extremis, the correlations between neighbouring inputs—for example i4 and i5 in FIG. 11c—are only controlled by the element at the end of the network. Requiring the higher elements in the tree-structure to capture correlations between neighbouring inputs restricts their ability to describe the longer length scale correlations you would hope to capture by using a hierarchical structure.

The MERA (Vidal (2009)) factorization was introduced in order to solve this problem. As can be seen in FIG. 1d it adds an additional set of rank 4 tensors called disentanglers. The MERA is constructed by taking a tree network and placing one of these rank 4 tensors $$D_{\gamma_1,\gamma_2}^{\beta_1,\beta_2}$$

such that its right-going legs $\beta_1$ and $\beta_2$ connect to two adjacent tensors of the tree network. For example, if we consider the top left-most disentangler in FIG. 11d it has elements $$D_{i_2,i_3}^{\beta_1,\beta_2}$$

and connects to the tree and $$N_{\beta_2,i_4}^{\prime j_2,\alpha_2}$$

with $\beta_1$ and $\beta_2$ then being summed over.

The role of the disentanglers is to cause all correlations on the same length scale to be treated similarly. For example, correlations between any two neighbouring input indices $i_n$ and $i_{n+1}$ will be captured by either the first row of tree elements or the disentanglers. This allows the later elements in the network to work at capturing longer range correlations.

In summary, a rank-N MERA layer can be constructed in the following manner:
1. Create a tree tensor layer. For example, an $N=2^\tau$ tree can be constructed from $2^{\tau-1}$ rank-4 tree tensors $$M_{\gamma_1,\gamma_2}^{\beta_1,\beta_2}$$

in the first layer, followed by $2^{\tau-2}$ tree tensors in the second layer until after T layers there is only a single tree tensor.
2. A set of disentanglers are introduced. These are rank-4 tensors $$D_{\gamma_1,\gamma_2}^{\beta_1,\beta_2}$$

which are placed such that every disentangler is contracted with two neighbouring tree tensors in an upcoming layer of the tree tensor.

3 Experiments and Network Structure

We have considered the performance of a neural network with the two penultimate fully connected layers of the model replaced with MERA layers, similar to the Novikov et al. (2015) study of compression of fully connected layers using tensor trains. We have quantified the performance of the MERA layer through comparisons with two other classes of networks: fully connected layers with varying numbers of nodes and tensor train layers with varying internal dimension. The three types of network are otherwise identical. The networks consisted of three sets of two convolutional layers each followed by max pooling layers with 3×3 kernels and stride 2. The convolutional kernels were 3×3. There were 64 channels in all of the convolutional layers except for the input, which had three channels, and the last convolutional layer, which had 256 channels. The final convolutional layer was followed by two more hidden layers, these were either fully connected, MERA layers or TT-layers depending upon the network. The first of these layers was of size 4096×x, the second is of size x×64. For the MERA and TT networks, these layers were 4096×4096 and 4096×64.

The final layer had 10 or 100 nodes corresponding to the image classes in CIFAR-10 and CIFAR-100. Leaky rectified linear units (LReLU) were used on all layers except the final layer, with leak=0:2 (Maas et al. (2013)).

During training, nodes in the final convolutional layer and the two first fully connected layers were dropped with probability 0:5. The penultimate convolutional layer nodes were dropped with probability 0:2 (Srivastava et al. (2014)).

Batch-normalization was used on all layers after dropout and max pooling (Ioffe & Szegedy (2015)). We did not use bias units. Gaussian weight initialization was employed in the fully connected models with standard deviation equal to $$\frac{1}{\sqrt{n_{in}}},$$

where $n_{in}$ was the number of inputs (He et al. (2015)).

In this report we considered networks with two varieties of fully-connected layers. The first of these networks had a 4096×4096 fully connected layer followed by one which was 4096×64; this network was used as a benchmark against which the other models could be compared. The second network instead had a 4096×n fully connected layer followed by a n×64 layer where n=5 for the CIFAR-10 network and n=10 for the CIFAR-100 network. We trained these network to compare the MERA and tensor train layers to a fully connected model with a comparable number of parameters, in order to evaluate how detrimental naive compression is to accuracy.

Figure 13:
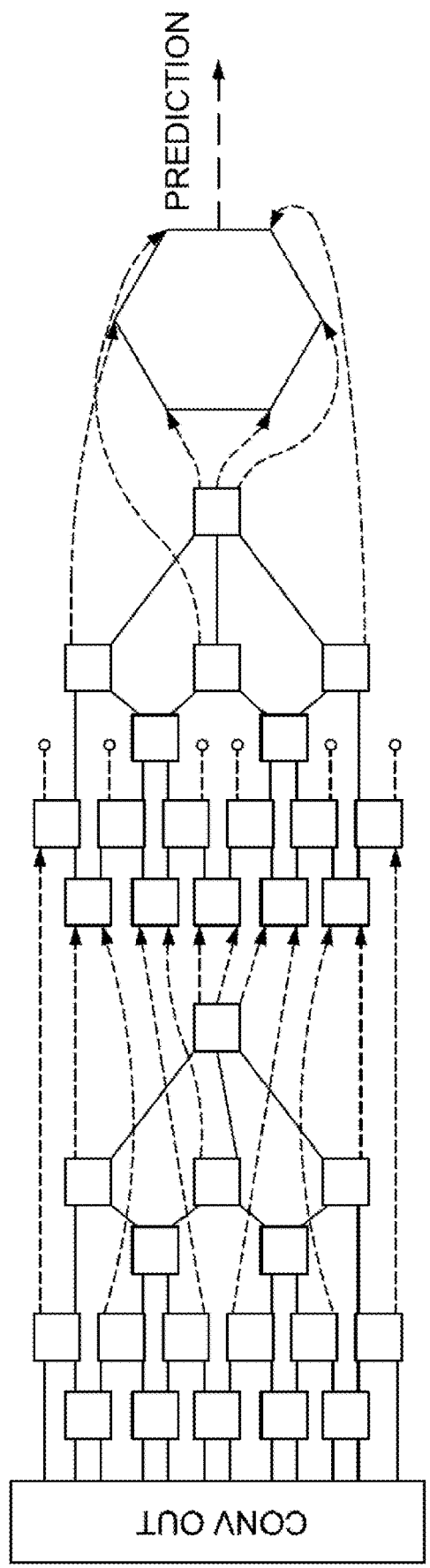
FIG. 13 shows a schematic of the MERA layers of the model.

A schematic of the two MERA layers can be found in FIG. 13. The input to the first MERA layer was reshaped in to a rank-12 tensor with each index being dimension 2, as described in Section 3.2. The MERA layer was then constructed from a set of rank-4 tensors using the method described in Section 3.2.

FIG. 13 shows a schematic of the MERA layers of the model. The small rectangles represent linear elements to factorize a general linear layer. White rectangles represent disentanglers. Black rectangles represent tree elements. Solid black lines connecting nodes represent tensor contraction and dashed lines with arrow heads represent the non-linearities being applied. Dashed lines ending in a circle represent fixed outputs.

The first MERA layer works as follows: It contains a column of 6 rank-4 tree elements, followed by 3 tree elements and finally a single tree element. 5 disentanglers are placed before the first column of tree elements and 2 more disentanglers are placed before the second column of tree elements.

The second MERA layer has an identical structure to the first MERA layer, one of the outputs of the first set of tree elements is fixed. As a result the output of the second MERA layer is 64 nodes. MERA weights were initialized using elements of randomized orthogonal matrices (Saxe et al. (2013)). The tensors themselves were constructed by reshaping these matrices, as described in Section3.2. The random orthogonal matrix was constructed using the method of Stewart. Starting from a random n−1×n−1 dimensional orthogonal matrix, a random n×n dimensional orthogonal matrix can be constructed by taking a randomly distributed n-dimensional vector, constructing its Householder transformation, and then applying the n−1 dimensional matrix to this vector. Finally, a network with its fully connected layers replaced with a tensor train decomposition was trained in order to provide a comparison with the MERA layers. The tensor train layers were constructed as described in Section 3.2 with the internal dimension being fixed at D=3. In the second tensor train layer, half of the output indices were fixed to match the second MERA layer. We tested performance on the CIFAR-10 and CIFAR-100 datasets. We used 45; 000 images for training, 5; 000 for validation and 10; 000 for testing. Each training batch consisted of 50 images.

Training data was augmented by randomly flipping and translating the input images by up to 4 pixels. Translated images were padded with zeros. All images were normalized by dividing by 255 and subtracting the mean pixels value from the training set.

Validation and test set accuracy was recorded every 500 iterations and training was stopped when validation accuracy did not improve for 10 successive tests. The network was trained using backpropagation and the Adam optimizer, with initial learning rate 0:001 (Kingma & Ba (2014)) and a softmax-cross-entropy objective. The test set accuracy for the model with the highest validation set accuracy was recorded. Each network was trained 10 times with a different random weight initialization.

The networks were implemented in Tensorflow r1.3 and trained on NVIDIA Titan Xp and 1080ti GPUs.

4. Experimental Results

FIG. 14 shows a table of results in which we compare the different models described in section 3.3 trained on the CIFAR-10 dataset. FC1 was the fully-connected model and FC2 was the fully-connected model with severely reduced number of parameters in the fully-connected layers. MERA are the result for the MERA inspired network. Finally TT is the tensor train model with the internal dimension being 3.

The compression rate stated is with respect to the number of parameters used in the fully-connected benchmark model, FC-1.

When comparing the MERA network to the fully connected model, FC-1 we see a considerable drop in the number of parameters required with only a modest drop in the accuracy of the network.

MERA compresses the fully connected layers by a factor of 14,000 with a drop in the accuracy of only 0:4%. We do not attempt to compress the convolutional layers in this work so in the MERA network the vast majority of the parameters are used in the convolutional layers, which are identical to the fully connected model.

How significant is the MERA network structure we have chosen to the results obtained? To test this we compare the MERA results obtained to the fully connected model with many fewer parameters in the fully connected layers, FC-2. Despite having around 20 times more parameters in the fully connected layer than the MERA model, the MERA model significantly out performs FC-2, with a 1:2% drop in the accuracy of FC-2 compared to MERA. The MERA network also compares favourably to a tensor train network. In this case, the two networks have a comparable number of parameters but the MERA appears to achieve a higher accuracy than the tensor train network in this case.

Results for the CIFAR-100 model can be seen in FIG. 15. While none of the networks are as accurate as the benchmark case, the MERA network continues to outperform the tensor train and ablated fully connected network. However, the reduction in accuracy compared to the fully connected network is larger than for the CIFAR-10 dataset.

In addition to the degree of compression achieved by these networks, we also address the time to optimize. There is evidently a degree of compromise required here: the number of multiplications required to apply a MERA layer scales with the input size N and bond order D as $N^{log\,2\,D}$ The equivalent scaling for a tensor train and fully connected layer are $ND^2$ and $N^2$, respectively. This is reflected in the times taken to optimize these networks. Note however, that MERA can accommodate correlations at all scales of its input even at low bond order, whereas tensor trains require a bond order that scales exponentially with the length scale of correlation (Orus (2014)). MERA is, therefore, expected to scale better for very large data sets than either tensor trains or fully connected layers.

5 Related Work

Given how memory intensive deep neural networks typically are, substantial effort has been made to reduce number of parameters these networks require without significantly reducing their accuracy. Some of these have taken a similar approach to the MERA network described above, using tensor decompositions of the fully connected layers.

These include the tensor train models of Novikov et al. (2015) and Garipov et al. (2016). Here we have found replacing a fully connected linear layer with a MERA factorization resulted in superior accuracy for a comparable number of parameters. More directly related to this MERA model are a number of tree tensor network models (Liu et al. (2017), Levine et al. (2017)). As Section 3.2 explained, tree tensor networks inconsistently capture correlations on the same length scale, this is the reason for the introduction of disentanglers. Tree tensors do not possess these and we expect them to struggle to capture long range correlations as effectively as MERA.

A MERA works through a process of coarse graining or renormalization. There have been a number of other papers looking at the relationship between renormalization and deep learning. Lin et al. (2017) argue that the effectiveness of deep neural networks should be thought of in terms of renormalization and Mehta & Schwab (2014) demonstrate an exact mapping between the variational renormalization group and restricted Boltzmann machines. In this report we have taken a different approach: only the fully connected layers of the network were replaced with MERA layers.

6 Discussion

We have shown that replacing the fully connected layers of a deep neural network with layers based upon the multi-scale entanglement renormalization ansatz can generate significant efficiency gains with only small reduction in accuracy. When applied to the CIFAR-10 data we found the fully connected layers can be replaced with MERA layers with 14,000 times less parameters with a reduction in the accuracy of less than 1%. The model significantly outperformed compact fully connected layers with 70-100 times as many parameters. Moreover, it outperformed a similar replacement of the fully connected layers with tensor trains, both in terms of accuracy for a given compression and compression for a given accuracy. While the MERA layer resulted in a larger accuracy drop in the CIFAR-100 case, it still outperformed a comparable tensor train network.

An added advantage—not explored here—is that a factorized layer can potentially handle much larger input data sets, thus enabling entirely new types of computation. Correlations across these large inputs can be handled much more efficiently by MERA than by tensor trains. Moreover, a compressed network may provide a convenient way to avoid over-fitting of large data sets. The compression achieved by networks with these factorized layers comes at a cost. They can take longer to train than networks containing the large fully connected layers due to the number of tensor contractions required to apply the factorized layer.

Our results suggest several immediate directions for future inquiry. Firstly, there are some questions about how to improve the existing model. For example, before the MERA layer is used the input is reshaped into a rank-12 tensor. There isn't a well defined method for how to perform this reshaping optimally and some experimentation is necessary. The best way to initialize the MERA layers is also still an open question.

The results presented here are a promising first step for using MERA in a more fundamental way.

Since MERA can be viewed as a coarse graining procedure (as explained in Section 3.2), and image data is often well represented in a hierarchical manner, one possibility would be to simply train a two-dimensional MERA directly on an image dataset, with no reference to a neural network. In Stoudenmire & Schwab (2016) a similar idea was explored with matrix product states being trained directly on MNIST. An alternative possibility would be the replacement of just the convolutional layers of the network with a two-dimensional MERA. Both of these approaches would be closer in spirit to the fundamental ideas about the relationships between quantum physics and machine learning proposed in Lin et al. (2017) and Mehta & Schwab (2014).

Additionally, there has been some work using entanglement measures to explore how correlations are distributed in deep neural networks, and then utilizing these in order to optimize the design of networks (Liu et al. (2017), Levine et al. (2017)). It would be intriguing to explore such ideas using MERA, for example by using the concrete MERA model explored in this paper, or one of the more ambitious possibilities mentioned above.

We end by noting two facts: any variational approximation to a quantum wavefunction can be used to construct a replacement for linear layers of a network. There are many examples and each may have its sphere of useful application. Moreover, quantum computers of the type being developed currently by several groups are precisely described by a type of tensor network (a finite-depth circuit—and one that may very soon be too large to manipulate classically) and could be used as direct replacement for linear layers in a hybrid quantum/classical neural computation scheme.

The invention claimed is:

1. A machine learning based method of identifying candidate, small, drug-like molecules, comprising the step of providing molecular orbital representations of drug-like molecules and/or parts of proteins relevant to an interaction with the molecules, as an input to a machine learning system, to predict molecular properties and identify candidate drug-like molecules, in which molecular orbital representations of drug-like molecules and/or parts of proteins relevant to an interaction with the molecules are represented as tensor networks in which the tensor network representations include networks describing states with volume law entanglement that allow for tensor networks describing density matrices, including both those that obey the area law, and those that do not, and arbitrary superpositions of tensor networks, containing elements in general from distinct types of architectures.

2. The method of claim 1 in which a tensor network is any mathematical object in an exponentially large Hilbert Space.

3. The method of claim 1 in which the tensor networks are one or more of the following: matrix product state (MPS), tensor train, multi-scale entanglement renormalization ansatz (MERA), projected entangled-pair states (PEPS), correlator product states, tree tensor networks, complete graph network states, tensor network states.

4. The method of claim 1 in which a type of architecture is a superposition of two MPS tensor networks with a MERA network.

5. The method of claim 1 in which tensorial networks are used to decompose high rank structures appearing in graph models, hence enabling quantum featurisation and modelling in the context of graph models.

6. The method of claim 1 in which a feature map is applied to input data to transform that input into a high dimensional tensor network structure.

7. The method of claim 1 in which the tensor network represents a set of simple descriptions of a whole dataset of molecules.

8. The method of claim 1 in which the tensor network representations include a training data set of small drug-like molecules and a target, in which the small drug-like molecules are known to bind to the target.

9. The method of claim 1 in which the training dataset is a tensor network representation of the molecular quantum states of small drug-like molecules and also a tensor network representation of the molecular quantum states of one or more targets, such as a protein to which a drug-like molecule may potentially bind.

10. A system for identifying candidate, small, drug-like molecules, the system comprising a computation engine comprising processing circuitry for executing a machine learning based method comprising the step of providing molecular orbital representations of drug-like molecules and/or parts of proteins relevant to an interaction with the molecules, as an input to a machine learning system, to predict molecular properties and identify candidate drug-like molecules, in which molecular orbital representations of drug-like molecules and/or parts of proteins relevant to an interaction with the molecules are represented as tensor networks;

in which the tensor network representations include networks describing states with volume law entanglement that allow for tensor networks describing density matrices, including both those that obey the area law, and those that do not, and arbitrary superpositions of tensor networks, containing elements in general from distinct types of architectures.

11. A molecule or class of molecules identified using a machine learning based method of identifying candidate, small, drug-like molecules, the method comprising the step of providing molecular orbital representations of drug-like molecules and/or parts of proteins relevant to an interaction with the molecules, as an input to a machine learning system, to predict molecular properties and identify candidate drug-like molecules, in which molecular orbital representations of drug-like molecules and/or parts of proteins relevant to an interaction with the molecules are represented as tensor networks;

in which the tensor network representations include networks describing states with volume law entanglement that allow for tensor networks describing density matrices, including both those that obey the area law, and those that do not, and arbitrary superpositions of tensor networks, containing elements in general from distinct types of architectures.

* * * * *